United States Patent
Sasaki et al.

(10) Patent No.: US 10,273,251 B2
(45) Date of Patent: Apr. 30, 2019

(54) COMPOSITION, CURED FILM, NEAR INFRARED RAY ABSORPTION FILTER, SOLID-STATE IMAGING DEVICE, INFRARED SENSOR, AND COMPOUND

(71) Applicant: FUJIFILM Corporation, Tokyo (JP)

(72) Inventors: Daisuke Sasaki, Shizuoka (JP); Yutaro Norizuki, Shizuoka (JP); Tokihiko Matsumura, Shizuoka (JP); Yoshihiro Jimbo, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/416,558

(22) Filed: Jan. 26, 2017

(65) Prior Publication Data

US 2017/0137444 A1 May 18, 2017

Related U.S. Application Data

(63) Continuation of application No. PCT/JP2015/073842, filed on Aug. 25, 2015.

(30) Foreign Application Priority Data

Aug. 26, 2014 (JP) ................. 2014-171163
Aug. 12, 2015 (JP) ................. 2015-159628

(51) Int. Cl.
| | | |
|---|---|---|
| C09B 23/04 | (2006.01) | |
| G02B 5/22 | (2006.01) | |
| G02B 5/20 | (2006.01) | |
| C07F 5/02 | (2006.01) | |
| H01L 27/148 | (2006.01) | |
| H01L 27/146 | (2006.01) | |
| C09B 57/00 | (2006.01) | |

(52) U.S. Cl.
CPC ............... *C07F 5/027* (2013.01); *C07F 5/02* (2013.01); *C09B 23/04* (2013.01); *C09B 57/00* (2013.01); *C09B 57/004* (2013.01); *G02B 5/208* (2013.01); *G02B 5/223* (2013.01); *H01L 27/14645* (2013.01); *H01L 27/14649* (2013.01); *H01L 27/14806* (2013.01)

(58) Field of Classification Search
CPC .. C09B 23/04; G02B 5/22; G02B 5/20; C07F 5/02; H01L 27/148; H01L 27/146
See application file for complete search history.

(56) References Cited

U.S. PATENT DOCUMENTS

| | | | |
|---|---|---|---|
| 5,973,158 A | 10/1999 | Usami et al. | |
| 2011/0012075 A1 | 1/2011 | Nii et al. | |
| 2011/0070407 A1 | 3/2011 | Kato et al. | |
| 2018/0017720 A1* | 1/2018 | Arimura | ................. C09B 57/00 |
| 2018/0017722 A1* | 1/2018 | Arimura | ................. B32B 27/18 |
| 2018/0136379 A1* | 5/2018 | Takishita | ................. B32B 7/02 |

FOREIGN PATENT DOCUMENTS

| | | | |
|---|---|---|---|
| JP | 10-231435 A | | 9/1998 |
| JP | 2009-185161 A | | 8/2009 |
| JP | 2009-263614 A | | 11/2009 |
| JP | 2011-68731 A | | 4/2011 |
| JP | 2011068371 | * | 4/2011 |
| JP | 2014-59550 A | | 4/2014 |

OTHER PUBLICATIONS

Lee et al., 2015, Caplus an 2015:442761.*
Enokida et al., 1997, Caplus an 1997:171881.*
JP2011068371 (machine translation), 2011.*
Fischer et al, "Near-Infrared Dyes and Fluorophores Based on Diketopyrrolopyrroles", Angew. Chem. Int. Ed., vol. 46, 2007, pp. 3750-3753.
International Search Report for PCT/JP2015/073842 (PCT/ISA/210) dated Nov. 24, 2015.
Written Opinion of the International Searching Authority for PCT/JP2015/073842 (PCT/ISA/237) dated Nov. 24, 2015.
English translation of Written Opinion of the International Searching Authority for PCT/JP2015/073842 (Forms PCT/ISA/237, PCT/IB/373 and PCT/IB/338) dated Mar. 9, 2017.
International Preliminary Report on Patentability for PCT/JP2015/073842 (Forms PCT/IB/326 and PCT/IB/373) dated Mar. 9, 2017.
Japanese Office Action with English Translation dated Jan. 9, 2018 for JP Patent Application No. 2016-545542.
Chinese Office Action issued in corresponding Chinese Application No. 201580044518.8 and dated Jun. 29, 2018.
Korean Office Action issued in corresponding Korean Application No. 10-2017-7002309 and dated Jun. 20, 2018.
Taiwanese Office Action issued in Taiwan Application No. 104127435, dated Nov. 20, 2018 with partial English translation.
Taiwanese Office Action issued in Taiwan Application No. 10721085060 dated Nov. 20, 2018 with partial English translation.

* cited by examiner

*Primary Examiner* — Sun Jae Yoo
(74) *Attorney, Agent, or Firm* — Birch, Stewart, Kolasch & Birch, LLP

(57) ABSTRACT

It is possible to provide a composition that has absorption in a near infrared region and that can form a film having transparency in a visible region. Provided are a cured film, a near infrared ray absorption filter, a solid-state imaging device, an infrared sensor, and a compound. Provided is a composition including: a near infrared ray absorption substance of which a maximum absorption wavelength is in a wavelength range of 700 to 1,000 nm and a value obtained by dividing absorbance at a wavelength of 550 nm by absorbance at the maximum absorption wavelength is 0.015 or less. In the near infrared ray absorption substance, a half-width of the maximum absorption wavelength is preferably 60 nm or less. The near infrared ray absorption substance is preferably a compound having a pyrrolopyrrole skeleton and more preferably a pyrrolopyrrole boron compound.

6 Claims, 2 Drawing Sheets

COMPOSITION, CURED FILM, NEAR INFRARED RAY ABSORPTION FILTER, SOLID-STATE IMAGING DEVICE, INFRARED SENSOR, AND COMPOUND

CROSS-REFERENCE TO RELATED APPLICATIONS

This application is a Continuation of PCT International Application No. PCT/JP2015/073842 filed on Aug. 25, 2015, which claims priority under 35 U.S.C. § 119(a) to Japanese Patent Application No. 2014-171163 filed on Aug. 26, 2014 and Japanese Patent Application No. 2015-159628 filed on Aug. 12, 2015. Each of the above application(s) is hereby expressly incorporated by reference, in its entirety, into the present application.

BACKGROUND OF THE INVENTION

1. Field of the Invention

The present invention relates to a composition, a cured film, a near infrared ray absorption filter, a solid-state imaging device, an infrared sensor, and a compound.

2. Description of the Related Art

In a video camera, a digital still camera, or a cellular phone with a camera function, a charge coupled device (CCD) or a complementary metal-oxide-semiconductor (CMOS) which is a solid-state imaging device for a color image is used. In such a solid-state imaging device, a silicon photodiode having sensitivity to a near infrared ray in a light receiving section thereof is used. Therefore, visibility correction is required and near infrared ray absorption filters are used in many cases.

As a near infrared ray absorption substance, a pyrrolopyrrole compound and the like are known (for example, JP2009-263614A and Angewante, chemie international edition of English Book 46, 3750-3753 (2007)).

SUMMARY OF THE INVENTION

Recently, further improvement of transparency of a near infrared ray absorption substance in a visible region is required.

Accordingly, an object of the invention is to provide a composition that can form a film having absorption in a near infrared region and having excellent transparency in a visible region. An object of the invention is to provide a cured film, a near infrared ray absorption filter, a solid-state imaging device, an infrared sensor, and a compound.

In view of the above circumstances, the present inventors diligently conduct research to find that the above objects can be achieved by using a near infrared ray absorption substance of which a maximum absorption wavelength is in a wavelength range of 700 to 1,000 nm and a value obtained by dividing absorbance at a wavelength of 550 nm by absorbance at the maximum absorption wavelength is 0.015 or less, and the invention is completed. Therefore, the invention provides below.

<1> A composition comprising: a near infrared ray absorption substance of which a maximum absorption wavelength is in a wavelength range of 700 to 1,000 nm and a value obtained by dividing absorbance at a wavelength of 550 nm by absorbance at the maximum absorption wavelength is 0.015 or less.

<2> A composition comprising: a compound represented by Formula (1) below;

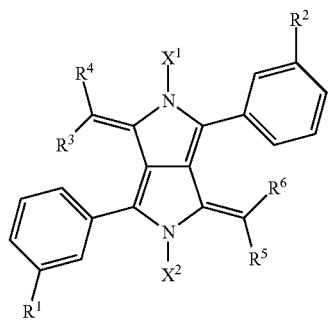

(1)

in Formula (1), $R^1$ and $R^2$ each independently represent a substituent, $R^3$ to $R^6$ each independently represent a hydrogen atom or a substituent, $R^3$ and $R^4$, and $R^5$ and $R^6$ may be respectively bonded to each other to form a ring, and $X^1$ and $X^2$ each independently represent a hydrogen atom or a substituent.

<3> The composition according to <1>, in which, the near infrared ray absorption substance has a maximum absorption wavelength of which a half-width is 60 nm or less.

<4> The composition according to <1> or <3>, in which the near infrared ray absorption substance is a compound having a pyrrolopyrrole skeleton.

<5> The composition according to <1> or <3>, in which the near infrared ray absorption substance is a pyrrolopyrrole boron compound.

<6> The composition according to <1>, <3>, <4>, or <5>, in which the near infrared ray absorption substance is a compound represented by Formula (1) below;

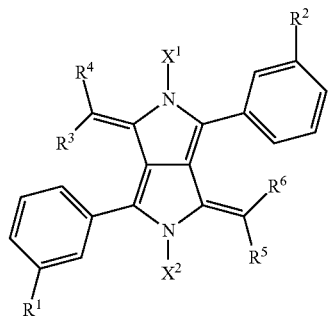

(1)

in Formula (1), $R^1$ and $R^2$ each independently represent a substituent, $R^3$ to $R^6$ each independently represent a hydrogen atom or a substituent, $R^3$ and $R^4$, and $R^5$ and $R^6$ may be respectively bonded to each other to form a ring, and $X^1$ and $X^2$ each independently represent a hydrogen atom or a substituent.

<7> The composition according to <2> or <6>, in which, in Formula (1), $R^1$ and $R^2$ each independently represent a hydrocarbon group that may include an oxygen atom.

<8> The composition according to <2> or <6>, in which, in Formula (1), $R^1$ and $R^2$ each independently represent an alkoxy group.

<9> The composition according to <2>, <6>, <7>, or <8>, in which, in Formula (1), one of $R^3$ and $R^4$ is an electron-withdrawing group, and the other one is a heteroaryl group, and one of $R^5$ and $R^6$ is an electron-withdrawing group, and the other one is a heteroaryl group.

<10> The composition according to <2>, <6>, <7>, <8>, or <9>, in which, in Formula (1), $X^1$ and $X^2$ each independently represent a hydrogen atom or $-BR^{21}R^{22}$; here, $R^{21}$ and $R^{22}$ each independently represent a substituent, and $R^{21}$ and $R^{22}$ are bonded to each other to form a ring.

<11> The composition according to any one of <1> to <10>, further comprising: a compound represented by Formula (1A) below;

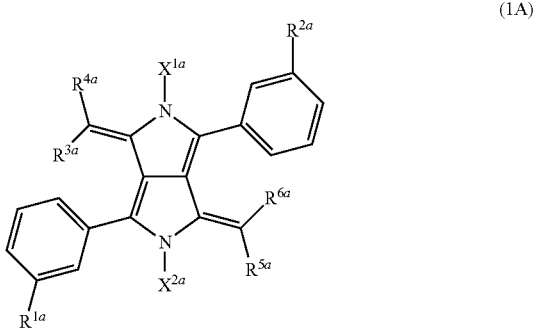

(1A)

in Formula (1A), $R^{1a}$ and $R^{2a}$ each independently represent a substituent, $R^{3a}$ to $R^{6a}$ each independently represent a hydrogen atom or a substituent, $R^{3a}$ and $R^{4a}$, and $R^{5a}$ and $R^{6a}$ are respectively bonded to each other to form a ring, $X^{1a}$ and $X^{2a}$ each independently represent a hydrogen atom or $-BR^{21a}R^{22a}$, and $R^{21a}$ and $R^{22a}$ each independently represent a substituent, and $R^{21a}$ and $R^{22a}$ are bonded to each other to form a ring.

<12> A cured film obtained by using the composition according to any one of <1> to <11>.

<13> A near infrared ray absorption filter comprising: a cured film obtained by using the composition according to any one of <1> to <11>.

<14> A solid-state imaging device comprising: a cured film obtained by using the composition according to any one of <1> to <11>.

<15> An infrared sensor comprising: a cured film obtained by using the composition according to any one of <1> to <11>.

<16> A compound represented by Formula (1A) below;

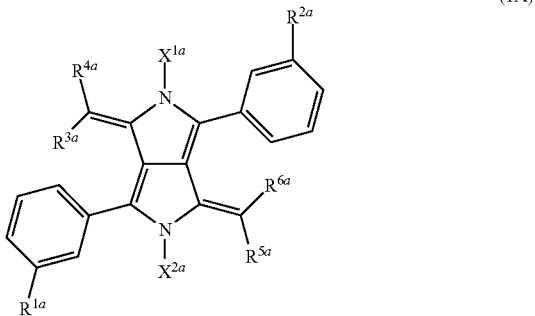

(1A)

in Formula (1A), $R^{1a}$ and $R^{2a}$ each independently represent a substituent, $R^{3a}$ to $R^{6a}$ each independently represent a hydrogen atom or a substituent, and $R^{3a}$ and $R^{4a}$, and $R^{5a}$ and $R^{6a}$ are respectively bonded to each other to form a ring, $X^{1a}$ and $X^{2a}$ each independently represent a hydrogen atom or $-BR^{21a}R^{22a}$, and $R^{21a}$ and $R^{22a}$ each independently represent a substituent, and $R^{21a}$ and $R^{22a}$ are bonded to each other to form a ring.

According to the invention, it is possible to provide a composition that can form a film having absorption in a near infrared region and having excellent transparency in a visible region. It is possible to provide a cured film, a near infrared ray absorption filter, a solid-state imaging device, an infrared sensor, and a compound.

DESCRIPTION OF THE PREFERRED EMBODIMENTS

Figure 1:
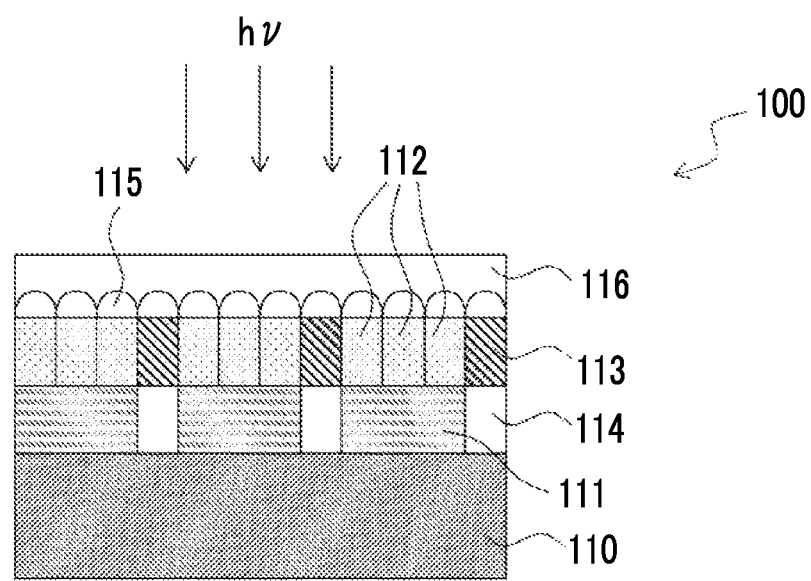
FIG. 1 is a cross-sectional view schematically illustrating a configuration according to an embodiment of an infrared sensor of the invention.

Hereinafter, the content of the invention is described in detail.

In this specification, the expression "to" is used in a meaning of including numerical values indicated before and after the expression as a lower limit and an upper limit.

In the description of a group (atomic group) in this specification, a denotation without substitution and unsubstitution include a group (atomic group) with a substituent, together with a group (atomic group) without a substituent. For example, an "alkyl group" includes not only an alkyl group (unsubstituted alkyl group) without a substituent but also an alkyl group (substituted alkyl group) with a substituent.

In this specification, "(meth)acrylate" represents acrylate and methacrylate, "(meth)acryl" represents acryl and methacryl, and "(meth)acryloyl" represents acryloyl and methacryloyl.

In this specification, a polymerizable compound refers to a compound having a polymerizable functional group. A polymerizable compound may be a monomer or may be a polymer. The polymerizable functional group refers to a group participating in polymerization reaction.

A method for measuring a weight-average molecular weight and a number-average molecular weight of a compound used in the invention can be measured by gel permeation chromatography (GPC), and defined as a value in terms of polystyrene by GPC measurement. For example, a weight-average molecular weight and a number-average molecular weight can be obtained by using HLC-8220 (manufactured by Tosoh Corporation), using TSK gel Super AWM-H (manufactured by Tosoh Corporation, 6.0 mm ID (inner diameter)×15.0 cm) as a column and using 10 mmol/L lithium bromide NMP (N-methylpyrrolidinone) solution as an eluent.

A near infrared ray refers to light (electromagnetic wave) of which a maximum absorption wavelength range is in a wavelength of 700 to 2,500 nm.

In this specification, a total solid content refers to a total mass of a component excluding a solvent from a total composition.

In this specification, the solid content refers to a solid content at 25° C.

<Composition>

The composition according to the invention contains a near infrared ray absorption substance of which a maximum absorption wavelength is in a wavelength range of 700 to 1,000 nm and a value obtained by dividing absorbance at a wavelength of 550 nm by absorbance at the maximum absorption wavelength is 0.015 or less.

The near infrared ray absorption substance is a substance having a maximum absorption wavelength in a wavelength range of 700 to 1,000 nm and the near infrared ray absorption substance is a substance of which absorption with respect to a wavelength region in a wavelength range of 500 to 600 nm is suppressed. The wavelength region in a wavelength range of 500 to 600 nm is a wavelength region in which visibility of a human is highest, but it is possible to suppress absorption of the wavelength region, and thus transparency in a visible region is excellent. Accordingly, the composition according to the invention has absorption in a near infrared region and it is possible to form a film having excellent transparency in a visible region.

In this specification, the expression "having a maximum absorption wavelength in a wavelength range of 700 to 1,000 nm" means having a wavelength exhibiting the maximum absorbance in a wavelength range of 700 to 1,000 nm in a absorption spectrum in a liquid of a near infrared ray absorption substance.

In this specification, the expressions "absorbance at a wavelength of 550 nm" and "absorbance at a maximum absorption wavelength" mean values obtained from an absorption spectrum of a liquid of an infrared absorption substance.

Examples of a measuring solvent used in the measuring of the absorption spectrum in the liquid of the near infrared ray absorption substance include chloroform, ethyl acetate, and tetrahydrofuran.

In this specification, with respect to "a value obtained by dividing absorbance of a near infrared ray absorption substance at a wavelength of 550 nm by absorbance of the maximum absorption wavelength", a value measured by using any one of the measuring solvents described above is preferably 0.015 or less, and values in all measuring solvents described above are more preferably 0.015 or less.

With respect to the near infrared ray absorption substance, a half-width of the maximum absorption wavelength is preferably 60 nm or less, more preferably 50 nm or less, and even more preferably 45 nm or less. For example, the lower limit is preferably 5 nm or greater. If the half-width of the maximum absorption wavelength is in the range described above, it is possible to form a near infrared ray absorption filter and the like that can selectively absorb light in a specific near infrared region.

The near infrared ray absorption substance is preferably a compound, more preferably a compound having a pyrrolopyrrole skeleton, and even more preferably a pyrrolopyrrole boron compound.

The near infrared ray absorption substance is a compound having a pyrrolopyrrole skeleton and is preferably a compound having a structure in which a pyrrolopyrrole ring hardly receive an influence of an electric effect. Specific reasons thereof are not clear, but if a compound has a structure that hardly receive an effect of an electric effect, absorption in a visible region (particularly, absorption in a wavelength range of 500 to 600 nm) can be suppressed.

The near infrared ray absorption substance is preferably a compound represented by Formula (1) described below and more preferably a compound represented by Formula (1A) described below. The compounds represented by Formulae (1) and (1A) are a compound having a substituent at a meta position of a phenyl group that is bonded to a pyrrolopyrrole skeleton. This compound is a structure that hardly receives an influence of an electric effect, and thus absorption in a visible region (absorption particularly in a wavelength range of 500 to 600 nm) can be suppressed, and thus it is possible to further reduce the absorbance ratio. Thus, the compound has a substituent at a meta position, and thus has excellent solvent solubility.

Another one of the composition of the invention contains a compound represented by Formula (1) described below.

Hereinafter, a compound represented by Formula (1) is described.

<<Compound Represented by Formula (1)>>

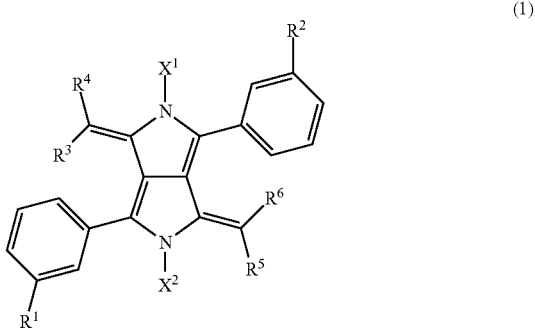

In Formula (1), $R^1$ and $R^2$ each independently represent a substituent, $R^3$ to $R^6$ each independently represent a hydrogen atom or a substituent, $R^3$ and $R^4$, and $R^5$ and $R^6$ may be respectively bonded to each other to form a ring, and $X^1$ and $X^2$ each independently represent a hydrogen atom or a substituent.

Examples of the substituent represented by $R^1$ and $R^2$ include a hydrocarbon group that may include an oxygen atom, a heteroaryl group, an amino group, an acylamino group, an alkoxycarbonylamino group, an aryloxycarbonylamino group, a sulfonylamino group, a sulfamoyl group, a carbamoyl group, an alkylthio group, an arylthio group, a heteroarylthio group, an alkylsulfonyl group, an arylsulfonyl group, a sulfinyl group, a ureido group, a phosphoric acid amide group, a mercapto group, a sulfo group, a carboxyl group, a nitro group, a hydroxamic acid group, a sulfino group, a hydrazino group, an imino group, a silyl group, a hydroxyl group, a halogen atom, and a cyano group.

The heteroaryl group is preferably a monocyclic ring or a fused ring, is preferably a monocyclic ring or a fused ring having a fused number of 2 to 8, and more preferably a monocyclic ring or a fused ring having a fused number of 2 to 4. The number of hetero atoms that form a heteroaryl group is preferably 1 to 3. A hetero atom that forms a heteroaryl group is preferably a nitrogen atom, an oxygen atom, or a sulfur atom. The number of carbon atoms of a heteroaryl group is preferably 3 to 30, more preferably 3 to 18, more preferably 3 to 12, and particularly preferably 3 to 5. The heteroaryl group is preferably a 5-membered or 6-membered ring. Specific examples of a heteroaryl group include an imidazolyl group, a pyridyl group, a pyrazyl group, a pyrimidyl group, a pyridazyl group, a triazyl group, a quinolyl group, a quinoxalyl group, an isoquinolyl group, an indolenyl group, a furyl group, a thienyl group, a benzoxazolyl group, a benzimidazolyl group, a benzthiazolyl group, a naphthothiazolyl group, a m-carbazolyl group, and an azepinyl group.

Examples of the halogen atom include a fluorine atom, a chlorine atom, a bromine atom, and an iodine atom.

Examples of the hydrocarbon group include an alkyl group, an alkenyl group, and an aryl group.

The number of carbon atoms of an alkyl group is preferably 1 to 40. The lower limit is more preferably 3 or greater, even more preferably 5 or greater, still even more preferably 8 or greater, and particularly preferably 10 or greater. An upper limit is more preferably 35 or less and even more preferably 30 or less. The alkyl group may be any one of a linear shape, a branched shape, and a cyclic shape, a linear or branched shape is preferable, and a branched shape is particularly preferable. The number of carbon atoms of a branched alkyl group is preferably 3 to 40. For example, the lower limit is more preferably 5 or greater, even more preferably 8 or greater, and still even more preferably 10 or greater. The upper limit is more preferably 35 or less and even more preferably 30 or less. For example, the number of branches of the branched alkyl group is preferably 2 to 10 and more preferably 2 to 8. If the number of branches is in the range described above, solvent solubility is satisfactory.

The number of carbon atoms of the alkenyl group is preferably 2 to 40. For example, the lower limit thereof is more preferably 3 or greater, even more preferably 5 or greater, still even more preferably 8 or greater, and particularly preferably 10 or greater. The upper limit thereof is more preferably 35 or less and even more preferably 30 or less. The alkenyl group may have any one of a linear shape, a branched shape, and a cyclic shape, but a linear shape or a branched shape is preferable, and a branched shape is particularly preferable. The number of carbon atoms of the branched alkenyl group is preferably 3 to 40. For example, the lower limit is more preferably 5 or greater, even more preferably 8 or greater, and still even more preferably 10 or greater. The upper limit is more preferably 35 or less and even more preferably 30 or less. The number of branches of the branched alkenyl group is preferably 2 to 10 and more preferably 2 to 8. If the number of branches is in the range described above, the solvent solubility is satisfactory.

The number of carbon atoms of the aryl group is preferably 6 to 30, more preferably 6 to 20, and even more preferably 6 to 12.

Examples of the hydrocarbon group including an oxygen atom include a group represented by -L-$R^{x1}$.

L represents —O—, —CO—, —COO—, —OCO—, —(O$R^{x2}$)$_m$—, or —($R^{x2}$O)$_m$—. $R^{x1}$ represents an alkyl group, an alkenyl group, or an aryl group. $R^{x2}$ represents an alkylene group or an arylene group. m represents an integer of 2 or greater, and m items of $R^{x2}$'s may be identical to or different from each other.

L is preferably —O—, —COO—, or —OCO— and more preferably —O—.

An alkyl group, an alkenyl group, or an aryl group that $R^{x1}$ represents has the same meaning as described above, and preferable ranges thereof are also the same. $R^{x1}$ is preferably an alkyl group or an alkenyl group and more preferably an alkyl group.

The number of carbon atoms of the alkylene group represented by $R^{x2}$ is preferably 1 to 20, more preferably 1 to 10, and even more preferably 1 to 5. The alkylene group may have any one of a linear shape, a branched shape, and a cyclic shape, but a linear shape or a branched shape is preferable.

The number of carbon atoms of the arylene group represented by $R^{x2}$ is preferably 6 to 20 and more preferably 6 to 12.

m represents an integer of 2 or greater, preferably represents 2 to 20, and more preferably represents 2 to 10.

As the substituents that $R^1$ and $R^2$ represent, a hydrocarbon group that may include an oxygen atom is preferable or a hydrocarbon group including an oxygen atom is more preferable.

The hydrocarbon group including an oxygen atom is preferably a group represented by —O—$R^{x1}$. $R^{x1}$ is preferably an alkyl group and an alkenyl group, more preferably an alkyl group, and particularly preferably a branched alkyl group. That is, the substituent that $R^1$ and $R^2$ represent is preferably an alkoxy group. If $R^1$ and $R^2$ are alkoxy groups, it is possible to cause the near infrared ray absorption substance having excellent solvent solubility, excellent light fastness, and excellent transparency in a visible region.

The number of carbon atoms of the alkoxy group is preferably 1 to 40. For example, the lower limit is more preferably 3 or greater, even more preferably 5 or greater, still even more preferably 8 or greater, and particularly preferably 10 or greater. The upper limit is more preferably 35 or less and even more preferably 30 or less. The alkoxy group may have any one of a linear shape, a branched shape, and a cyclic shape, a linear or branched shape is preferable, and a branched shape is particularly preferable. The number of carbon atoms of the branched alkoxy group is preferably 3 to 40. For example, the lower limit is more preferably 5 or greater, even more preferably 8 or greater, and still even more preferably 10 or greater. The upper limit is more preferably 35 or less and even more preferably 30 or less. The number of branches of the branched alkoxy group is preferably 2 to 10 and more preferably 2 to 8.

$R^3$ to $R^6$ each independently represent a hydrogen atom or a substituent. Examples of the substituent include an alkyl group, an alkenyl group, an alkynyl group, an aryl group, an heteroaryl group, an amino group (including an alkylamino group, an arylamino group, and a heterocyclic amino group), an alkoxy group, an aryloxy group, a heteroaryloxy group, an acyl group, an alkylcarbonyl group, an arylcarbonyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heteroarylthio group, an alkylsulfonyl group, an arylsulfonyl group, a sulfinyl group, a ureido group, a phosphoric acid amide group, a hydroxyl group, a mercapto group, a halogen atom, a cyano group, a sulfo group, a carboxyl group, a nitro group, a hydroxamic acid group, a sulfino group, a hydrazino group, an imino group, and a silyl group.

$R^3$ to $R^6$ are preferably a combination in which one of $R^3$ and $R^4$ is an electron-withdrawing group, and the other thereof is a heteroaryl group, ne of $R^5$ and $R^6$ is an electron-withdrawing group, and the other thereof is a heteroaryl group.

One of $R^3$ and $R^4$ and one of $R^5$ and $R^6$ are preferably electron-withdrawing groups.

A substituent of which a Hammett σp value (sigma-para value) is positive functions as an electron-withdrawing group.

In this invention, a substituent of which a Hammett σp value is 0.2 or greater can be exemplified as an electron-withdrawing group. A σp value is preferably 0.25 or greater, more preferably 0.3 or greater, and particularly preferably 0.35 or greater. The upper limit is not particularly limited, but preferably 0.80.

Specific examples of the electron-withdrawing group include a cyano group (0.66), a carboxyl group (—COOH:

0.45), an alkoxycarbonyl group (—COOMe: 0.45), an aryloxycarbonyl group (—COOPh: 0.44), a carbamoyl group (—CONH$_2$: 0.36), an alkylcarbonyl group (—COMe: 0.50), an arylcarbonyl group (—COPh: 0.43), an alkylsulfonyl group (—SO$_2$Me: 0.72), or an arylsulfonyl group (—SO$_2$Ph: 0.68). Particularly preferably, an example is a cyano group. Here, Me represents a methyl group, and Ph represents a phenyl group.

With respect to a Hammett σp value, paragraphs 0024 and 0025 of JP2009-263614A are referred to, and the contents thereof are incorporated to this specification.

One of $R^3$ and $R^4$ and one of $R^5$ and $R^6$ preferably represent a heteroaryl group.

The heteroaryl group is preferably a monocyclic ring or a fused ring, is preferably a monocyclic ring or a fused ring having a fused number of 2 to 8, and more preferably a monocyclic ring or a fused ring having a fused number of 2 to 4. The number of hetero atoms that form a heteroaryl group is preferably 1 to 3. The hetero atom that forms a heteroaryl group is preferably a nitrogen atom, an oxygen atom, or a sulfur atom. The number of carbon atoms of a heteroaryl group is preferably 3 to 30, more preferably 3 to 18, more preferably 3 to 12, and particularly preferably 3 to 5. The heteroaryl group is preferably a 5-membered or 6-membered ring. Specific examples of a heteroaryl group include heteroaryl groups exemplified in $R^1$ and $R^2$ and preferably include a pyridyl group, a pyrimidyl group, a triazyl group, a quinolyl group, a quinoxalyl group, an isoquinolyl group, an indolenyl group, a benzoxazolyl group, and a benzthiazolyl group.

The heteroaryl group may include a substituent and may be unsubstituted. Examples of the substituent include an alkyl group, an alkenyl group, an alkynyl group, an aryl group, an amino group (including an alkylamino group, an arylamino group, and a heterocyclic amino group), an alkoxy group, an aryloxy group, an acyl group, an alkylcarbonyl group, an arylcarbonyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heteroarylthio group, a sulfonyl group, an alkylsulfonyl group, an arylsulfonyl group, a sulfinyl group, a ureido group, a phosphoric acid amide group, a hydroxyl group, a mercapto group, a halogen atom, a cyano group, a sulfo group, a carboxyl group, a nitro group, a hydroxamic acid group, a sulfino group, a hydrazino group, an imino group, and a silyl group. A halogen atom, an alkyl group, and an alkoxy group are preferable.

As the halogen atom, a fluorine atom, a chlorine atom, a bromine atom, and an iodine atom are preferable, and a chlorine atom is particularly preferable.

The number of carbon atoms of the alkyl group is preferably 1 to 40, more preferably 1 to 30, and particularly preferably 1 to 25. The alkyl group may have any one of a linear shape, a branched shape, and a cyclic shape, but a linear shape or a branched shape is preferable, and a linear shape is particularly preferable.

The number of carbon atoms of the alkoxy group is preferably 1 to 40, more preferably 1 to 30, and particularly preferably 1 to 25. The alkoxy group may have any one of a linear shape, a branched shape, and a cyclic shape, but a linear shape or a branched shape is preferable, and a linear shape is particularly preferable.

$R^3$ and $R^4$, and $R^5$ and $R^6$ are respectively bonded to each other to form rings.

In a case where $R^3$ and $R^4$, and $R^5$ and $R^6$ are respectively bonded to each other to form rings, it is preferable to form a 5-membered to 7-membered ring (preferably 5-membered or 6-membered ring). It is preferable that the formed ring is used as acidic nucleus in a merocyanine coloring agent. Specific examples thereof include the followings.

(a) 1,3-dicarbonyl ring: for example, 1,3-indandione, 1,3-cyclohexanedione, 5,5-dimethyl-1,3-cyclohexanedione, and 1,3-dioxane-4,6-dione.

(b) Pyrazolinone ring: for example, 1-phenyl-2-pyrazolin-5-one, 3-methyl-1-phenyl-2-pyrazolin-5-one, and 1-(2-benzothiazoyl)-3-methyl-2-pyrazolin-5-one.

(c) Isoxazolinone ring: for example, 3-phenyl-2-isoxazolin-5-one, and 3-methyl-2-isoxazolin-5-one.

(d) Oxindole ring: for example, 1-alkyl-2,3-dihydro-2-oxindole.

(e) 2,4,6-triketohexahydropyrimidine ring: for example, barbituric acid or 2-thiobarbituric acid and derivatives thereof. Examples of the derivatives include a 1-alkyl product such as 1-methyl and 1-ethyl, a 1,3-dialkyl product such as 1,3-dimethyl, 1,3-diethyl, and 1,3-dibutyl, a 1,3-diaryl product such as 1,3-diphenyl, 1,3-di(p-chlorophenyl), 1,3-di(p-ethoxycarbonyl phenyl), a 1-alkyl-1-aryl product such as 1-ethyl-3-phenyl, and a 1,3-position diheterocyclic substitution product such as 1,3-di(2-pyridyl).

(f) 2-thio-2,4-thiazolidinedione ring: for example, rhodanine and derivatives thereof. Examples of the derivatives include 3-alkyl rhodanine such as 3-methyl rhodanine, 3-ethyl rhodanine, and 3-allyl rhodanine, 3-aryl rhodanine such as 3-phenyl rhodanine, and 3-position heterocyclic substituted rhodanine such as 3-(2-pyridyl) rhodanine.

(g) 2-thio-2,4-oxazolidinedione (2-thio-2,4-(3H, 5H)-oxazole dione ring: for example, 3-ethyl-2-thio-2,4-oxazolidinedi one.

(h) Thianaphthenone ring: for example, 3(2H)-thianaphthenone-1,1-dioxide.

(i) 2-thio-2,5-thiazolidinedione ring: for example, 3-ethyl-2-thio-2,5-thiazodinedione.

(j) 2,4-thiazodinedione ring: for example 2,4-thiazolidinedione, 3-ethyl-2,4-thiazolidinedione, and 3-phenyl-2,4-thiazolidinedione.

(k) Thiazolin-4-one ring: for example, 4-thiazolinone and 2-ethyl-4-thiazolinone.

(l) 4-thiazolidinone ring: for example, 2-ethylmercapto-5-thiazolin-4-one and 2-alkylphenylamino-5-thiazolin-4-one.

(m) 2,4-imidazolidinedione (hydantoin) ring: for example, 2,4-imidazolidinedione and 3-ethyl-2,4-imidazolidinedione.

(n) 2-thio-2,4-imidazolidinedione (2-thiohydantoin) ring: for example, 2-thio-2,4-imidazolidinedione and 3-ethyl-2-thio-2,4-imidazolidinedione.

(o) Imidazolin-5-one ring: for example, 2-propylmercapto-2-imidazolin-5-one.

(p) 3,5-pyrazolidinedione ring: for example, 1,2-diphenyl-3,5-pyrazolidinedione and 1,2-dimethyl-3,5-pyrazolidinedione.

(q) Benzothiophen-3-one ring: for example, benzothiophen-3-one, oxobenzothiophen-3-one, and dioxobenzothiophen-3-one.

(r) Indanone ring: for example, 1-indanone, 3-phenyl-1-indanone, 3-methyl-1-indanone, 3,3-diphenyl-1-indanone, and 3,3-dimethyl-1-indanone.

Examples of the ring that is formed by bonding $R^3$ and $R^4$, and $R^5$ and $R^6$ to each other preferably include a 1,3-dicarbonyl ring, a pyrazolinone ring, a 2,4,6-triketohexahydropyrimidine ring (including a thioketone product), a 2-thio-2,4-thiazolidinedione ring, a 2-thio-2,4-oxazolidinedione ring, a 2-thio-2,5-thiazolidinedione ring, a 2,4-thiazolidinedione ring, a 2,4-imidazolidinedione ring, a 2-thio-2,4-imidazolidinedione ring, a 2-imidazolin-5-one ring, a 3,5-pyrazolidinedione ring, a benzothiophen-3-one ring, and an indanone ring and more preferably include a 1,3-dicarbonyl ring, a 2,4,6-triketohexahydropyrimidine ring (including a thioketone product), a 3,5-pyrazolidinedione ring, a benzothiophen-3-one ring, and an indanone ring.

In a case where $R^3$ and $R^4$, and $R^5$ and $R^6$ are respectively bonded to each other to form rings, σp values of $R^3$ to $R^6$ are not defined. However, σp values in a case of ring formation are defined in an assumption that partial structures of respective rings are substituted with $R^3$ to $R^6$. For example, in a case where $R^3$ and $R^4$ are bonded to each other to form a 1,3-indandione ring, it is considered that benzoyl groups are respectively substituted with $R^3$ and $R^4$.

$X^1$ and $X^2$ each independently represent a hydrogen atom or a substituent.

Examples of the substituent include an alkyl group, an alkoxy group, an aryl group, a heteroaryl group, a metal atom, a group represented by $-BR^{21}R^{22}$, and a group represented by Formula (2-4) described below.

The number of carbon atoms of the alkyl group is preferably 1 to 40. For example, the lower limit is more preferably 3 or greater. For example, the upper limit is more preferably 30 or less and even more preferably 25 or less. The alkyl group may have any one of a linear shape, a branched shape, and a cyclic shape, a linear or branched shape is preferable, and a linear shape is particularly preferable.

The number of carbon atoms of the alkoxy group is preferably 1 to 40. For example, the lower limit is more preferably 3 or greater. For example, the upper limit is more preferably 30 or less and even more preferably 25 or less.

The alkoxy group may have any one of a linear shape, a branched shape, and a cyclic shape, a linear or branched shape is preferable, and a linear shape is particularly preferable.

The number of carbon atoms of the aryl group is preferably 6 to 20 and more preferably 6 to 12. As the aryl group, a phenyl group is preferable.

The heteroaryl group may be a monocyclic ring or may be a polycyclic ring, and preferably a monocyclic ring. The number of hetero atoms that form a heteroaryl group is preferably 1 to 3. A hetero atom that forms a heteroaryl group is preferably a nitrogen atom, an oxygen atom, or a sulfur atom. The number of carbon atoms of a heteroaryl group is preferably 3 to 30, more preferably 3 to 18, more preferably 3 to 12, and particularly preferably 3 to 5. The heteroaryl group is preferably a 5-membered or 6-membered ring. Specific examples of the heteroaryl group include those described in $R^1$ and $R^2$.

As the metal atom, magnesium, aluminum, calcium, barium, zinc, tin, vanadium, iron, cobalt, nickel, copper, palladium, iridium, and platinum are preferable, and aluminum, zinc, vanadium, iron, copper, palladium, iridium, and platinum are particularly preferable.

As $X^1$ and $X^2$, a hydrogen atom or $-BR^{21}R^{22}$ is more preferable, and $-BR^{21}R^{22}$ is still even more preferable.

$R^{21}$ and $R^{22}$ each independently represent a substituent, and $R^{21}$ and $R^{22}$ may be bonded to each other to form a ring.

As substituents represented by $R^{21}$ and $R^{22}$, a halogen atom, an alkyl group, an alkoxy group, an aryl group, a heteroaryl group, or a group represented by Formula (2-4) below is preferable, a halogen atom, or an aryl group is more preferable, and an aryl group is even more preferable.

As the halogen atom, a fluorine atom, a chlorine atom, a bromine atom, and an iodine atom are preferable, and a fluorine atom is particularly preferable. Examples of an alkyl group, an alkoxy group, an aryl group, and a heteroaryl group include groups exemplified in $X^1$ and $X^2$, and preferable ranges thereof are also the same.

(2-4)

In Formula (2-4), $R^{a5}$ to $R^{a9}$ each independently represent a hydrogen atom or a substituent. * represent a coupler hand with Formula (1). Examples of the substituents that $R^{a5}$ to $R^{a9}$ represent include an alkyl group, an alkoxy group, an aryl group, and a heteroaryl group, and an alkyl group is preferable.

$R^{21}$ and $R^{22}$ may be bonded to each other to form a ring. Examples of the ring formed by bonding $R^{21}$ and $R^{22}$ to each other include structures represented by (2-1) to (2-3) below. As described below, R represents a substituent, $R^{a1}$ to $R^{a4}$ each independently represent a hydrogen atom or a substituent, and m1 to m3 each independently represent an integer of 0 to 4. Examples of the substituents represented by R and $R^{a1}$ to $R^{a4}$ include substituents exemplified in $R^{21}$ and $R^{22}$, and an alkyl group is preferable.

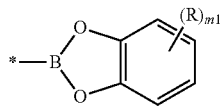

(2-1)

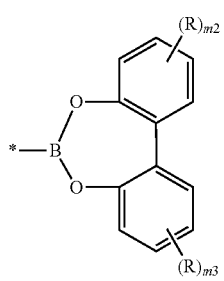

(2-2)

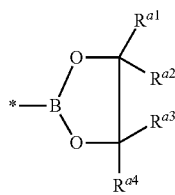

(2-3)

The compound represented by Formula (1) is preferably a compound represented by Formula (1A) below.

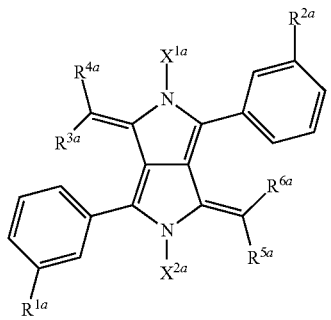

(1A)

In Formula (1A), $R^{1a}$ and $R^{2a}$ each independently represent a substituent, $R^{3a}$ to $R^{6a}$ each independently represent a hydrogen atom or a substituent, $R^{3a}$ and $R^{4a}$, and $R^{5a}$ and $R^{6a}$ are respectively bonded to each other to form rings, $X^{1a}$ and $X^{2a}$ each independently represent a hydrogen atom or —$BR^{21a}R^{22a}$, $R^{21a}$ and $R^{22a}$ each independently represent substituents, and $R^{21a}$ and $R^{22a}$ are bonded to each other to form a ring.

$R^{1a}$ to $R^{6a}$, $X^{1a}$, $X^{2a}$, $R^{21a}$, and $R^{22a}$ respectively have the same meaning as $R^1$ to $R^6$, $X^1$, $X^2$, $R^{21}$, and $R^{22}$ described above, and preferable ranges thereof are also the same.

The compound represented by Formula (1) is preferably a compound represented by Formula (1B) below.

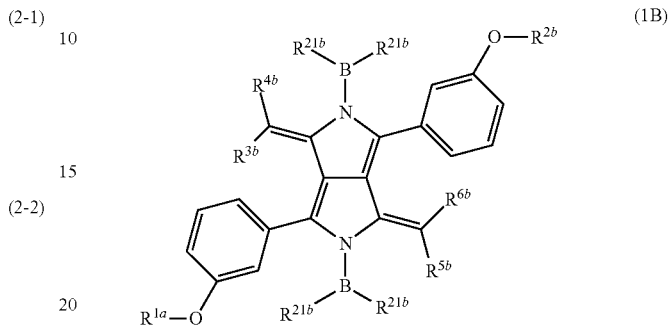

(1B)

In Formula (1B), $R^{1b}$ and $R^{2b}$ each independently represent a branched alkyl group, $R^{3b}$ to $R^{6b}$ each independently represent a hydrogen atom or a substituent, $R^{3b}$ and $R^{4b}$, and $R^{5b}$ and $R^{6b}$ may respectively be bonded to each other to form rings, $R^{21b}$ and $R^{22b}$ each independently represent a substituent, and $R^{21b}$ and $R^{22b}$ are bonded to each other to form a ring.

$R^{1b}$ and $R^{2b}$ each independently represent a branched alkyl group. The number of carbon atoms is preferably 3 to 40. For example, the lower limit is more preferably 5 or greater, even more preferably 8 or greater, and still even more preferably 10 or greater. The upper limit is more preferably 35 or less and even more preferably 30 or less. The number of branches of the branched alkyl group is preferably 2 to 10 and more preferably 2 to 8.

$R^{3b}$ to $R^{6b}$, $R^{21b}$, and $R^{22b}$ are respectively the same as $R^3$ to $R^6$, $R^{21}$, and $R^{22}$ described above and preferable ranges thereof are also the same.

That is, $R^{3b}$ to $R^{6b}$ preferably has a combination in which one of $R^{3b}$ and $R^{4b}$ is an electron-withdrawing group, and the other one is a heteroaryl group, and one of $R^{5b}$ and $R^{6b}$ is an electron-withdrawing group, and the other one is a heteroaryl group. The electron-withdrawing group is preferably a cyano group.

$R^{21b}$ and $R^{22b}$ each independently represent preferably a halogen atom, an alkyl group, an alkoxy group, an aryl group, or a heteroaryl group, more preferably a halogen atom, or an aryl group, and even more preferably an aryl group.

Specific examples of the near infrared ray absorption substance according to the invention are as below. Among the compounds provided below, compounds D-1 to D-24, and D-28 to D-90 are compounds represented by Formula (1).

In structural formulae below, "i" as in i-$C_{10}H_{21}$ and the like represents a branch. Bu represents a butyl group and Ph represents a phenyl group.

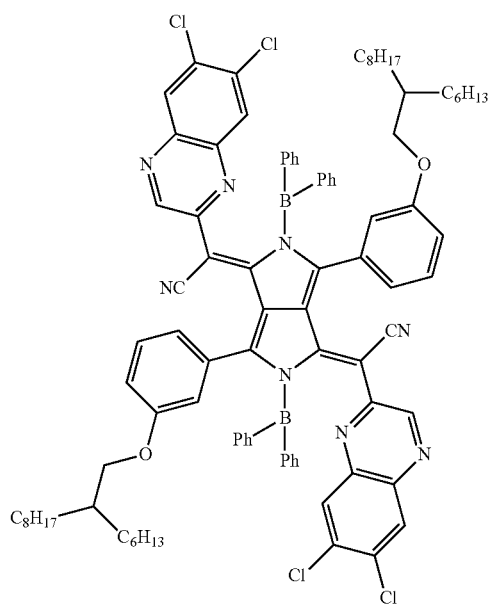
D-1
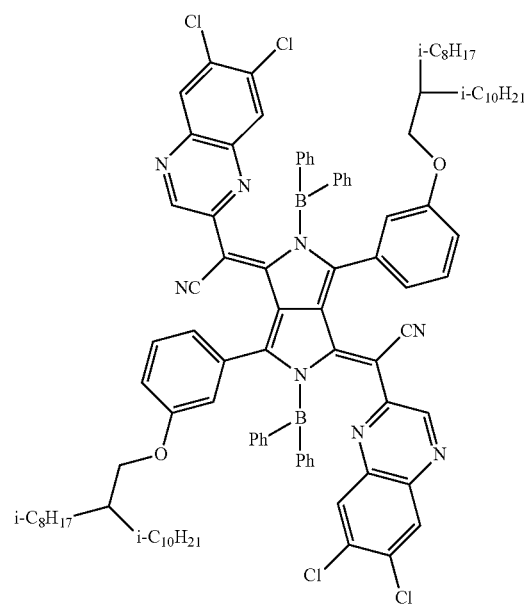
D-2
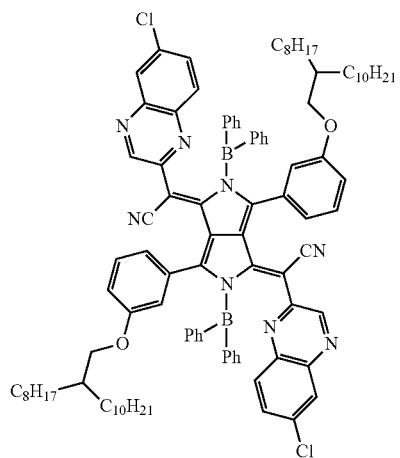
D-3
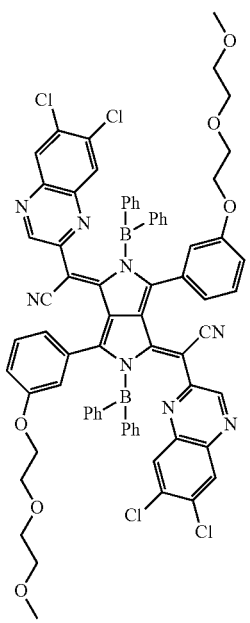
D-4

-continued
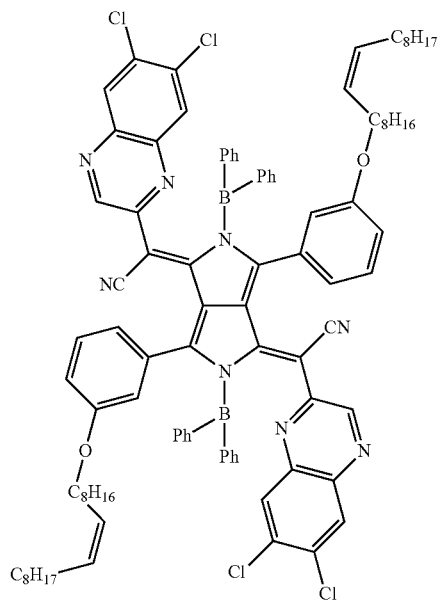
D-5
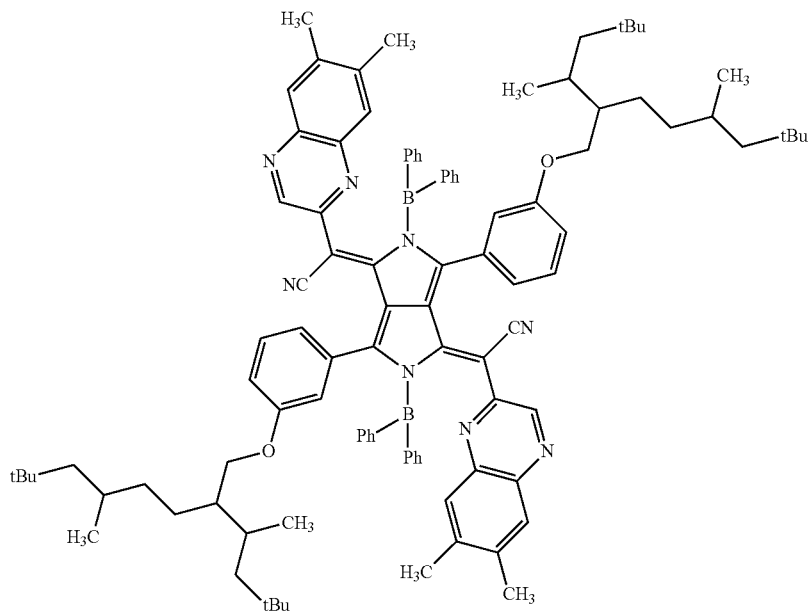
D-6

-continued
D-7
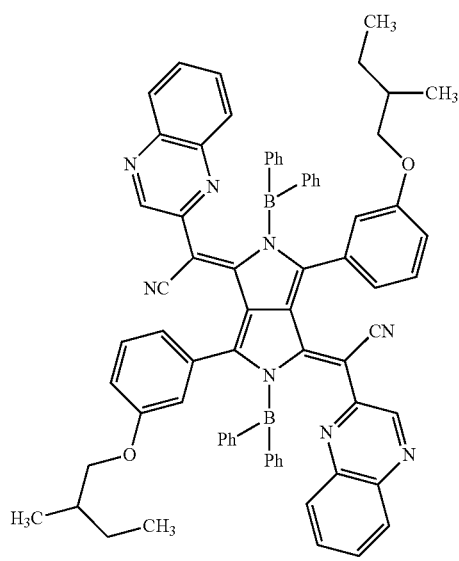
D-8
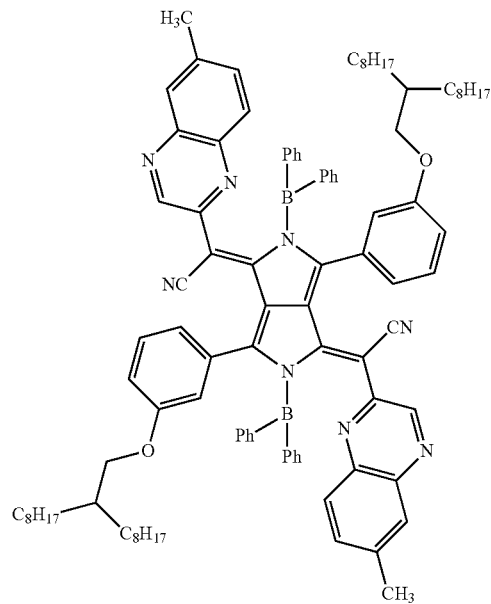
D-9
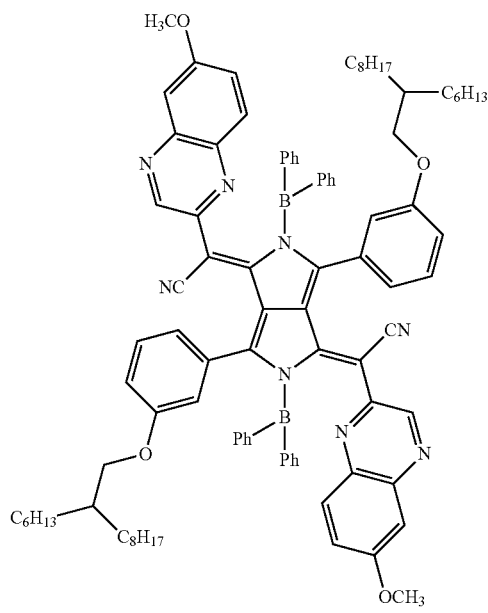
D-10
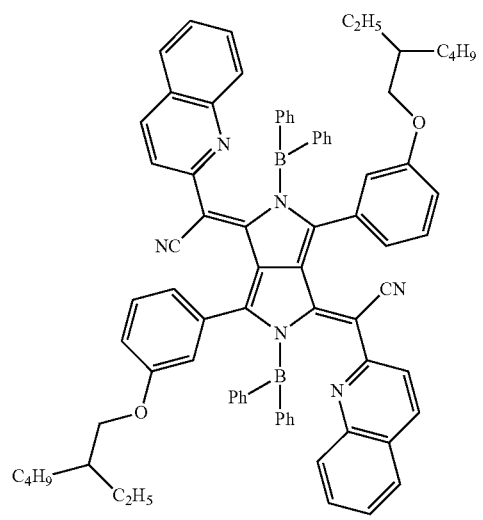

-continued
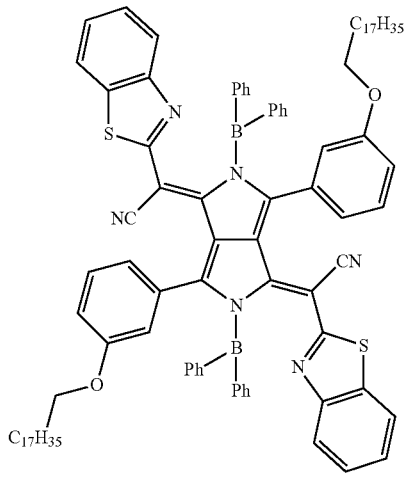
D-11
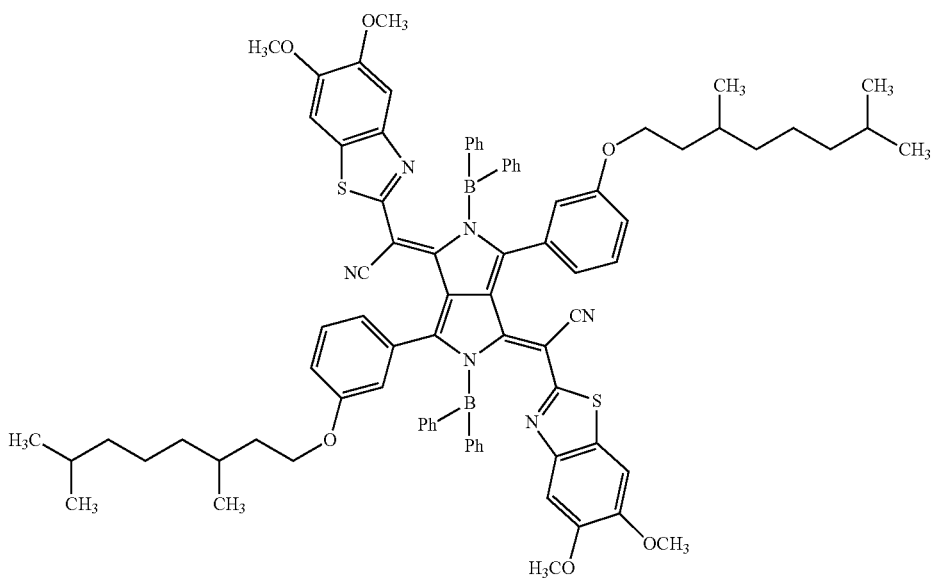
D-12
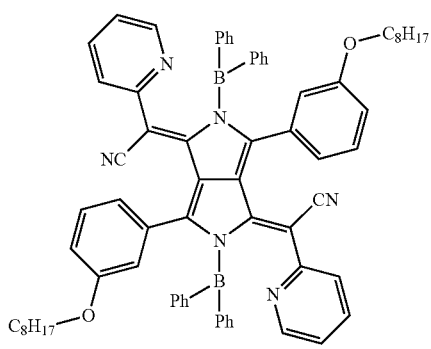
D-13
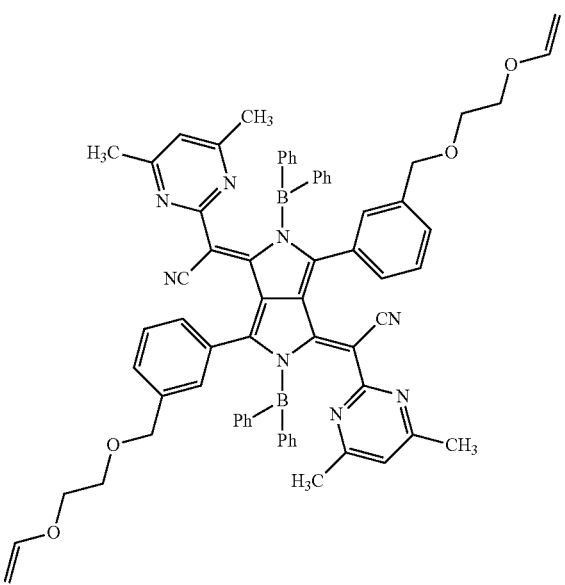
D-14

-continued
D-15
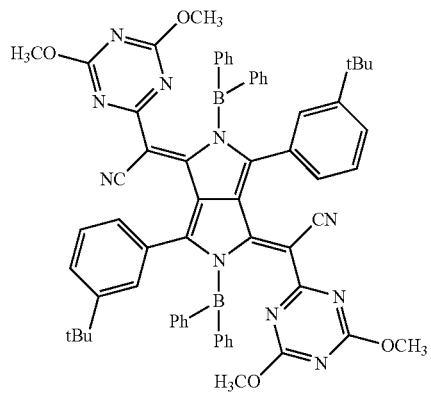
D-16
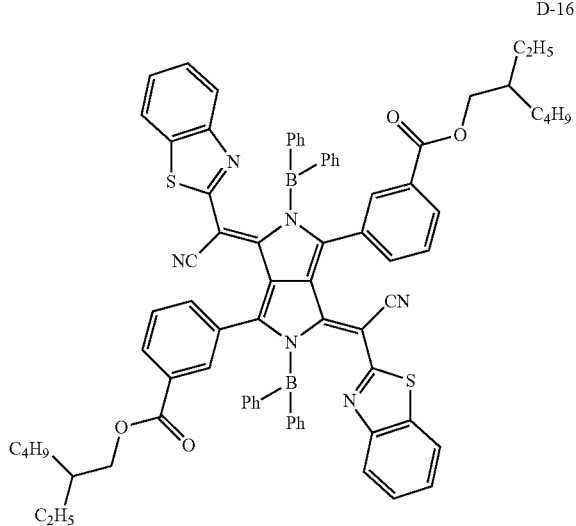
D-17
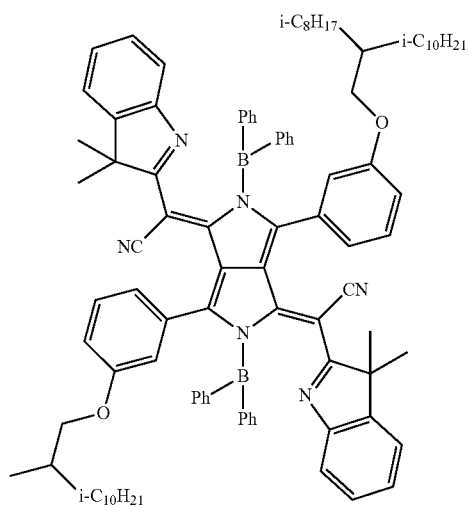
D-18
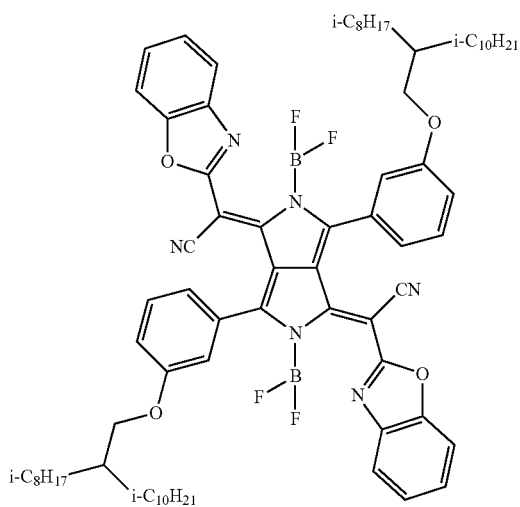
D-19
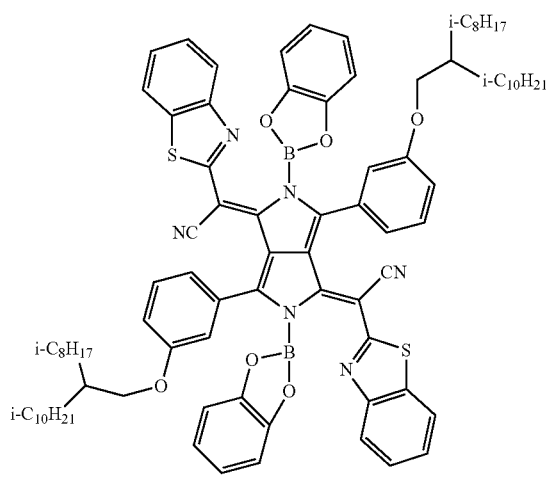
D-20
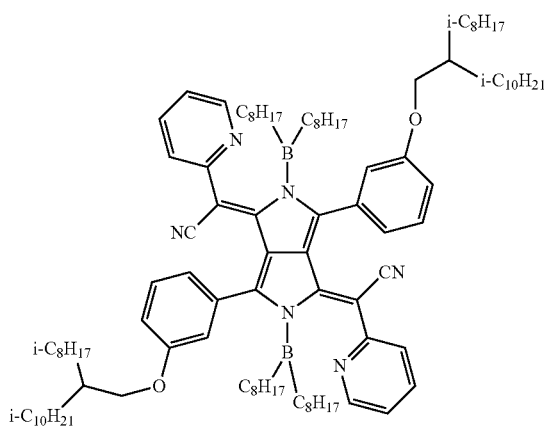

-continued
D-21
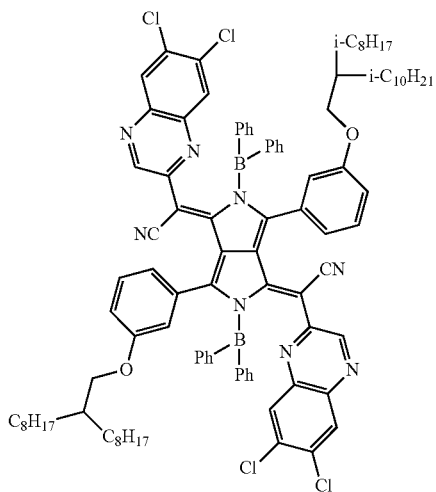
D-22
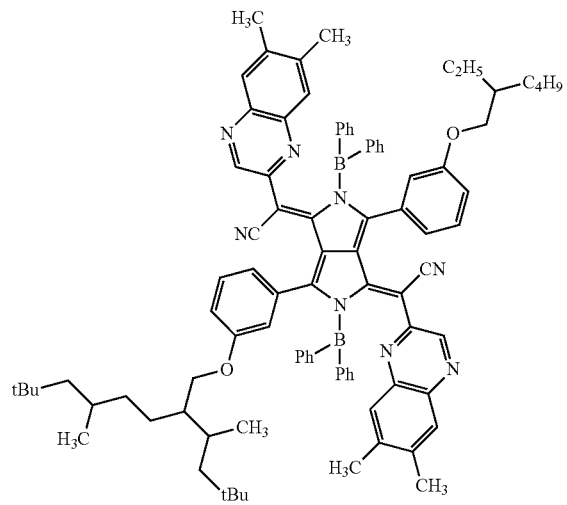
D-23
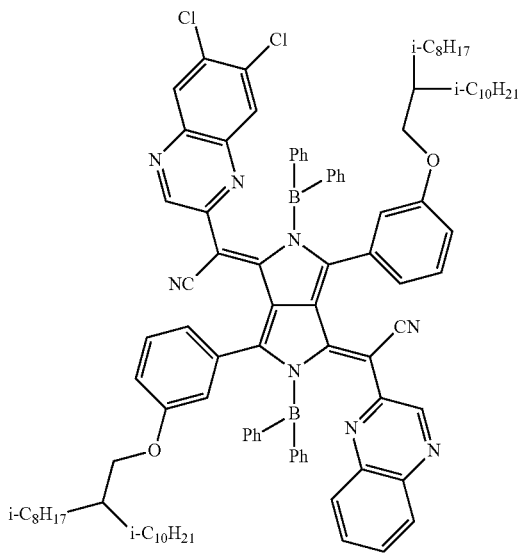
D-24
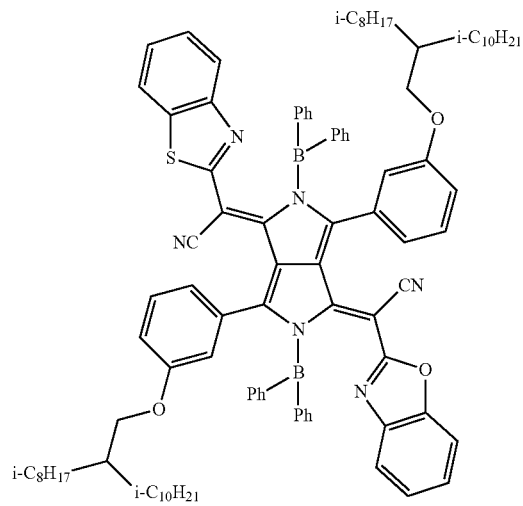
D-25
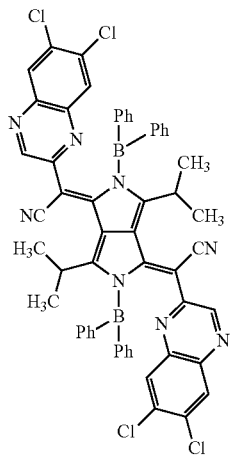
D-26
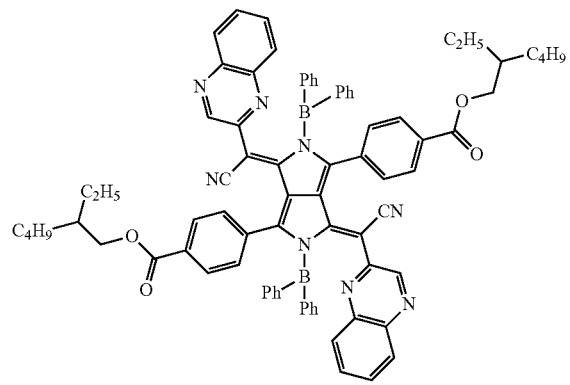

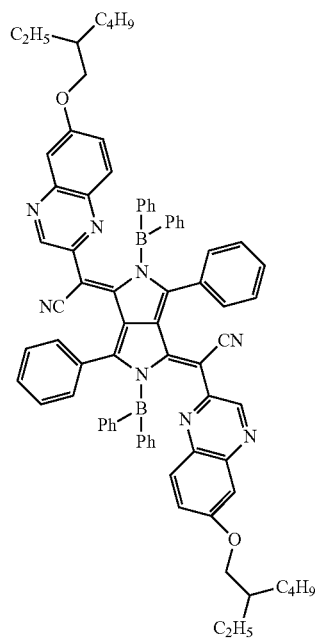
D-27
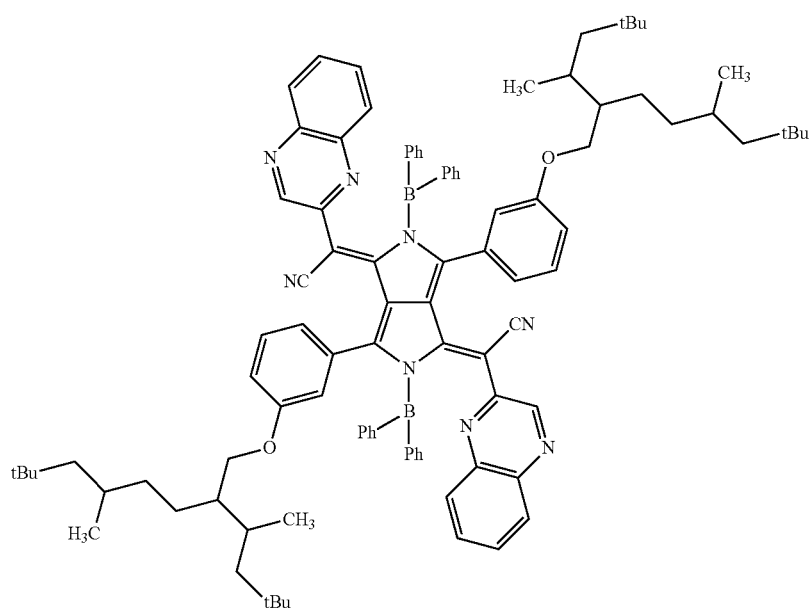
D-28

-continued
D-29
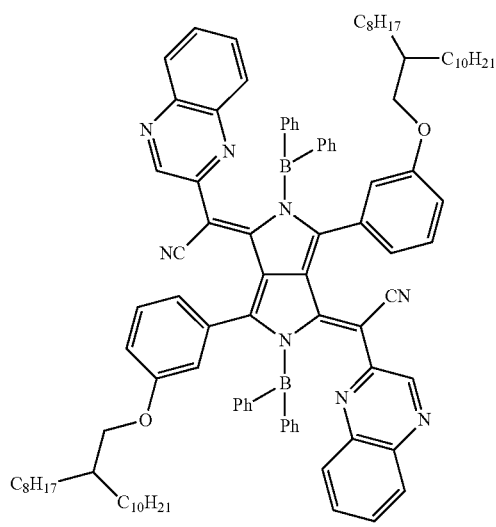
D-30
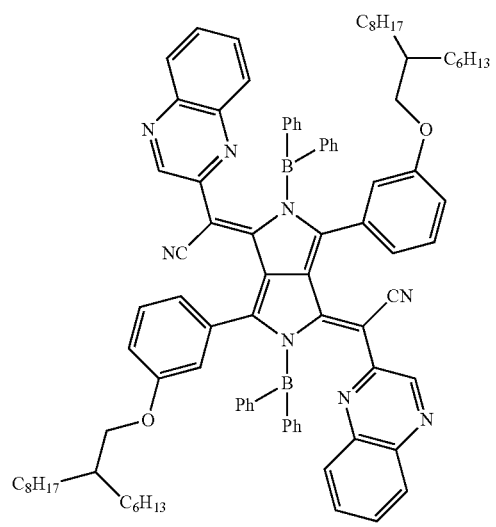
D-31
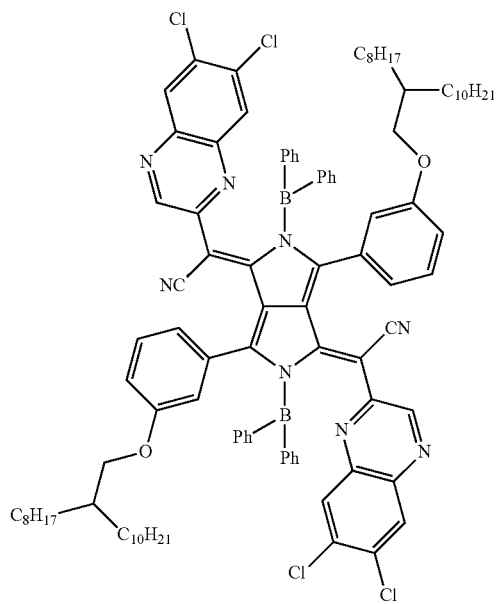

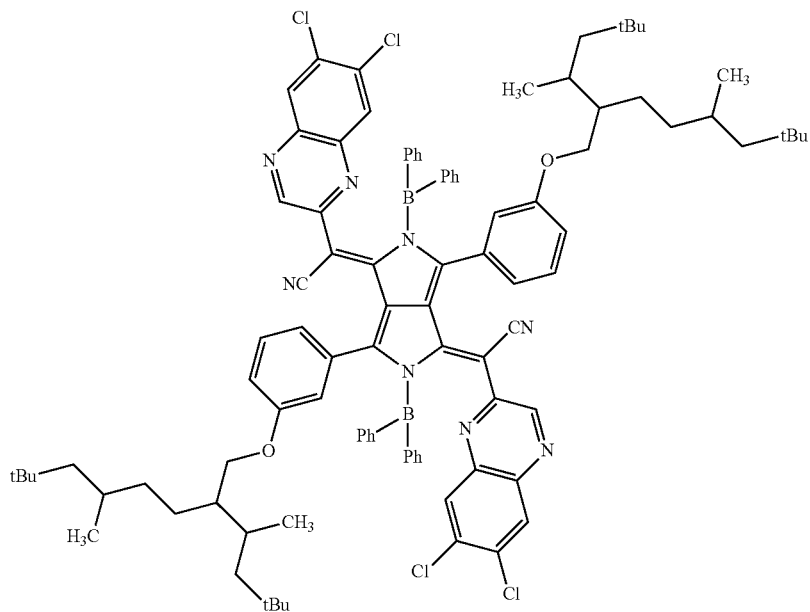
D-32
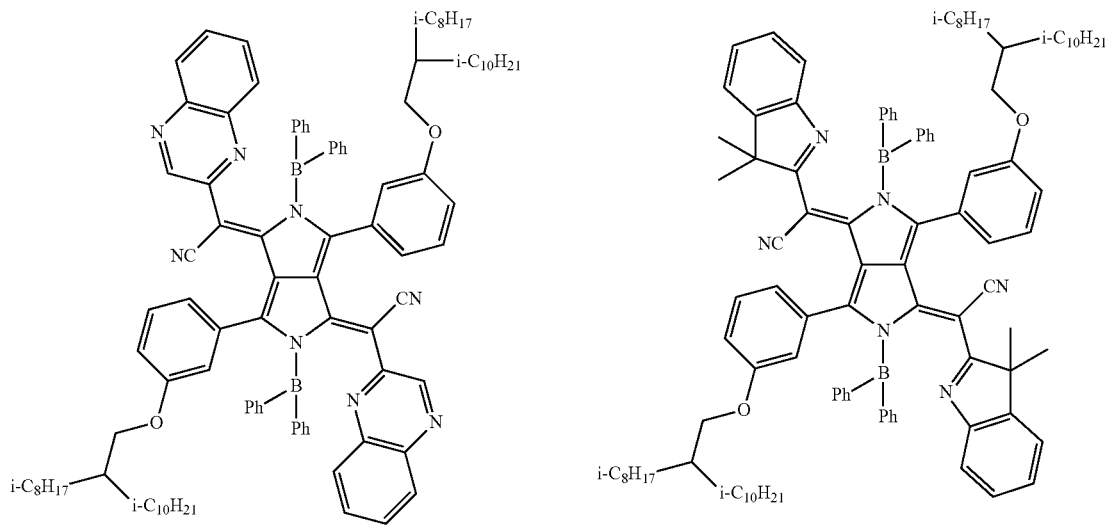
D-33
D-34

-continued
D-35
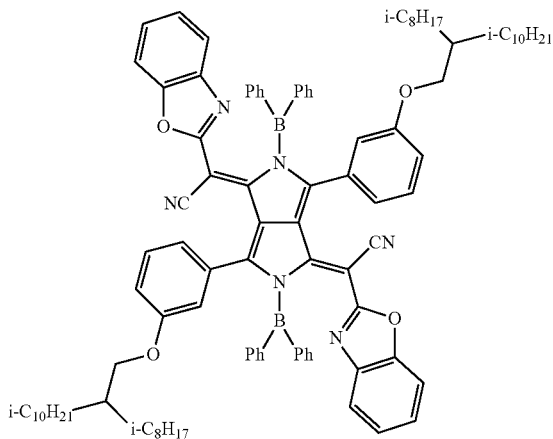
D-36
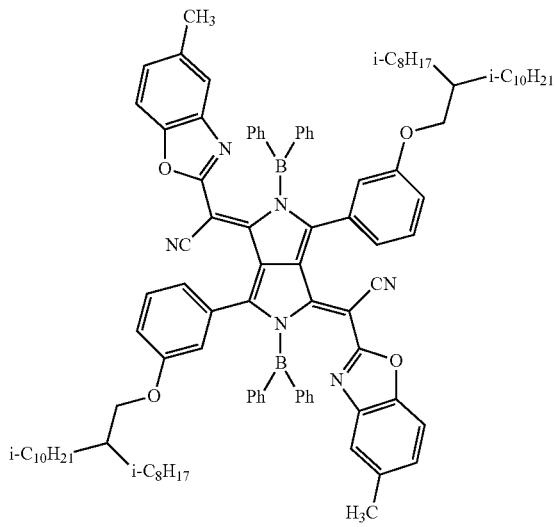
D-37
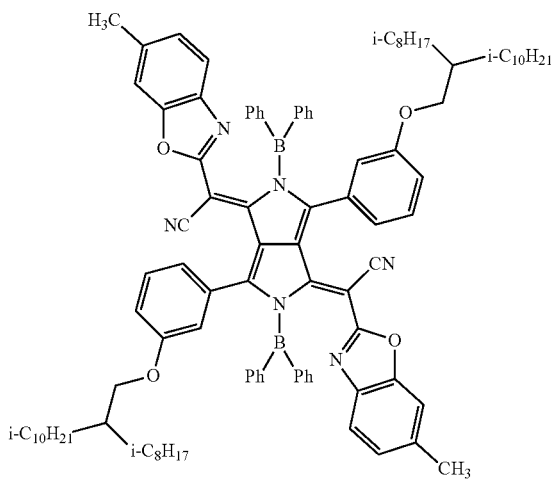
D-38
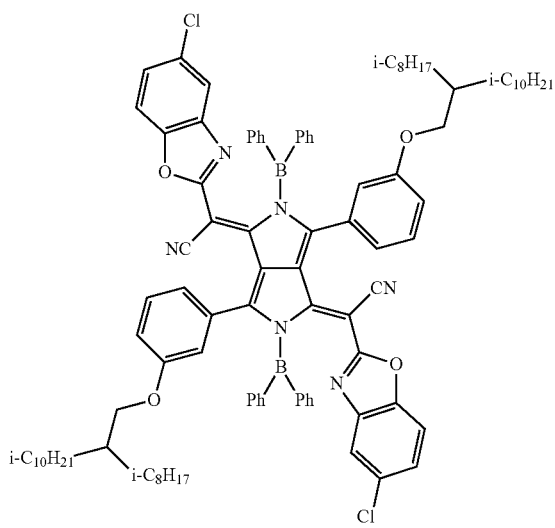
D-39
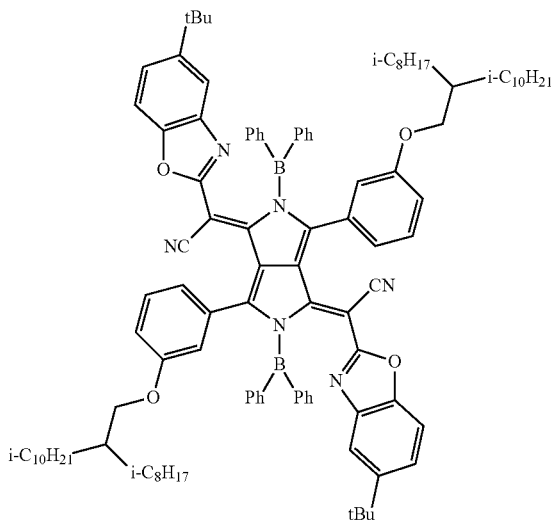
D-40
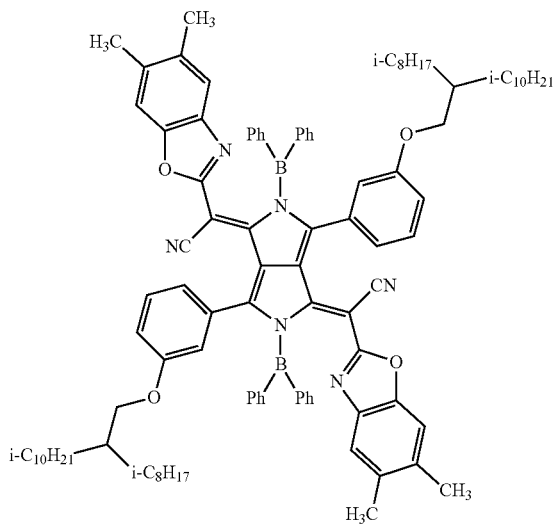

-continued
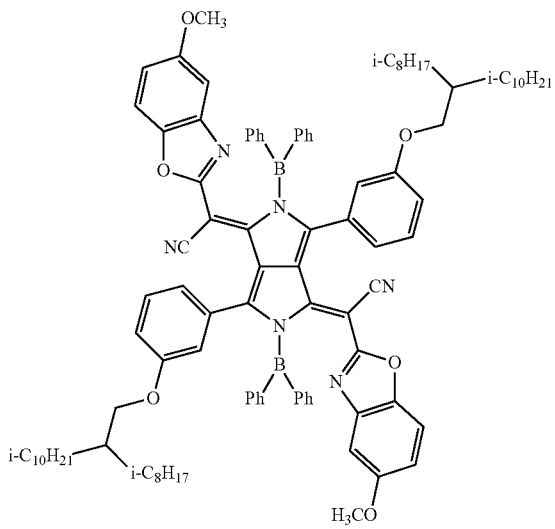
D-41
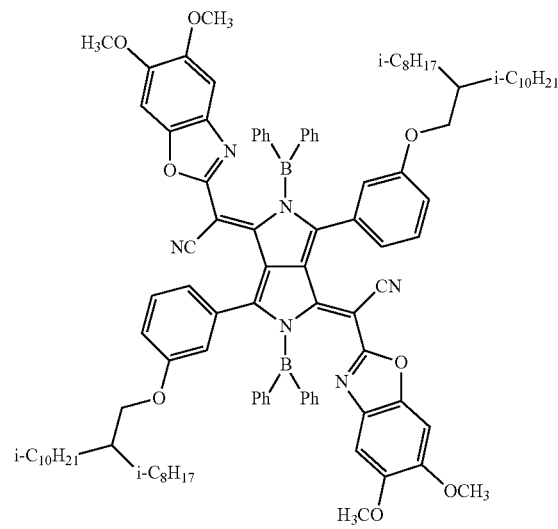
D-42
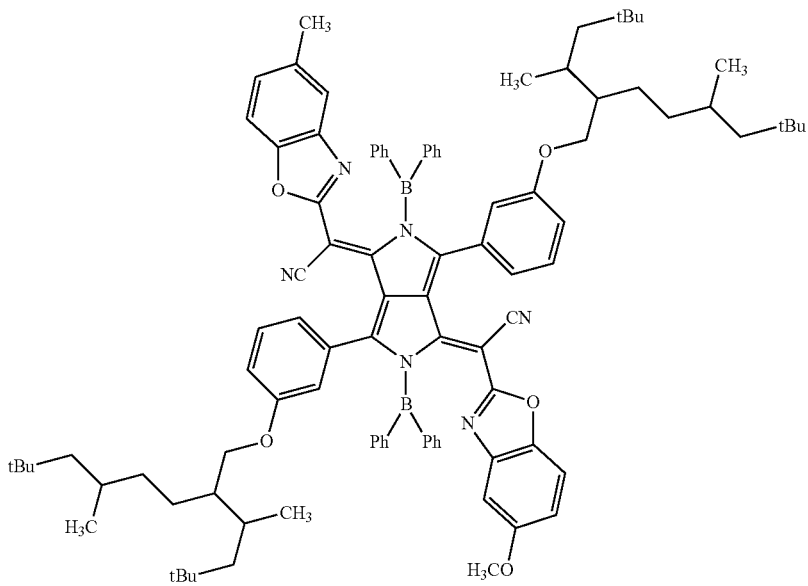
D-43
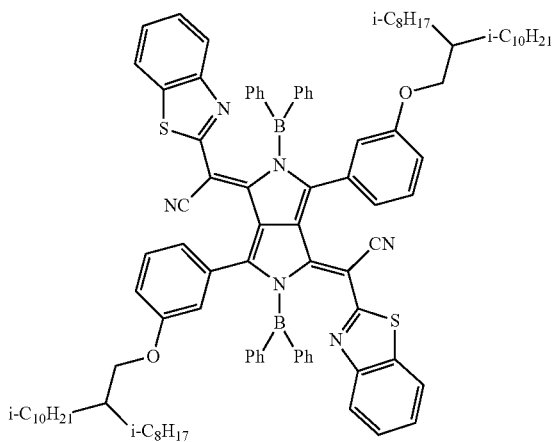
D-44
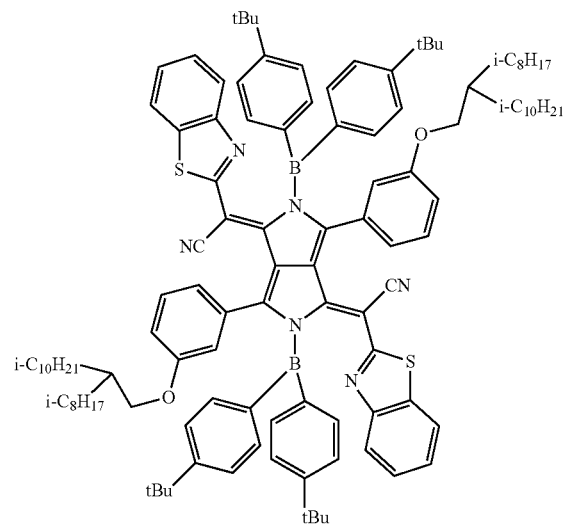
D-45

-continued
D-46
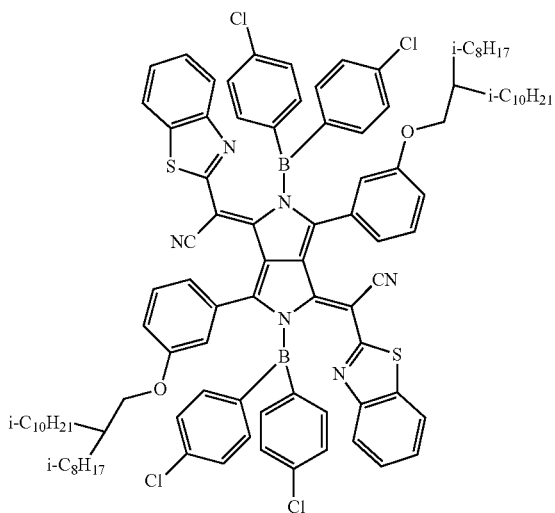
D-47
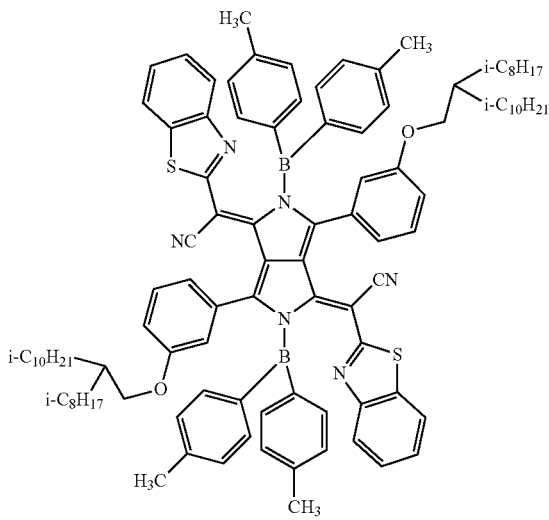
D-48
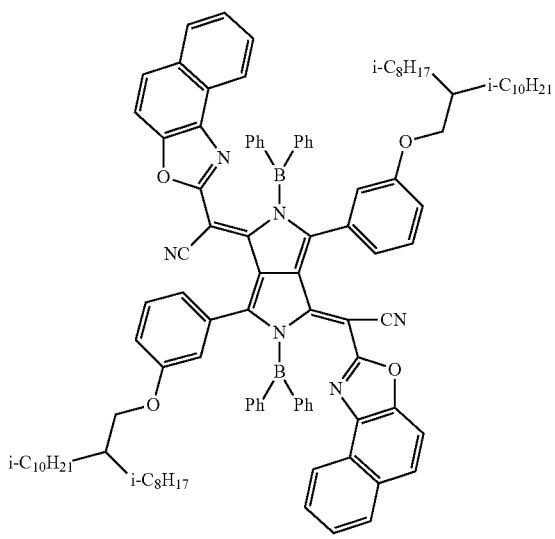
D-49
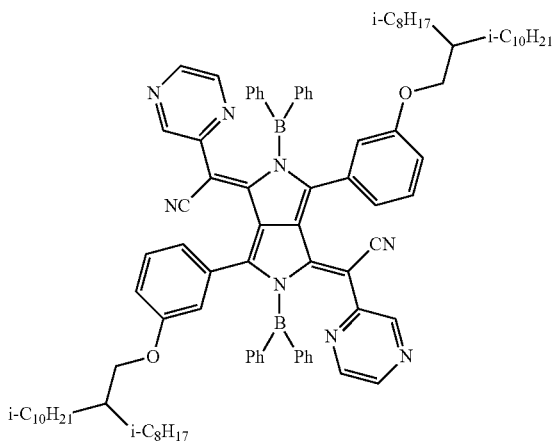
D-50
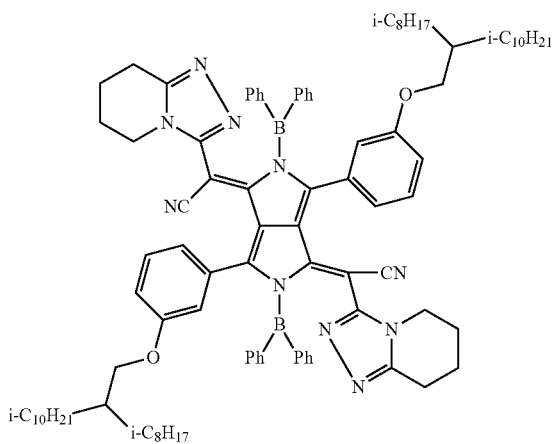
D-51
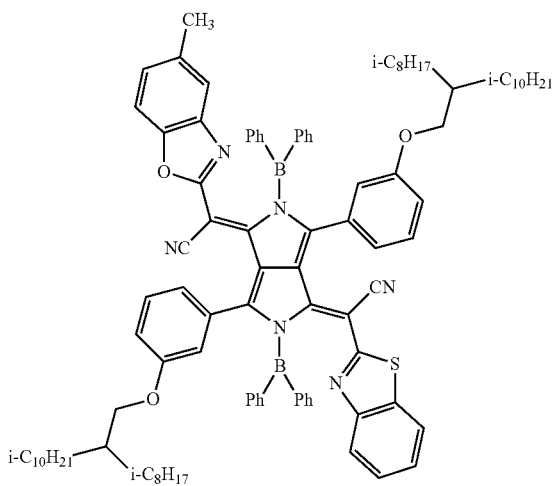

-continued
D-52
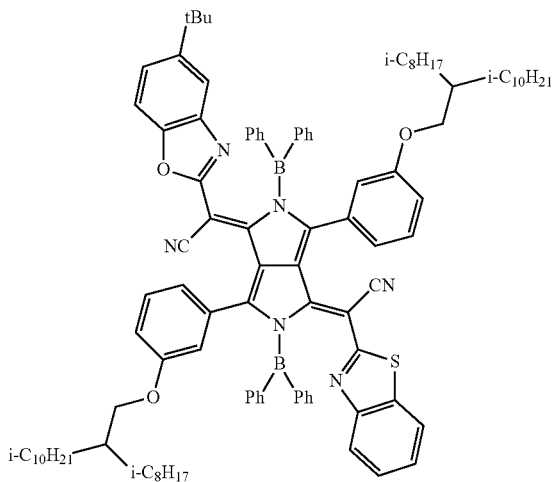
D-53
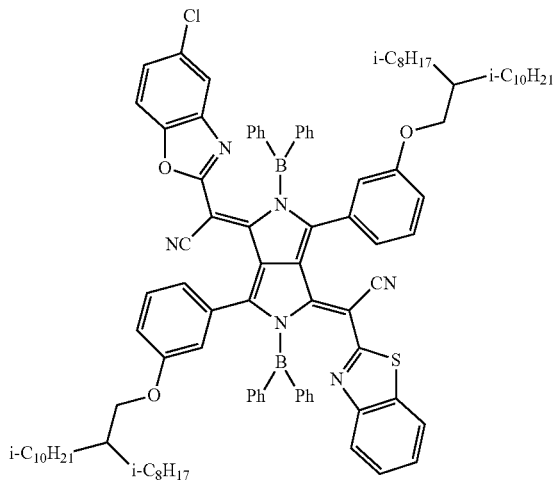
D-54
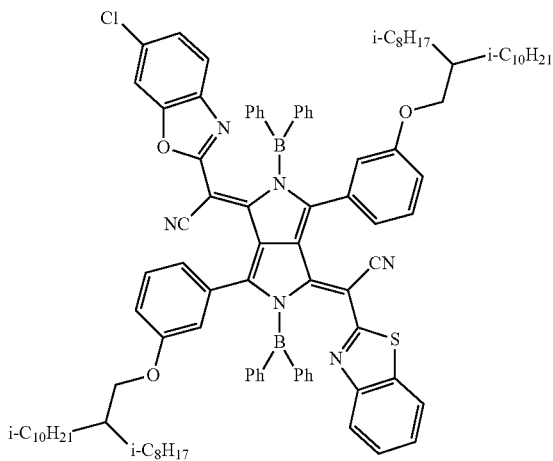
D-55
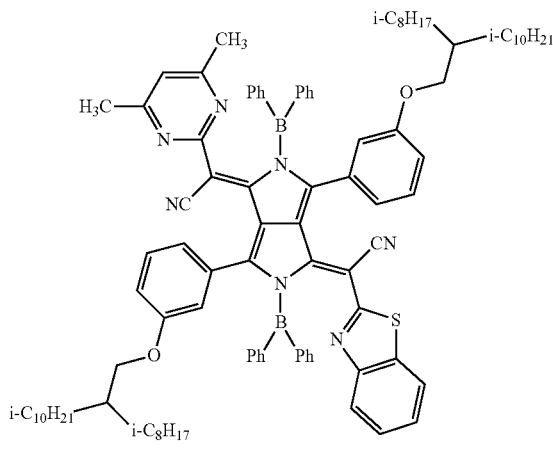
D-56
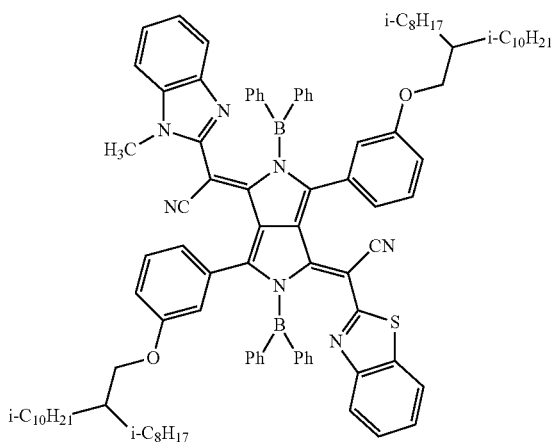
D-57
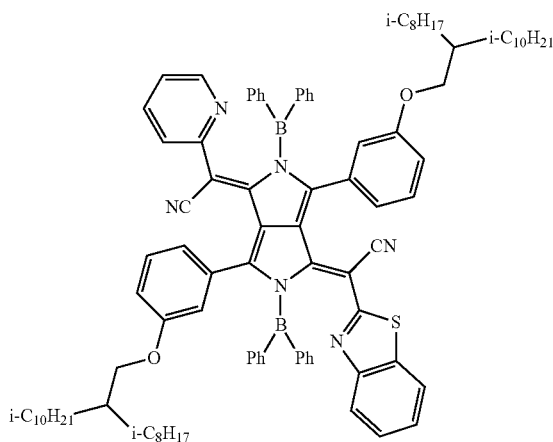

-continued
D-58
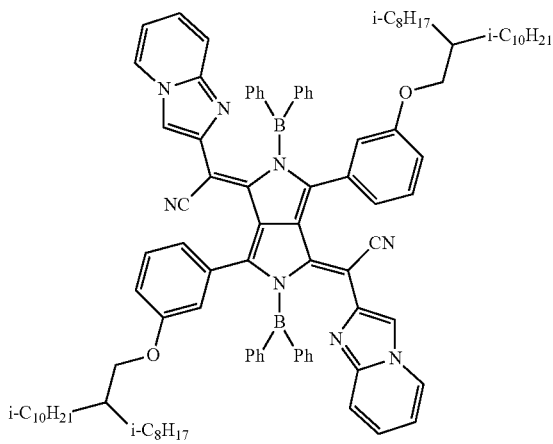
D-59
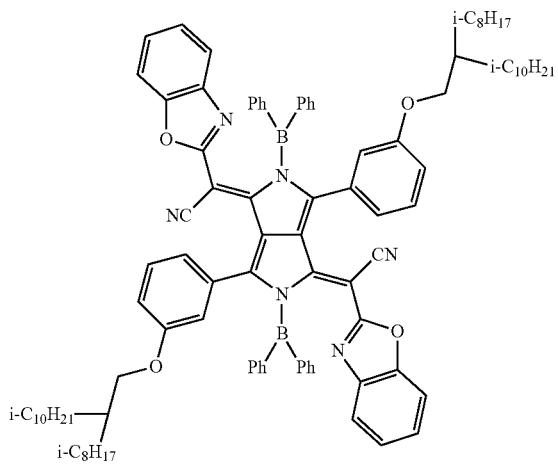
D-60
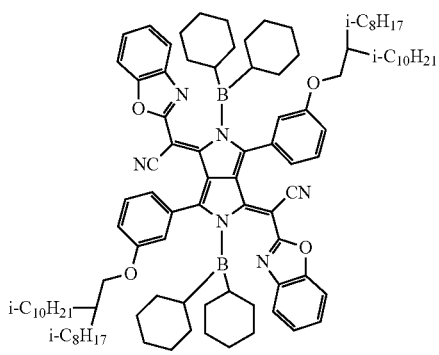
D-61
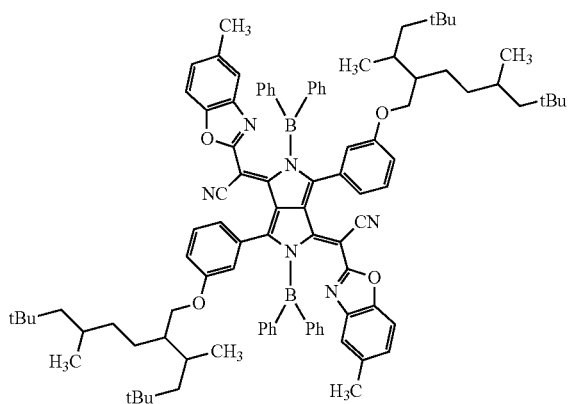
D-62
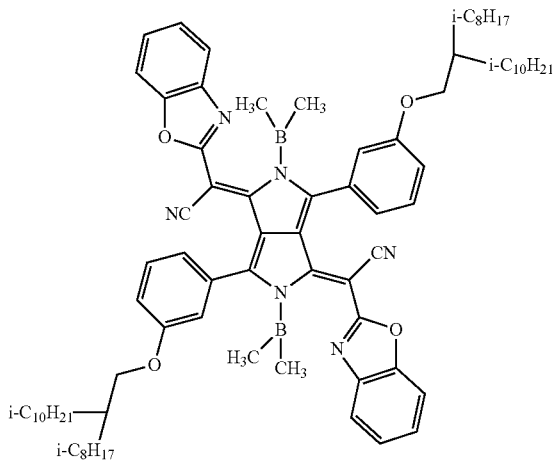
D-63
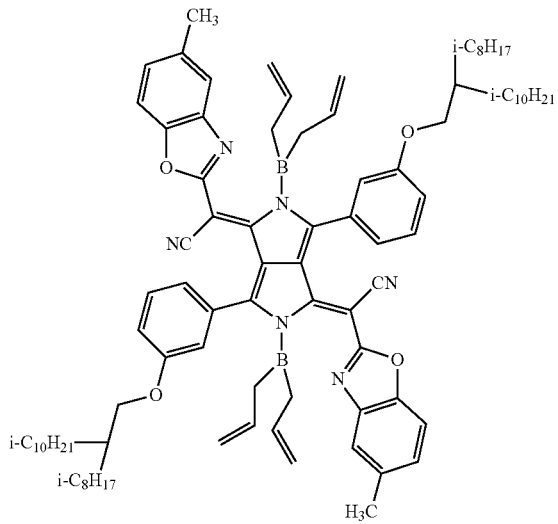

-continued
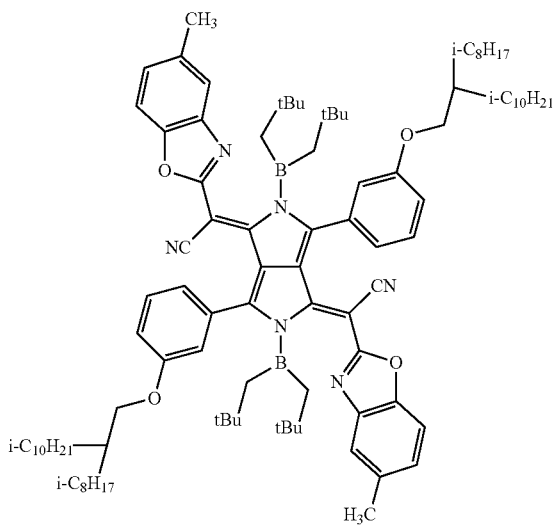
D-64
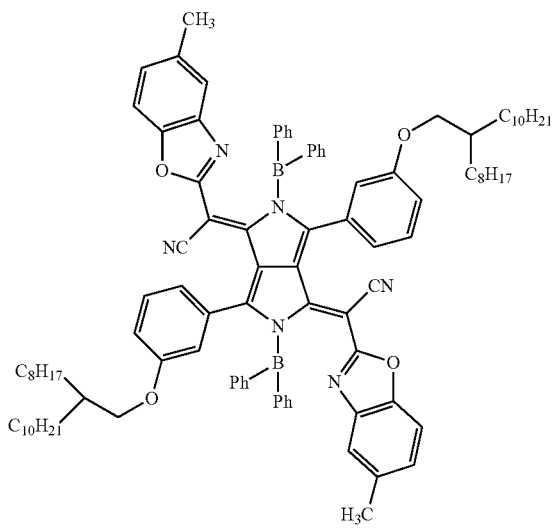
D-65
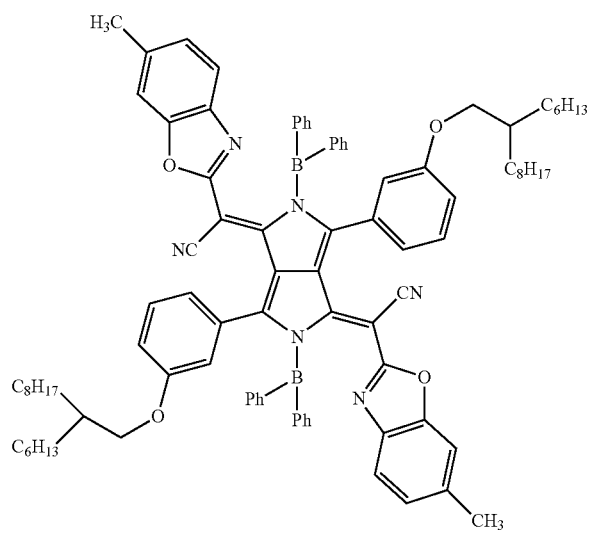
D-66
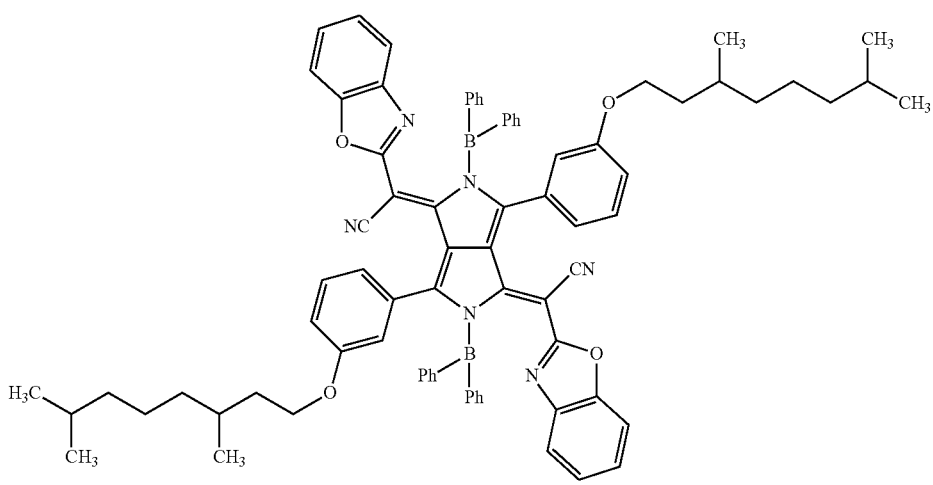
D-67

-continued
D-68
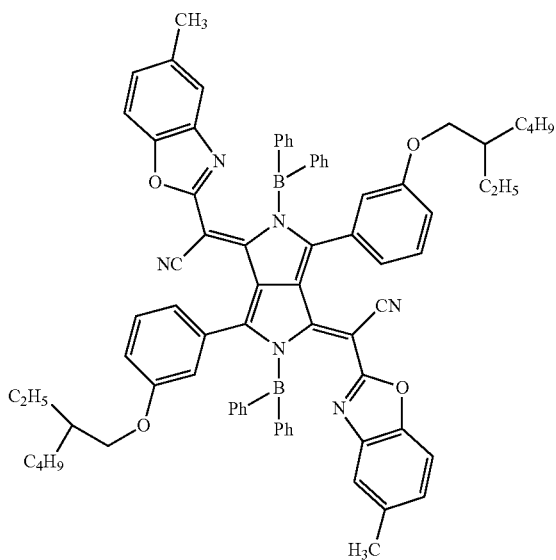
D-69
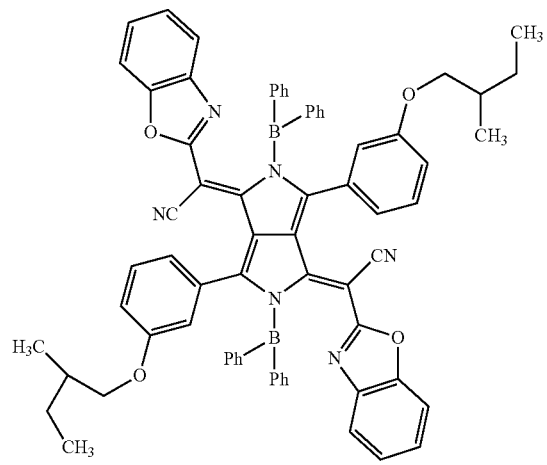
D-70
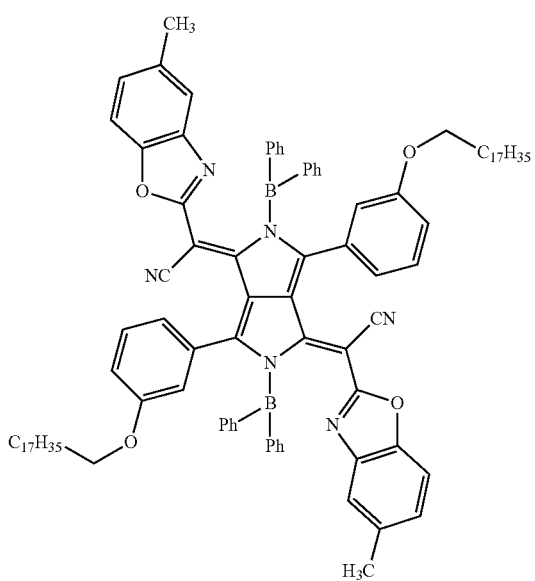
D-71
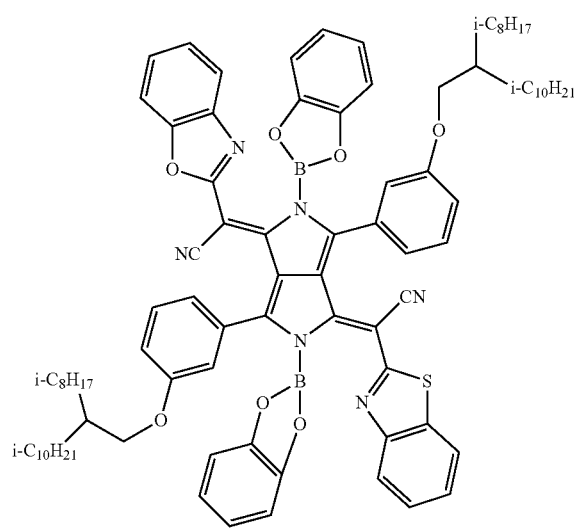

-continued
D-72
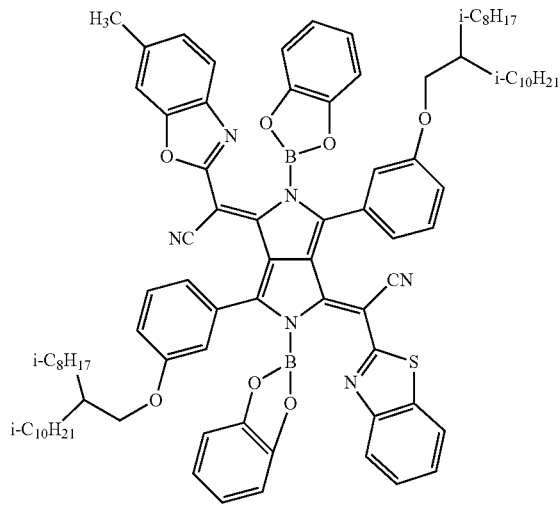
D-73
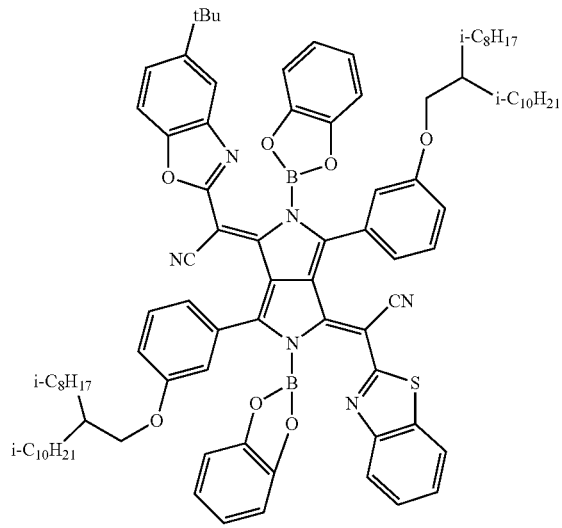
D-74
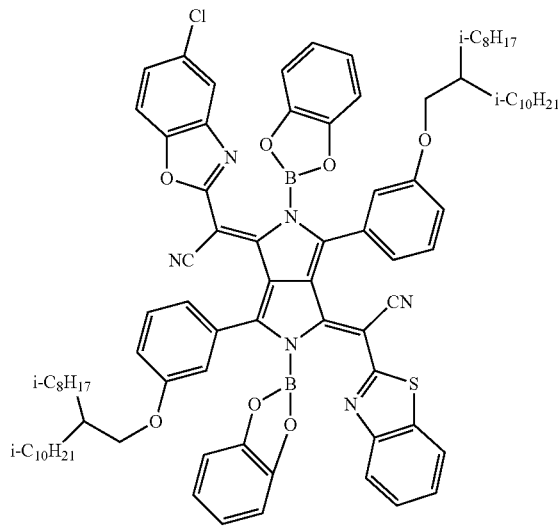
D-75
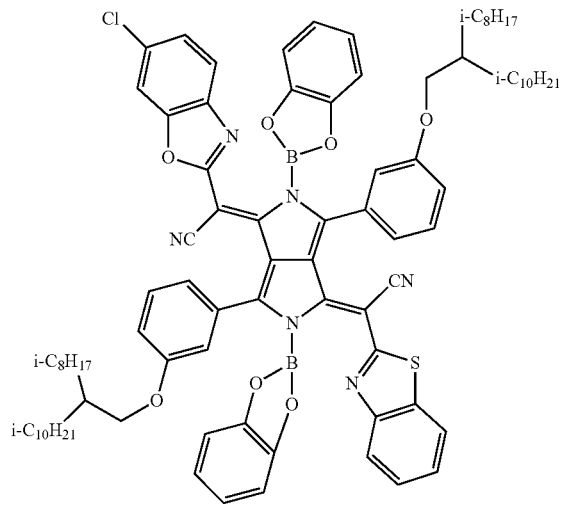
D-76
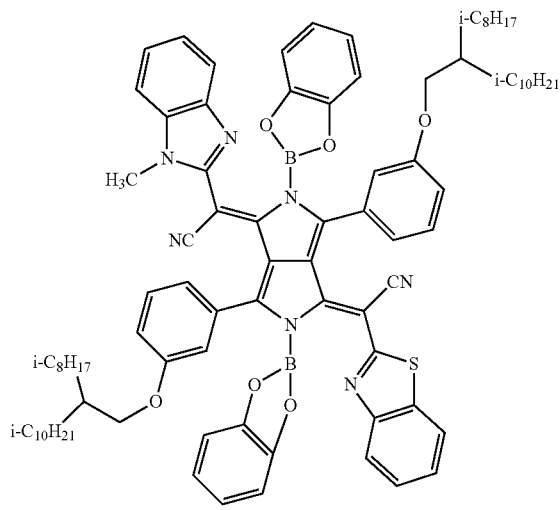
D-77
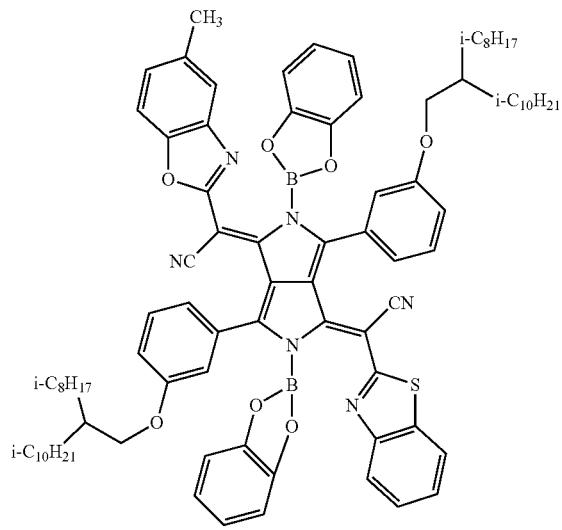

-continued
D-78
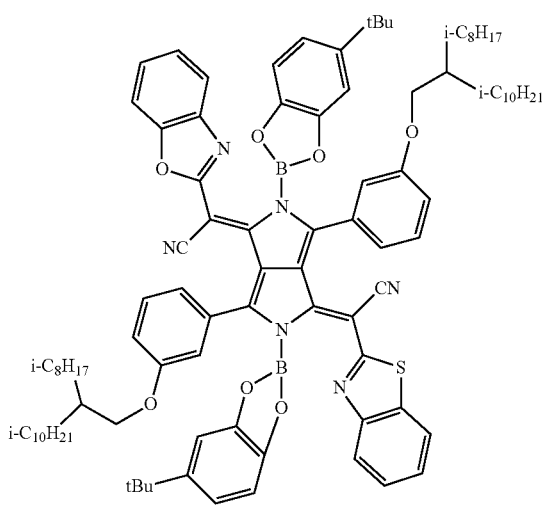
D-79
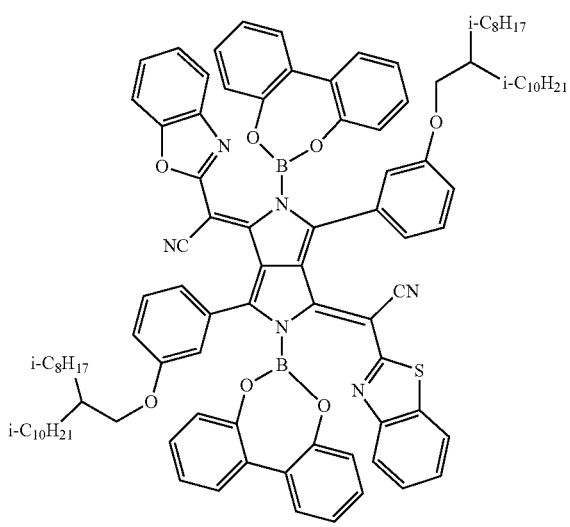
D-80
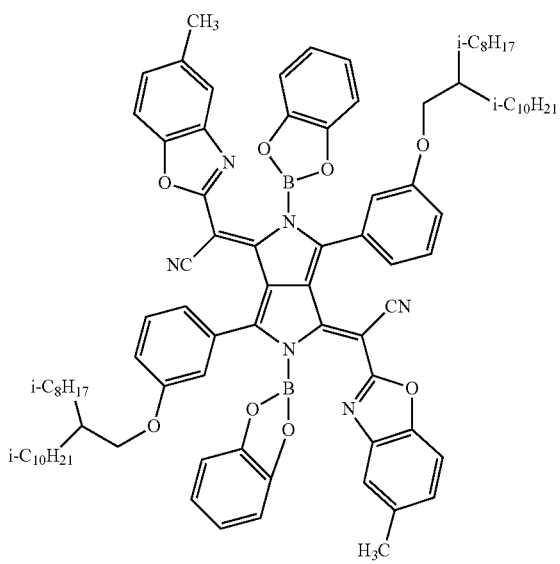
D-81
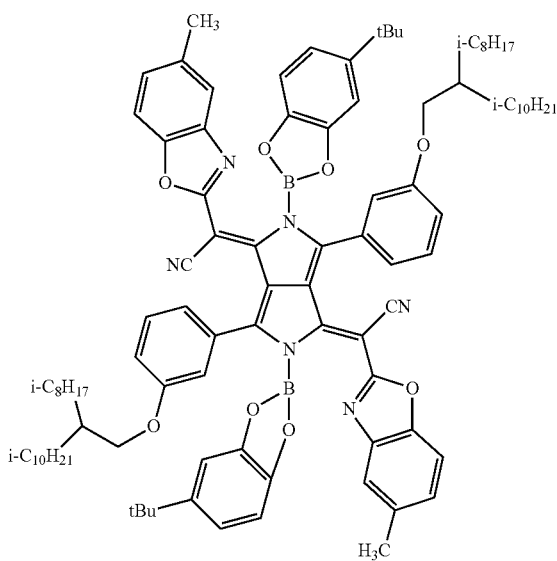
D-82
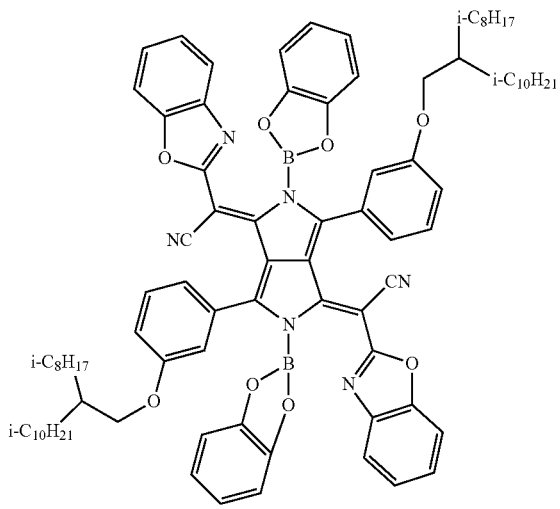
D-83
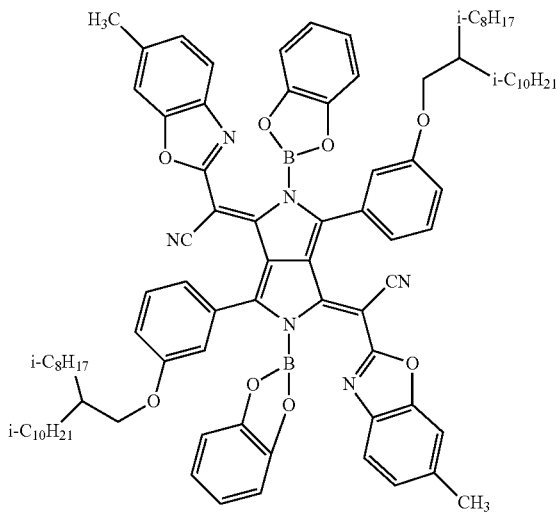

-continued
D-84
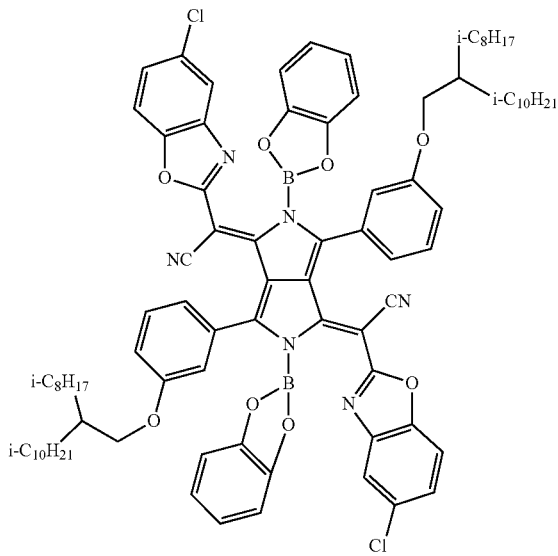
D-85
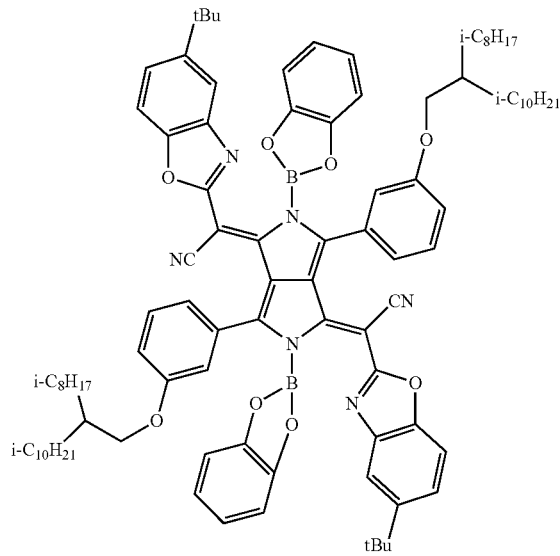
D-86
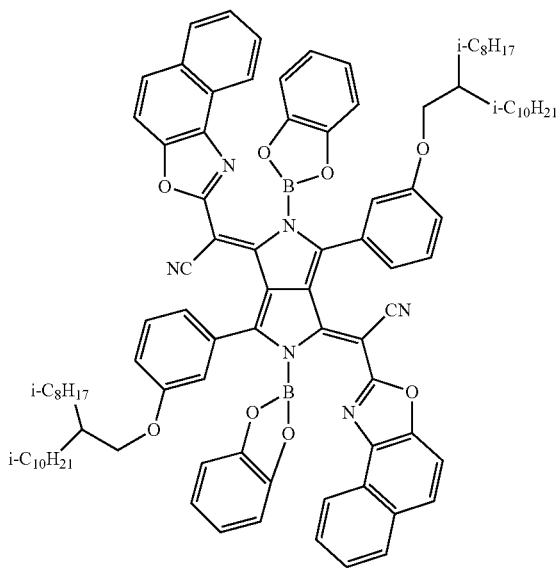
D-87
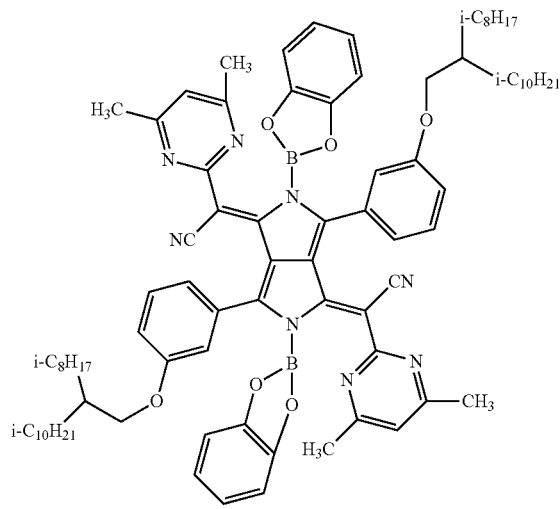

-continued

D-88
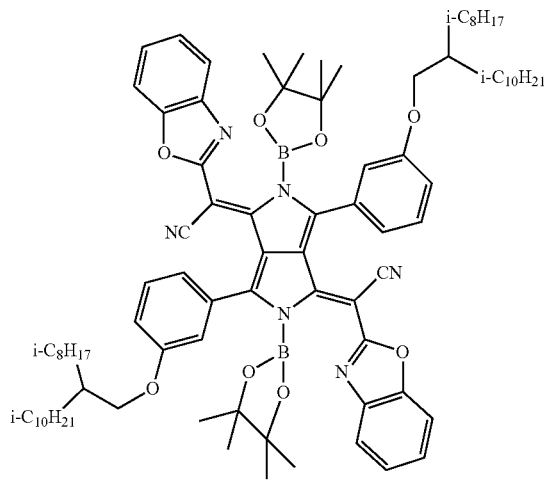

D-89
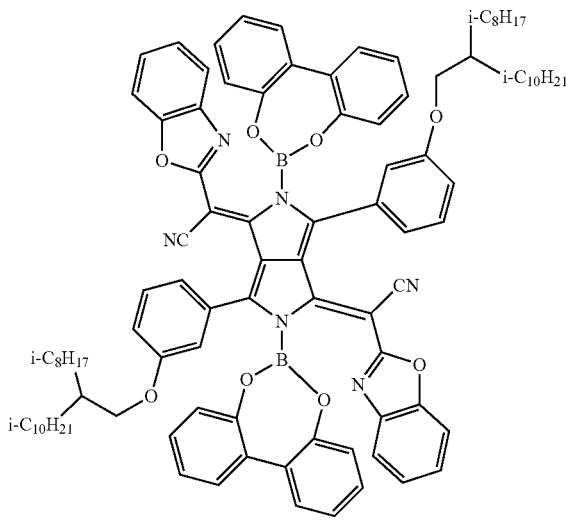

D-90
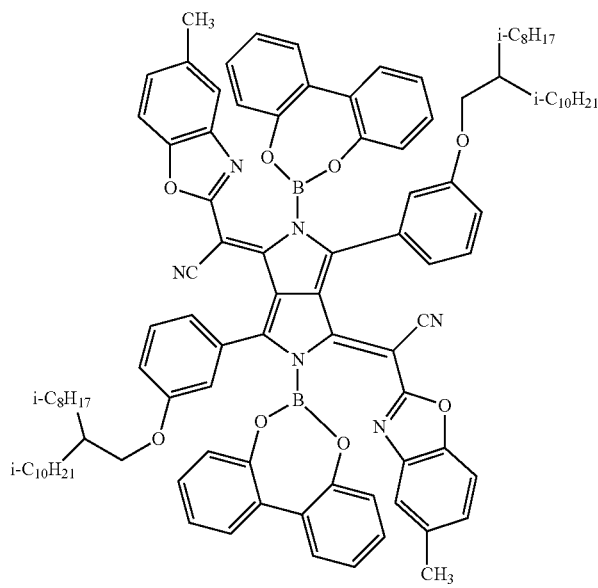

In the composition according to the invention, the content of the compound represented by Formula (1) can be adjusted, if necessary. For example, the content is preferably 0.01 to 50 mass % in the total solid content of the composition. The lower limit is preferably 0.1 mass % or greater and more preferably 0.5 mass % or greater. The upper limit is preferably 30 mass % or less and more preferably 15 mass % or less. If the content is in this range, satisfactory near infrared ray absorption properties can be applied. In a case where the composition according to the invention includes two or more types of compounds represented by Formula (1), the total amount thereof is preferably in the range described above.

The composition according to the invention can be used, for example, as (i) the use of a near infrared ray absorption filter that can absorb light in a specific near infrared ray range, (ii) a near infrared ray absorption filter that can absorb light in a near infrared ray range in a wavelength range wider than a wavelength range that is cut only by the compound represented by Formula (1), and the like.

In a case where the near infrared ray absorption composition is used as the use of the near infrared ray absorption filter of (i) above, it is preferable that the composition according to the invention contains the compound represented by Formula (1) and does substantially not contain an infrared ray absorption substance having a maximum absorption wavelength in a near infrared ray range different from a maximum absorption wavelength of a compound represented by Formula (1). Here, the expression "substantially not containing" means that a content of the compound represented by Formula (1) is 1 mass % or less.

In a case where the composition is used as the use of the near infrared ray absorption filter of (ii) above, the composition according to the invention preferably contains a near infrared ray absorption substance (other near infrared ray absorption substances described below) having a maximum absorption wavelength in a near infrared ray range different from a maximum absorption wavelength included in the compound represented by Formula (1), in addition to the compound represented by Formula (1).

Hereinafter, other components that may be contained in the composition according to the invention are described.

<<Curable Compound>>

The composition according to the invention can contain a curable compound. The curable compound may be a compound having a polymerizable group (hereinafter, also referred to as a "polymerizable compound") and may be a non-polymerizable compound such as a binder. The curable compound may be any one of chemical forms such as a monomer, an oligomer, a prepolymer, and a polymer. As the curable compound, for example, paragraphs 0070 to 0191 of JP2014-41318A (paragraphs 0071 to 0192 of corresponding WO2014/017669A), and paragraphs 0045 to 0216 of JP2014-32380A, and the contents thereof are incorporated with this specification.

The curable compound is preferably a polymerizable compound. Examples of the polymerizable compound include compounds including polymerizable groups such as an ethylenically unsaturated bond, cyclic ether (epoxy, and oxetane). As the ethylenically unsaturated bond, a vinyl group, a styryl group, a (meth)acryloyl group, and a (meth)allyl group are preferable. The polymerizable compound may be a monofunctional compound having one polymerizable group or may be a polyfunctional compound having two or more polymerizable groups, but is preferably a polyfunctional compound. If the composition contains a polyfunctional compound, heat resistance can be further improved.

Examples of the curable compound include a monofunctional (meth)acrylate, polyfunctional (meth)acrylate (preferably trifunctional to hexafunctional (meth)acrylate), a polybasic acid-modified acrylic oligomer, an epoxy resin, and a polyfunctional epoxy resin.

A content of a curable compound is preferably 1 to 90 mass % with respect to a total solid content of a composition. The lower limit is preferably 5 mass % or greater, more preferably 10 mass % or greater, and even more preferably 20 mass % or greater. The upper limit is preferably 80 mass % or less and more preferably 75 mass % or less. In a case where a polymer including a repeating unit having a polymerizable group is used as a curable compound, a content of the curable compound is preferably 10 to 75 mass % with respect to a total solid content of the composition. The lower limit is preferably 20 mass % or greater. The upper limit is preferably 65 mass % or less and more preferably 60 mass % or less.

The curable compound may be used singly or two or more types may be used in combination. In a case where two or more types are used, it is preferable that a total amount is in the range described above.

<<<Compound Including Ethylenically Unsaturated Bond>>>

According to the invention, a compound including an ethylenically unsaturated bond can be used as a curable compound. As examples of the compound including an ethylenically unsaturated bond, paragraphs 0033 and 0034 of JP2013-253224A can be referred to, and the contents thereof are incorporated to this specification.

As a compound including an ethylenically unsaturated bond, ethyleneoxy-modified pentaerythritol tetraacrylate (as a commercially available product, NK ESTER ATM-35E; manufactured by Shin-Nakamura Chemical Co., Ltd.), dipentaerythritol triacrylate (as a commercially available product, KAYARAD D-330; manufactured by manufactured by Nippon Kayaku Co., Ltd.), dipentaerythritol tetraacrylate (as a commercially available product, KAYARAD D-320; manufactured by Nippon Kayaku Co., Ltd.), dipentaerythritol penta(meth)acrylate (as a commercially available product, KAYARAD D-310; manufactured by Nippon Kayaku Co., Ltd.), dipentaerythritol hexa(meth)acrylate (as commercially available products, KAYARAD DPHA; manufactured by Nippon Kayaku Co., Ltd., A-DPH-12E; manufactured by Shin-Nakamura Chemical Co., Ltd.), and a structure in which ethylene glycol, propylene glycol residues are interposed between these (meth)acryloyl groups are preferable. An oligomer type of these can be used.

Polymerizable compounds of paragraphs 0034 to 0038 disclosed in JP2013-253224A can be referred to, and the contents thereof are incorporated to this specification.

Examples thereof include polymerizable monomers disclosed in paragraphs 0477 of JP2012-208494A ([0585] of corresponding US2012/0235099A), and the contents thereof are incorporated to this specification.

Diglycerine ethyleneoxide (EO)-modified (meth)acrylate (as a commercially available product, M-460; manufactured by Toagosei Co., Ltd.) is preferable. Pentaerythritol tetraacrylate (manufactured by Shin-Nakamura Chemical Co., Ltd., A-TMMT), 1,6-hexanediol diacrylate (manufactured by Nippon Kayaku Co., Ltd., KAYARAD HDDA) is also preferable. An oligomer type of these can be used. Examples thereof include RP-1040 (manufactured by Nippon Kayaku Co., Ltd.).

The compound including an ethylenically unsaturated bond may have an acid group such as a carboxyl group, a sulfo group, or a phosphoric acid group.

Examples of a compound including an acid group and an ethylenically unsaturated bond include ester between an aliphatic polyhydroxy compound and an unsaturated carboxylic acid. A compound caused to have an acid group by being reacted with a non-aromatic carboxylic acid anhydride is preferable in an unreacted hydroxyl group of an aliphatic polyhydroxy compound. Particularly preferably, in this ester, an aliphatic polyhydroxy compound is pentaerythritol and/or dipentaerythritol. Examples of a commercially available product include M-305, M-510, and M-520 of ARONIX series, as a polybasic acid-modified acrylic oligomer manufactured by Toagosei Co., Ltd.

An acid value of a compound including an acid group and an ethylenically unsaturated bond is preferably 0.1 to 40 mgKOH/g. The lower limit is preferably 5 mgKOH/g or greater. The upper limit is preferably 30 mgKOH/g or less.

<<<Compound Having Epoxy Group or Oxetanyl Group>>>

According to the invention, a compound having an epoxy group or an oxetanyl group can be used as a curable compound. Examples of the compound having an epoxy group or an oxetanyl group include a polymer having an epoxy group on a side chain, and a monomer or an oligomer that has two or more epoxy groups in a molecule. Examples thereof include a Bisphenol A-type epoxy resin, a Bisphenol F-type epoxy resin, a phenol novolac-type epoxy resin, a cresol novolac-type epoxy resin, and an aliphatic epoxy resin. Examples thereof include a monofunctional or polyfunctional glycidyl ether compound, and a polyfunctional aliphatic glycidyl ether compound is preferable.

A weight-average molecular weight is preferably in the range of 500 to 5,000,000 and further 1,000 to 500,000.

As these compounds, commercially available products may be used, or a compound that can be obtained by introducing an epoxy group to a side chain of a polymer may be used.

As a commercially available product, for example, disclosure of paragraph 0191 of JP2012-155288A can be referred to, and the contents thereof are incorporated to this specification.

Examples of a commercially available product include a polyfunctional aliphatic glycidyl ether compound such as DENACOL EX-212L, EX-214L, EX-216L, EX-321L, and EX-850L (above, manufactured by Nagase ChemteX Corporation). These are low chlorine products, but EX-212, EX-214, EX-216, EX-321, EX-850, and the like which are not low chlorine products can be used in the same manner.

Examples thereof also include ADEKA RESIN EP-4000S, ADEKA RESIN EP-4003S, ADEKA RESIN EP-4010S, and ADEKA RESIN EP-4011S (above, manufactured by ADEKA Corporation), NC-2000, NC-3000, NC-7300, XD-1000, EPPN-501, and EPPN-502 (above, manufactured by ADEKA Corporation), JER1031S, CELLOXIDE 2021P, CELLOXIDE 2081, CELLOXIDE 2083, CELLOXIDE 2085, EHPE3150, EPOLEAD PB 3600, EPOLEAD PB 4700 (above, manufactured by Daicel Corporation), CYCLOMER P ACA 200M, CYCLOMER P ACA 230AA, CYCLOMER P ACA Z250, CYCLOMER P ACA Z251, CYCLOMER. P ACA Z300, and CYCLOMER P ACA Z320 (above, manufactured by Daicel Corporation).

Examples of a commercially available product of a phenol novolac-type epoxy resin include JER-157565, JER-152, JER-154, and JER-157S70 (above are manufactured by Mitsubishi Chemical Corporation).

As specific examples of a polymer having an oxetanyl group on a side chain and a polymerizable monomer or a polymerizable oligomer that have two or more oxetanyl groups in a molecule, ARON OXETANE OXT-121, OXT-221, OX-SQ, and PNOX (above, manufactured by Toagosei Co., Ltd.) can be used.

As the compound having an epoxy group, a compound having a glycidyl group as an epoxy group such as glycidyl (meth)acrylate or allyl glycidyl ether can be used, but a preferable compound is an unsaturated compound having an alicyclic epoxy group. As an example thereof, disclosure of paragraph 0045 or the like of JP2009-265518A can be referred to, and the contents thereof are incorporated to this specification.

The compound including an epoxy group or an oxetanyl group may include a polymer having an epoxy group or an oxetanyl group as a repeating unit.

<<<Other Curable Compound>>>

According to the invention, a polymerizable compound having a caprolactone-modified structure can be used as a curable compound.

As a polymerizable compound having a caprolactone-modified structure, disclosure of paragraphs 0042 to 0045 of JP2013-253224A can be referred to, and the contents thereof are incorporated to this specification.

Examples of the polymerizable compound having a caprolactone-modified structure include DPCA-20, DPCA-30, DPCA-60, and DPCA-120 that are commercially available as a KAYARAD DPCA series from Nippon Kayaku Co., Ltd., and SR-494 that is tetrafunctional acrylate having four ethyleneoxy chains manufactured by Sartomer, and TPA-330 that is trifunctional acrylate having three isobutyleneoxy chains.

<<Photopolymerization Initiator>>

The composition according to the invention may contain a photopolymerization initiator.

The content of the photopolymerization initiator is preferably 0.01 to 30 mass %. The lower limit is preferably 0.1 mass % or greater and more preferably 0.5 mass % or greater. The upper limit is preferably 20 mass % or less and more preferably 15 mass % or less.

The photopolymerization initiator may be used singly or two or more types may be used in combination. In a case where two or more types are used, it is preferable that a total amount is in the range described above.

The photopolymerization initiator is not particularly limited, as long as the photopolymerization initiator has capability of initiating polymerization of the curable compound by light. The photopolymerization initiator can be appropriately selected depending on purposes. In a case where polymerization is initiated by light, it is preferable to have photosensitivity on visible light from an ultraviolet ray range.

The photopolymerization initiator is preferably a compound having at least an aromatic group, and examples thereof include an acylphosphine compound, an acetophenone compound, an a-aminoketone compound, a benzophenone-based compound, a benzoin ether-based compound, a ketal derivative compound, a thioxanthone compound, an oxime compound, a hexaarylbiimidazole compound, a trihalomethyl compound, an azo compound, an organic peroxide, an onium salt compound such as a diazonium compound, an iodonium compound, a sulfonium compound, an azinium compound, and a metallocene compound, an organic boron salt compound, a disulfone compound, and a thiol compound.

As the photopolymerization initiator, disclosure of paragraphs 0217 to 0228 of JP2013-253224A can be referred to, and the contents thereof are incorporated to this specification.

As the oxime compound, IRGACURE-OXE01 (manufactured by BASF SE Corp.), IRGACURE-OXE02 (manufactured by BASF SE Corp.), TR-PBG-304 (manufactured by Changzhou Tronly New Electronic Materials Co., Ltd.), ADEKA ARKLS NCI-831 (manufactured by ADEKA Corporation), ADEKA ARKLS NCI-930 (manufactured by ADEKA Corporation), or the like which are commercially available products can be used.

As an acetophenone-based compound, IRGACURE-907, IRGACURE-369, and IRGACURE-379 (Product name: all are manufactured by BASF Japan Ltd.) which are commercially available products can be used. As an acylphosphine compound, IRGACURE-819 or DAROCUR-TPO (Product name: all are manufactured by BASF Japan Ltd.) which are commercially available products can be used.

The invention can use an oxime compound having a fluorine atom as the photopolymerization initiator. Specific examples of the oxime compound having a fluorine atom include compounds disclosed in JP2010-262028A, compounds 24, and 36 to 40 disclosed in JP2014-500852A, a compound (C-3) disclosed in JP2013-164471A. The contents thereof are incorporated to this specification.

<<Solvent>>

The composition according to the invention may contain a solvent. The solvent is not particularly limited, and can be appropriately selected depending on purposes, as long as respective components of the composition according to the invention can be evenly dissolved or dispersed in the solvent. For example, water or an organic solvent can be used, and an organic solvent is preferable.

Examples of the organic solvent suitably include alcohols (for example, methanol), ketones, esters, aromatic hydrocarbons, halogenated hydrocarbons, and dimethylformamide, dimethylacetamide, dimethylsulfoxide, and sulfolane. These may be used singly or two or more types thereof may be used in combination.

Specific examples of alcohols, aromatic hydrocarbons, and halogenated hydrocarbons include those disclosed in paragraph 0136 of JP2012-194534A and the like, and the contents thereof are incorporated with this specification.

Specific examples of esters, ketones, and ethers include those disclosed in paragraph 0497 of JP2012-208494A ([0609] of corresponding US2012/0235099A) and include n-amyl acetate, ethyl propionate, dimethyl phthalate, ethyl benzoate, methyl sulfate, acetone, methyl isobutyl ketone, diethyl ether, and ethylene glycol monobutyl ether acetate.

According to the invention, one or more selected from ethanol, methanol, methyl 3-methoxypropionate, ethyl 3-methoxypropionate, methyl 3-ethoxypropionate, ethyl 3-ethoxypropionate, N-methyl-2-pyrrolidone, ethyl cellosolve acetate, ethyl lactate, butyl acetate, diethylene glycol dimethyl ether, 2-heptanone, cyclopentanone, cyclohexanone, ethyl carbitol acetate, butyl carbitol acetate, ethylene glycol monobutyl ether acetate, propylene glycol monomethyl ether, and propylene glycol monomethyl ether acetate are preferable as a solvent.

The content of the solvent is preferably an amount in which a total solid content of the composition according to the invention becomes 10 to 90 mass %. The lower limit is more preferably 15 mass % or greater and even more preferably 20 mass % or greater. The upper limit is more preferably 80 mass % or less and even more preferably 70 mass % or less.

The solvent may be used singly, or two or more types thereof may be used. In a case where two or more types are used, it is preferable that the total amount thereof is in the range described above.

<<Resin>>

The composition according to the invention may contain a resin. Examples of the resin include an alkali soluble resin.

The alkali soluble resin can be appropriately selected from alkali soluble resins which are linear organic high molecular polymers and have at least one group that promotes alkali solubility in a molecule (preferably, a molecule using an acrylic copolymer or a styrene-based copolymer as a main chain). In view of heat resistance, a polyhydroxystyrene-based resin, a polysiloxane-based resin, an acrylic resin, an acrylamide-based resin, and acryl/acrylamide copolymer resins are preferable. In view of developability control, an acrylic resin, an acrylamide-based resin, and an acryl/acrylamide copolymer resins are preferable.

Examples of a group promoting alkali solubility (hereinafter, also referred to as an acid group) include a carboxyl group, a phosphoric acid group, a sulfonic acid group, and a phenolic hydroxyl group. However, groups that are soluble to an organic solvent and can be developed by a weak alkali aqueous solution are preferable, and (meth)acrylic acid is particularly preferable. These acid groups may be used singly or two or more types thereof may be used in combination. As the alkali soluble resin, disclosure of paragraphs 0558 to 0571 ([0685] to [0700] of corresponding US2012/0235099A) or following paragraphs of JP2012-208494A is referred to, and the contents thereof are incorporated to this specification.

As an alkali soluble resin, a resin including a compound represented by Formula (ED) below as a copolymerization component is also preferable.

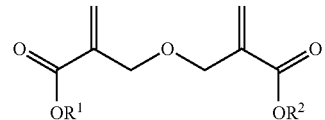

In Formula (ED), $R^1$ and $R^2$ each independently represent a hydrocarbon group having 1 to 25 carbon atoms that may have a hydrogen atom or a substituent.

The hydrocarbon group having 1 to 25 carbon atoms that is represented by $R^1$ and $R^2$ is not particularly limited, and examples thereof include linear or branched alkyl group such as methyl, ethyl, n-propyl, isopropyl, n-butyl, isobutyl, t-butyl, t-amyl, stearyl, lauryl, and 2-ethylhexyl; an aryl group such as phenyl; an alicyclic group such as cyclohexyl, t-butylcyclohexyl, dicyclopentadienyl, tricyclodecanyl, isobornyl, adamantyl, and 2-methyl-2-adamantyl; an alkyl group substituted with alkoxy such as 1-methoxyethyl and 1-ethoxyethyl; and an alkyl group substituted with an aryl group such as benzyl. Among these, particularly, a primary or secondary hydrocarbon group that hardly leaves due to acid or heat such as methyl, ethyl, cyclohexyl, and benzyl is preferable, in view of heat resistance.

$R^1$ and $R^2$ may be substituents in the same type or may be substituents in different types.

Examples of the compound represented by Formula (ED) include dimethyl 2,2'-[oxybis(methylene)]bis-2-propenoate, diethyl-2,2'-[oxybis(methylene)]bis-2-propenoate, di(n-propyl)-2,2'-[oxybis(methylene)]bis-2-propenoate, di(n-butyl)-2,2'-[oxybis(methylene)]bis-2-propenoate, di(t-butyl)-2,2'-[oxybis(methylene)]bis-2-propenoate, and di(isobutyl)-2,2'-[oxybis(methylene)]bis-2-propenoate. Among these, particularly, dimethyl 2,2'-[oxybis(methylene)]bis-2-propenoate is preferable.

A copolymerization component other than the compound represented by Formula (ED) is not particularly limited.

For example, in view of easy handleability such as solubility to a solvent, it is preferable to include aryl (meth)acrylate, alkyl (meth)acrylate, and polyethyleneoxy (meth)acrylate that provide oil solubility as a copolymerization component, and it is more preferable to include aryl (meth)acrylate or alkyl (meth)acrylate.

In view of alkali developability, it is preferable to include a monomer having a carboxyl group such as (meth)acrylic acid or itaconic acid that contains an acidic group, a monomer having a phenolic hydroxyl group such as N-hydroxyphenyl maleimide, and a monomer having a carboxylic acid anhydride group such as maleic anhydride and itaconic anhydride, as a copolymerization component, and (meth)acrylic acid is more preferable.

Examples of a preferable combination of copolymer components include a combination of a compound represented by Formula (ED), benzyl methacrylate, and methyl methacrylate and/or methacrylic acid.

With respect to a resin including a compound represented by Formula (ED) as a copolymerization component, disclosure in paragraph numbers 0079 to 0099 of JP2012-198408A can be referred to, and the contents thereof are incorporated with this specification.

The acid value of the alkali soluble resin is preferably 30 to 200 mgKOH/g. The lower limit is preferably 50 mgKOH/g or greater and more preferably 70 mgKOH/g or greater. The upper limit is preferably 150 mgKOH/g or less and more preferably 120 mgKOH/g or less.

The weight-average molecular weight (Mw) of the alkali soluble resin is preferably 2,000 to 50,000. The lower limit is preferably 5,000 or greater and more preferably 7,000 or greater. The upper limit is preferably 30,000 or less and more preferably 20,000 or less.

In a case where the composition according to the invention contains a resin, the content of the resin is preferably 1 to 80 mass % with respect to the total solid content of the composition. The lower limit is preferably 5 mass % or greater and more preferably 7 mass % or greater. The upper limit is preferably 70 mass % or less and more preferably 60 mass % or less.

The composition according to the invention may include only one type of resin and may include two or more types thereof. In a case where the composition includes two or more types thereof, it is preferable that a total amount is in the range described above.

<<Surfactant>>

The composition according to the invention may contain a surfactant. Only one type of surfactant may be used or two or more types thereof may be used in combination. The content of the surfactant is preferably 0.0001 to 5 mass % with respect to the total solid content of the composition according to the invention. The lower limit is preferably 0.005 mass % or greater and more preferably 0.01 mass % or greater. The upper limit is preferably 2 mass % or less and more preferably 1 mass % or less.

As the surfactant, various surfactants such as a fluorine-based surfactant, a nonionic surfactant, a cation-based surfactant, an anion-based surfactant, and a silicone-based surfactant can be used. It is preferable that the composition according to the invention contains at least one of a fluorine-based surfactant or a silicone-based surfactant. Surface tension between a coated surface and a coating liquid decreases, and wettability to a coated surface improves. Therefore, characteristics (particularly, fluidity) of liquid of the composition are improved, and evenness of coating thickness and liquid saving properties are further improved. As a result, even in a case where a thin film in about several μm is formed with a small amount of liquid, it is possible to form a film having small unevenness of a thickness and a homogeneous thickness.

A content of fluorine of a fluorine-based surfactant is preferably 3 to 40 mass %. The lower limit is preferably 5 mass % or greater and even more preferably 7 mass % or greater. The upper limit is preferably 30 mass % or less and even more preferably 25 mass % or less. In a case where a fluorine content is in the range described above, it is effective in view of the evenness of the thickness of a coated film and liquid saving properties and solubility is also satisfactory.

Specific examples of the fluorine-based surfactant include surfactants disclosed in paragraphs 0060 to 0064 of JP2014-41318A (paragraphs 0060 to 0064 of corresponding WO2014/17669A), and the contents thereof are incorporated to this specification. Examples of the commercially available product of the fluorine-based surfactant include Megaface F-171, Megafac F-172, Megafac F-173, Megafac F-176, Megafac F-177, Megafac F-141, Megafac F-142, Megafac F-143, Megafac F-144, Megafac R30, Megafac F-437, Megafac F-475, Megafac F-479, Megafac F-482, Megafac F-554, Megafac F-780, and Megafac F-781F (above, manufactured by DIC Corporation), FLUORAD FC430, FLUORAD FC431, and FLUORAD FC171 (above, manufactured by Sumimoto 3M Limited.), SURFLON S-382, SURFLON SC-101, SURFLON SC-103, SURFLON SC-104, SURFLON SC-105, SURFLON SC1068, SURF-LON SC-381, SURFLON SC-383, SURFLON S393, and SURFLON KH-40 (above, Asahi Glass Co., Ltd.).

Specific examples of the nonionic surfactant further include nonionic surfactants disclosed in paragraph 0553 of JP2012-208494A ("0679" of corresponding US2012/0235099A), and the contents thereof are incorporated to this specification.

Specific examples of the cation-based surfactant include cation-based surfactants disclosed in paragraph 0554 of JP2012-208494A ([0680] of corresponding US2012/0235099A), and the contents thereof are incorporated to this specification.

Specific examples of the anion-based surfactant include W004, W005, and W017 (manufactured by Yusho Co., Ltd.).

Examples of the silicone-based surfactant include silicone-based surfactants disclosed in paragraph 0556 of JP2012-208494A ([0682] of corresponding US2012/0235099A), and the contents thereof are incorporated to this specification.

<<Polymerization Inhibitor>>

In the manufacturing or preservation, the composition according to the invention may contain a small amount of polymerization inhibitor, in order to prevent unnecessary reaction of the curable compound.

Examples of the polymerization inhibitor include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitrosophenylhydroxylamine cerous salt, and p-methoxyphenol is preferable.

In a case where the composition according to the invention contains a polymerization inhibitor, the content of the polymerization inhibitor is preferably 0.01 to 5 mass % with respect to the total solid content of the composition according to the invention.

<<Ultraviolet Absorbing Agent>>

The composition according to the invention may contain an ultraviolet absorbing agent.

The ultraviolet absorbing agent is a compound of which a light absorption coefficient per 1 g at a wavelength of 365 nm is greater than 100 and a light absorption coefficient per 1 g at a wavelength of 400 nm or greater is 10 or less. The light absorption coefficient is a value measured with an ultraviolet visible light spectrophotometer (manufactured by Agilent Technologies, Cary-5 spectrophotometer) by using an ethyl acetate solvent in a concentration of 0.01 g/L.

In the ultraviolet absorbing agent, compounds of paragraph numbers 0137 to 0142 of JP2012-068418A (paragraphs 0251 to 0254 of corresponding US2012/0068292A) can be used, the contents thereof are referred to and are incorporated with this specification. Examples of a commercially available product include UV503 (Daito Chemical Co., Ltd.).

The composition according to the invention may include or may not include an ultraviolet absorbing agent. However, in a case where the composition according to the invention include an ultraviolet absorbing agent, the content of the ultraviolet absorbing agent is preferably 0.01 to 10 mass % and more preferably 0.01 to 5 mass % with respect to a total solid content of the composition.

According to the invention, one type of the ultraviolet absorbing agent may be used, and two or more types thereof may be used in combination.

<<Other Near Infrared Ray Absorption Substance>>

The composition according to the invention may further include a near infrared ray absorption substance (hereinafter, also referred to as other near infrared ray absorption substances) having a maximum absorption wavelength in a near infrared ray range different from a maximum absorption wavelength of the compound represented by Formula (1). According to the embodiment, it is possible to obtain the near infrared ray absorption filter that can absorb light in a near infrared ray range with a wider wavelength range than light that can be cut only by the compound represented by Formula (1).

Examples of the infrared ray absorption substance include a copper compound, a cyanine-based coloring agent compound, a phthalocyanine-based compound, an imonium-based compound, a thiol complex-based compound, a transition metal oxide-based compound, a squarylium-based coloring agent compound, a naphthalocyanine-based coloring agent compound, a quaterrylene-based coloring agent compound, a dithiol metal complex-based coloring agent compound, and a croconium compound.

As a phthalocyanine-based compound, a naphthalocyanine compound, an immonium-based compound, a cyanine-based coloring agent, a squarylium-based coloring agent, and a croconium compound, compounds disclosed in paragraphs 0010 to 0081 of JP2010-111750A may be used, and the contents thereof are incorporated to this specification. As the cyanine-based coloring agent, for example, "Functional coloring agent, written by Okawara Shin, Matsuoka Ken, Kitao Teijirou, and Hirashima Kousuke, published by Kodansha Scientific Ltd." can be referred to, and the contents thereof are incorporated to this specification.

As a copper compound, copper compounds of paragraph numbers 0013 to 0056 of JP2014-41318A and paragraph numbers 0012 to 0030 of JP2014-32380A may be used, and the contents thereof are incorporated to this specification.

Compounds disclosed in paragraphs 0004 to 0016 of JP1995-164729A (JP-H07-164729A), compounds disclosed in paragraphs 0027 to 0062 of JP2002-146254A, and near infrared ray absorption particles that are disclosed in paragraphs 0034 to 0067 of JP2011-164583A, that consist of crystallites of oxide including Cu and/or P, and that have a number-average aggregate particle diameter of 5 to 200 nm may be used, and the contents thereof are incorporated to this specification.

As a commercially available product, "IRA842" manufactured by Exiton, "FD-25" manufactured by Yamada Kagaku Co., Ltd., and the like can be used.

<<Other Components>>

Examples of other components that can be used together in the composition according to the invention include a sensitizing agent, a crosslinking agent, a hardening accelerator, a filler, a thermal hardening accelerator, a thermal polymerization inhibitor, and a plasticizer, and an adhesion promoter to a surface of a base material and other auxiliary agents (for example, a conductive particle, a filler, an anti-foaming agent, a flame retardant, a leveling agent, a peeling promoter, an antioxidant, a fragrance material, a surface tension adjuster, and a chain transfer agent) may be used together.

If these components are appropriately contained, it is possible to adjust desired characteristics such as stability of the near infrared ray absorption filter and film properties.

As these components, for example, disclosure in paragraph numbers 0183 to 0228 of JP2012-003225A ([0237] to [0309] of corresponding US2013/0034812A), paragraph numbers 0101 and 0102, paragraph numbers 0103 to 0104, and paragraph numbers 0107 to 0109 of JP2008-250074A, and paragraph numbers 0159 to 0184 of JP2013-195480A can be referred to, and the contents thereof are incorporated to this specification.

<Preparation and Use of Composition>

The composition according to the invention can be prepared by mixing the respective components described above.

At the time of preparation of the composition, respective components that form the composition can be collectively formulated, and may be sequentially formulated after respective components are dissolved and dispersed in an organic solvent. The input order or the working condition at the time of formulation is not particularly limited.

According to the invention, for the purpose of removing foreign substances, decreasing defects, and the like, the composition is preferably filtrated with a filter. A filter is not particularly limited, as long as the filter is used for filtration in the related art. Examples thereof include a filter using a fluorine resin such as polytetrafluoroethylene (PTFE), a polyamide-based resin such as nylon-6 and nylon-6,6, a polyolefin resin such as polyethylene and polypropylene (PP) (including resins with high density and ultra high molecular weight). Among these raw materials, polypropylene (including a high density polypropylene) and nylon are preferable.

A hole diameter of a filter is preferably 0.1 to 7.0 μm, more preferably 0.2 to 2.5 μm, even more preferably 0.2 to 1.5 μm, and still even more preferably 0.3 to 0.7 μm. If the content thereof is this range, filtration clogging can be suppressed, and it is possible to securely remove fine foreign substances such as impurities or agglomerates included in the composition.

At the time of using a filter, other filters may be combined. At this time, filtering with a first filter may be performed once or may be performed twice or more times. In a case where filtering is performed twice or more times in combination with other filters, it is preferable that a hole diameter of the first filtering is identical to or greater than a hole diameter of the second or subsequent filtering. It is possible to combine first filters having different hole diameters in the range described above. As the hole diameter described herein, a nominal value of a filter manufacturer can be referred to. The commercially available filter can be selected from various filters provided by, for example, Nihon Pall Ltd., Advantec Toyo Kaisha, Ltd., Nihon Entegris K.K. (Mykrolis Corporation), or Kitz Microfilter Corporation.

As the second filter, a filter that is formed with the same material as that of the first filter can be used. The hole diameter of the second filter is preferably 0.2 to 10.0 μm, more preferably 0.2 to 7.0 μm, and even more preferably 0.3 to 6.0 μm. If the hole diameter is in the range described above, it is possible to remove foreign substances while component particles contained in the composition remain.

In a case where the near infrared ray absorption filter is formed by coating, the viscosity of the composition according to the invention is preferably in the range of 1 to 3,000 mPa·s. The lower limit is preferably 10 mPa·s or greater and more preferably 100 mPa·s or greater. The upper limit is preferably 2,000 mPa·s or less, and more preferably 1,500 mPa·s or less.

The composition according to the invention can be used in a near infrared ray absorption filter (for example, a near infrared ray absorption filter for a wafer level lens) on a light receiving side of a solid-state imaging device and a near infrared ray absorption filter on a back surface side (an opposite side of a light receiving side) of a solid-state imaging device, and the like. The image sensor was directly coated with the composition according to the invention, and a coating film is formed to be used.

Since the composition according to the invention can be supplied in a coatable state, a near infrared ray absorption filter can be easily formed on a desired member or a desired position of a solid-state imaging device.

<Cured Film and Near Infrared Ray Absorption Filter>

The cured film and the near infrared ray absorption filter according to the invention is formed by using the composition according to the invention described above.

With respect to the near infrared ray absorption filter according to the invention, light transmittance preferably satisfies at least one of condition (1), condition (2), condition (3), or condition (4) below, or further preferably satisfies all the conditions (1) to (4).

(1) The light transmittance in a wavelength of 400 nm is preferably 70% or greater, more preferably 80% or greater, even more preferably 85% or greater, and particularly preferably 90% or greater.

(2) The light transmittance in a wavelength of 500 nm is preferably 70% or greater, more preferably 80% or greater, even more preferably 90% or greater, and particularly preferably 95% or greater.

(3) The light transmittance in a wavelength of 600 nm is preferably 70% or greater, more preferably 80% or greater, even more preferably 90% or greater, and particularly preferably 95% or greater.

(4) The light transmittance in a wavelength of 650 nm is preferably 70% or greater, more preferably 80% or greater, even more preferably 90% or greater, and particularly preferably 95% or greater.

A film thickness of a near infrared ray absorption filter according to the invention can be appropriately selected depending on purposes. The film thickness is preferably 20 μm or less, more preferably 10 μm or less, and further preferably 5 μm or less. The lower limit of the film thickness is preferably 0.1 μm or greater, more preferably 0.2 μm or greater, and even more preferably 0.3 μm or greater.

With respect to the near infrared ray absorption filter according to the invention, light transmittance in an entire wavelength range of 400 to 650 nm is preferably 70% or greater, more preferably 80% or greater, and even more preferably 90% or greater, in a film thickness of 20 μM or less. It is preferable that light transmittance at least one point in a wavelength range of 700 nm to 1,000 nm is 20% or less.

The infrared absorption filter according to the invention preferably has a maximum absorption wavelength in a wavelength range of 700 to 1,000 nm. The half-width of the maximum absorption wavelength is preferably 60 nm or less, more preferably 50 nm or less, and even more preferably 45 nm or less. For example, the lower limit is preferably 1 nm or greater. A value obtained by dividing the absorbance at a wavelength of 550 nm by absorbance at the maximum absorption wavelength is preferably 0.015 or less and more preferably 0.014 or less. For example, the lower limit is preferably 0.001 or greater. According to this aspect, it is possible to obtain a near infrared ray absorption filter having excellent transparency in a visible region and high near infrared shielding properties.

The near infrared ray absorption filter according to the invention is used for a lens having a function of absorbing and cutting near infrared rays (a lens for a camera such as a digital camera, a cellular phone, or a vehicle camera and an optical lens such as a f-θ lens or a pickup lens), an optical filter for a semiconductor light-receiving element, a near infrared absorbing film and a near infrared absorbing plate that cut off heat rays for energy saving, an agricultural coating agent for the purpose of selective use of sunlight, a recording medium that uses a near infrared absorption heat, a near infrared absorption filter for electronic equipment and photos, safety glasses, sunglasses, a heat ray cut-off film, recording for optical character reading, the use of the confidential document copy prevention, an electrophotographic photoreceptor, laser welding, and the like. The near infrared ray absorption filter according to the invention is also useful for a noise cut filter for a CCD camera, a filter for a CMOS image sensor.

<Method for Manufacturing Cured Film and Near Infrared Ray Absorption Filter>

The cured film and the near infrared ray absorption filter according to the invention can be obtained by using the composition according to the invention. Specifically, the cured film and the near infrared ray absorption filter according to the invention can be manufactured by a step of forming a film by applying the composition according to the invention to a support and a step of drying a film. A film thickness and a laminate structure can be appropriately selected depending on purposes. A step of forming a pattern may be further performed.

A step of forming a film can be performed, by using the composition according to the invention on a support by a dropwise addition method (drop cast), a spin coater, a slit spin coater, a slit coater, screen printing, applicator coating, and the like. In a case of a dropwise addition method (drop cast), it is preferable to form a dropwise addition area of a composition having a photoresist as a partition wall on a support such that an even film in a predetermined film thickness can be obtained. The film thickness can be adjusted by a dropwise addition amount of a composition, a concentration of solid contents, and a size of the dropwise addition area.

The support may be a transparent substrate consisting of glass or the like. The support may be a solid-state imaging device, may be another substrate provided on a light receiving side of the solid-state imaging device, and may be a layer such as a planarizing layer or the like provided on a light receiving side of the solid-state imaging device.

In a step of drying a film, though the dry condition is different depending on respective components, types of solvents, use ratio, and the like, the dry condition is in a temperature of 60° C. to 150° C. for about 30 seconds to 15 minutes.

Examples of the step of forming a pattern include methods including a step of forming a film-shaped composition layer obtained by applying the composition according to the invention on the support, a step of exposing the composition layer in a pattern shape, and a step of forming a pattern by developing and removing unexposed parts, and the like. As a step of forming a pattern, photolithography or a dry etching method may be used for forming a pattern.

In the method for manufacturing a near infrared ray absorption filter, other steps may be included. The other steps are not particularly limited, and can be appropriately selected depending on purposes. Examples thereof include a step of treating a surface of a base material, a preheating step (prebaking step), a hardening treatment step, and a post heating step (post baking step).

<<Preheating Step and Post Heating Step>>

The heating temperature in the preheating step and the post heating step is preferably 80° C. to 200° C. The upper limit is preferably 150° C. or less. The lower limit is preferably 90° C. or higher.

The heating time in the preheating step and the post heating step is generally 30 to 240 seconds. The upper limit is preferably 180 seconds or lower, and the lower limit is preferably 60 seconds or longer.

<<Hardening Treatment Step>>

A hardening treatment step is a step of performing a hardening treatment on a formed film, if necessary. If this treatment is performed, mechanical strength of the near infrared ray absorption filter is improved.

The hardening treatment step is not particularly limited, and can be appropriately selected depending on purposes. Examples thereof suitably include an entire surface exposure treatment and an entire surface heating treatment. Here, the expression "exposure" according to the invention is used as a meaning of including not only light in various wavelengths but also radioactive ray irradiation such as electron rays or X rays.

The exposure is preferably performed by irradiation of radioactive rays. As the radioactive that can be used at the time of exposure, particularly, electron rays, KrF, ArF, ultraviolet rays such as g rays, h rays, and i rays, or visible light are preferably used.

Examples of an exposure technique include stepper exposure or exposure by a high pressure mercury vapor lamp.

An exposure amount is preferably 5 to 3,000 mJ/cm². The upper limit is preferably 2,000 mJ/cm² or lower and more preferably 1,000 mJ/cm² or lower. The lower limit is preferably 10 mJ/cm² or greater and more preferably 50 mJ/cm² or greater.

Examples of the method of the entire surface exposure treatment include a method for exposing an entire surface of the formed film. In a case where the composition according to the invention contains a polymerizable compound, hardening of the polymerizable components in the film is promoted by the entire surface exposure, such that hardening of the film further proceeds, and mechanical strength and durability further improve.

A device for performing the entire surface exposure is not particularly limited, and can be appropriately selected depending on purposes, and examples thereof suitably include an ultraviolet (UV) exposure machine such as a high pressure mercury vapor lamp.

Examples of the entire surface heating treatment method include a method for heating the entire surface of the formed film. With the heating of the entire surface, the film hardness of the pattern can be increased.

The heating temperature of the heating of the entire surface is preferably 100° C. to 260° C. The lower limit is preferably 120° C. or higher and more preferably 160° C. or higher. The upper limit is preferably 240° C. or less and more preferably 220° C. or less. If the heating temperature is in the range described above, a film having high strength can be easily obtained.

A heating time for heating the entire surface is preferably 1 to 180 minutes. The lower limit is preferably 3 minutes or longer and more preferably 5 minutes or longer. The upper limit is preferably 120 minutes or less.

A device for heating the entire surface is not particularly limited, and can be appropriately selected among well-known devices, depending on purposes. Examples thereof include a dry oven, a hot plate, and an IR heater.

<Solid-State Imaging Device and Infrared Sensor>

The solid-state imaging device according to the invention includes a cured film obtained by using the composition according to the invention.

The infrared sensor according to the invention includes the cured film obtained by using the composition according to the invention.

Hereinafter, one embodiment of the infrared sensor according to the invention is described by using FIG. 1.

In an infrared sensor 100 illustrated in FIG. 1, a reference numeral 110 is a solid-state imaging device.

An imaging area provided on the solid-state imaging device 110 has near infrared ray absorption filters 111 and color filters 112. The near infrared ray absorption filter 111 can be formed, for example, by using the composition according to the invention.

Areas 114 are provided between infrared ray transmission filters 113 and the solid-state imaging device 110. Resin layers (for example, transparent resin layers) through which light at a wavelength that transmits the infrared ray transmission filters 113 can be transmitted are provided on the areas 114. According to the embodiment illustrated in FIG. 1, resin layers are provided on the areas 114, but the infrared ray transmission filters 113 are formed on the areas 114. That is, the infrared ray transmission filters 113 may be formed on the solid-state imaging device 110.

Microlenses 115 are provided on incidence rays hυ side of the color filters 112 and the infrared ray transmission filters 113. A planarizing layer 116 is formed so as to cover the microlenses 115.

According to the embodiment illustrated in FIG. 1, film thicknesses of the color filters 112 and film thicknesses of the infrared ray transmission filters 113 are the same, but film thicknesses of the both may be different from each other.

According to one embodiment illustrated in FIG. 1, the color filters 112 are provided to be closer to the incidence rays hυ than the near infrared ray absorption filters 111, but the near infrared ray absorption filters 111 may be provided to be closer to the incidence rays hυ side than the color filters 112 by changing an order of the near infrared ray absorption filters 111 and the color filters 112.

According to the embodiment illustrated in FIG. 1, the near infrared ray absorption filters 111 and the color filters 112 are laminated to be adjacent to each other, but both of the filters do not have to be adjacent to each other and another layer may be interposed therebetween.

<<Near Infrared Ray Absorption Filter 111>>

Characteristics of the near infrared ray absorption filter 111 are selected depending on a light emitting wavelength of an infrared light emitting diode described below (infrared LED). For example, the near infrared ray absorption filter 111 can be formed by using the composition according to the invention described above.

<<Color Filter 112>>

The color filters 112 are not particularly limited, and color filters for forming pixels in the related art can be used. For example, disclosure in paragraphs 0214 to 0263 of JP2014-043556A can be referred to, and the contents thereof are incorporated to this specification.

<<Infrared Ray Transmission Filters 113>>

Characteristics of the infrared ray transmission filters 113 are selected depending on a light emitting wavelength of an infrared LED described below. For example, description below is provided in an assumption that a light emitting wavelength of an infrared LED is 830 nm.

With respect to the infrared ray transmission filters 113, a maximum value of the light transmittance in the thickness direction of the film in a wavelength range of 400 to 650 nm are preferably 30% or less, more preferably 20% or less, and even more preferably 10% or less, and particularly preferably 0.1% or less. The transmittance thereof preferably satisfies the condition above in the entire wavelength range of 400 to 650 nm. The maximum value is generally 0.1% or greater in the wavelength range of 400 to 650 nm.

With respect to the infrared ray transmission filters 113, a minimum value of light transmittance of the film in the thickness direction at a wavelength range of 800 nm or greater (preferably, 800 to 1,300 nm) is preferably 70% or greater, more preferably 80% or greater, even more preferably 90% or greater, and particularly preferably 99.9% or greater. This transmittance preferably satisfies the aforementioned condition in a portion of a wavelength range of 800 nm or greater and preferably satisfies the condition at a wavelength corresponding to the light emitting wavelength of an infrared LED described below. The minimum value of the light transmittance in a wavelength range of 900 to 1,300 nm is generally 99.9% or less.

The film thickness is preferably 100 µm or less, more preferably 15 µm or less, even more preferably 5 µm or less, and particularly preferably 1 µm or less. The lower limit value is preferably 0.1 µm. If the film thickness is in the range described above, it is possible to obtain a film satisfying the spectral characteristics as described above.

The spectral characteristics of the film and the method for measuring the film thickness are described below.

The film thickness is measured with a substrate having the film after drying by using a stylus-type surface shape measuring instrument (DEKTAK150 manufactured by ULVAC Technologies, Inc.).

The spectral characteristics of the film are values obtained by measuring transmittance in a wavelength range of 300 to 1,300 nm by using a spectrophotometer (ref glass substrate) of a ultraviolet-visible-near infrared ray spectrophotometer (U-4100 manufactured by Hitachi High-Technologies Corporation).

The condition of the light transmittance may be achieved by any means, but, for example, the conditions of the light transmittance can be suitably achieved by causing the composition to contain a coloring agent and adjusting a type and a content of the coloring agent. Examples of the coloring agent include the compound having a maximum absorption wavelength in a wavelength range of 400 to 700 nm. The coloring agent may be a pigment or may be a dye. As the coloring agent, for example, coloring agents disclosed in paragraph numbers 0019 to 0028 of JP2013-064998A may be used, and the contents thereof may be incorporated with this specification.

For example, the infrared ray transmission filters 113 can be manufactured by using the composition (infrared transmission composition) including a coloring agent containing two or more types of coloring agents selected from a red coloring agent, a yellow coloring agent, a blue coloring agent, and a violet coloring agent.

The content of a pigment in the coloring agent is preferably 95 to 100 mass % with respect to the total amount of the coloring agent. The lower limit is more preferably 97 mass % or greater and even more preferably 99 mass % or greater.

As the preferable embodiment of the coloring agent, two or more coloring agents selected from a red coloring agent, a yellow coloring agent, a blue coloring agent, and a violet coloring agent are preferably contained, and a red coloring agent, a yellow coloring agent, a blue coloring agent, and a violet coloring agent are more preferably contained. As preferable specific examples, color index (C.I.) Pigment Red 254, C.I. Pigment Yellow 139, C.I. Pigment Blue 15:6, and C.I. Pigment Violet 23 are preferably contained.

In a case where the coloring agent contained in the infrared transmission composition is a combination of a red coloring agent, a yellow coloring agent, a blue coloring agent, and a violet coloring agent, it is preferable that a mass ratio of a red coloring agent is 0.2 to 0.5, a mass ratio of a yellow coloring agent is 0.1 to 0.2, a mass ratio of a blue coloring agent is 0.25 to 0.55, and a mass ratio of a violet coloring agent is 0.05 to 0.15 with respect to a total amount of the coloring agent. It is more preferable that a mass ratio of a red coloring agent is 0.3 to 0.4, a mass ratio of a yellow coloring agent is 0.1 to 0.2, a mass ratio of a blue coloring agent is 0.3 to 0.4, and a mass ratio of a violet coloring agent is 0.05 to 0.15 with respect to a total amount of the coloring agent.

Subsequently, an imaging device is described as an example to which the infrared sensor according to the invention is applied. As the infrared sensor, there exist a motion sensor, a proximity sensor, a gesture sensor, and the like.

Figure 2:
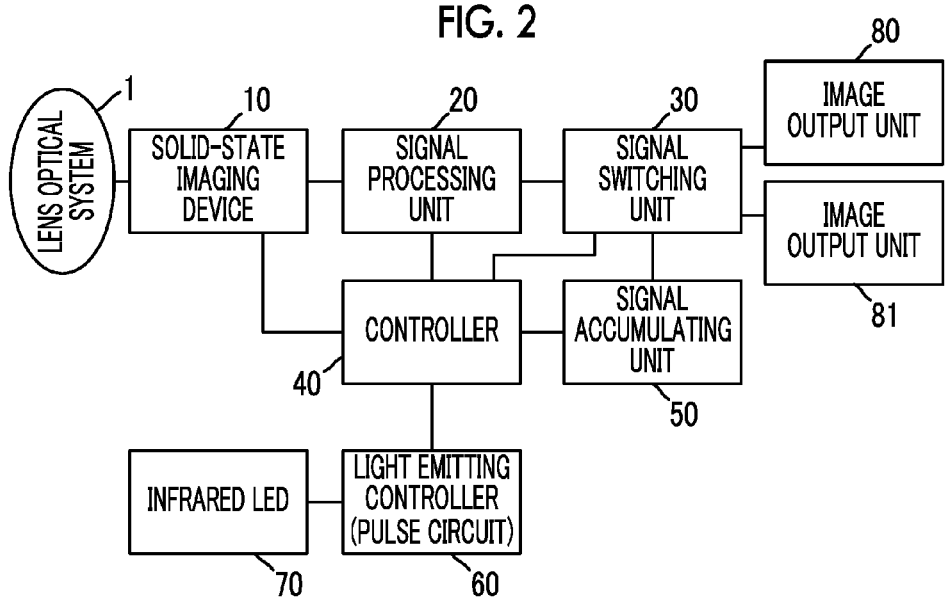
FIG. 2 is a functional block diagram schematically illustrating an imaging device to which an infrared sensor of the invention is applied.

FIG. 2 is a functional block diagram of an imaging device. The imaging device comprises a lens optical system 1, a solid-state imaging device 10, a signal processing unit 20, a signal switching unit 30, a controller 40, a signal accumulating unit 50, a light emitting controller 60, an infrared LED 70 of a light emitting element that emitting infrared light, and image output units 80 and 81. As the solid-state imaging device 10, the infrared sensor 100 described above can be used. All or a portion of the configurations except for those of the solid-state imaging device 10 and the lens optical system 1 may be formed on the same semiconductor substrate. With respect to the respect configurations of the imaging device, paragraphs 0032 to 0036 of JP2011-233983A can be referred to, and the contents thereof are incorporated to this specification.

It is possible to incorporate a camera module having the solid-state imaging device and the near infrared ray absorption filter described above with the imaging device.

<Compound>

Subsequently, the compound according to the invention is described.

The compound according to the invention is a compound represented by Formula (1A) described in the near infrared ray absorption substance of the composition according to the invention, and suitable ranges thereof are also the same.

The compound according to the invention preferably has a maximum absorption wavelength in a wavelength range of 700 to 1,000 nm in the liquid absorption spectrum. For example, the lower limit is more preferably 800 nm or greater and even more preferably 850 nm or greater. For example, the upper limit is more preferably 995 nm or less and even more preferably 990 nm or less.

The measuring solvent used in the measuring of the absorption spectrum in the liquid of the compound may be a solvent that allows measuring the absorption spectrum of the liquid of the compound. Examples thereof include the measuring solvent described above, and preferable examples thereof include chloroform, ethyl acetate, and tetrahydrofuran.

The half-width in the maximum absorption wavelength of the compound is preferably 60 nm or less, more preferably 50 nm or less, and even more preferably 45 nm or less. For example, the lower limit is preferably 1 nm or greater.

The value obtained by dividing absorbance at a wavelength of 550 nm by absorbance at the maximum absorption wavelength is preferably 0.015 or less and more preferably 0.014 or less. For example, the lower limit is preferably 0.001 or greater.

For example, the compound according to the invention can be preferably used in the forming of a near infrared ray absorption filter and the like that blocks light at a wavelength of 700 to 1,000 nm. The compound according to the invention can be also used in a plasma display panel, a near infrared ray absorption filter for a solid-state imaging device or the like, an optical filter in a heat ray shielding film, and a photothermal conversion material in compact disc-recordable (CD-R) or a flash melting material. The compound according to the invention can be also used as an information display material in security ink or invisible bar code ink.

EXAMPLES

Hereinafter, the invention is described in detail with reference to examples. Materials, use amounts, ratios, process details, process orders, and the like provided in the examples below can be appropriately changed without departing from the gist of the invention. Accordingly, ranges of the invention are not limited to the specific examples described below. Unless described otherwise, "%" and "parts" are based on a mass.

In chemical formulae below, Me represents a methyl group, and Ph represents a phenyl group. NMR is an abbreviation of nuclear magnetic resonance.

(Synthesis of Compound D-1)

The compound D-1 was synthesized with reference to Chem. Eur. J. 2009, 15, 4857.

mass of water, so as to filtrate a deposit. Blast drying was performed on this crystal, so as to obtain 5.0 parts by mass of an intermediate B.

1.3 parts by mass of a 60 mass % sodium hydride and 10 parts by mass of tetrahydrofuran were put into a flask, and 4.0 parts by mass of tert-butyl cyanoacetate was added dropwise in an ice bath. After stirring was performed for one hour at room temperature, 5.0 parts by mass of the intermediate B was added and stirred for 12 hours. The reaction solution was poured into 75 parts by mass of water, 3 parts by mass of acetic acid was added, and deposits were filtrated. Blast drying was performed on this crystal at 50° C., so as to obtain 4.6 parts by mass of an intermediate C.

4.0 parts by mass of the intermediate C, 12 parts by mass of trifluoro acetate, and 24 parts by mass of dichloromethane were put into a flask and stirred at 60° C. for one hour. After reaction, a sodium carbonate aqueous solution was added, and an organic layer was extracted with chloroform. A solvent was removed under reduced pressure, and the obtained crystal was purified by recrystallization with ethyl acetate. Blast drying was performed on this crystal at 50° C., so as to obtain 2.0 parts by mass of an intermediate 3-0.

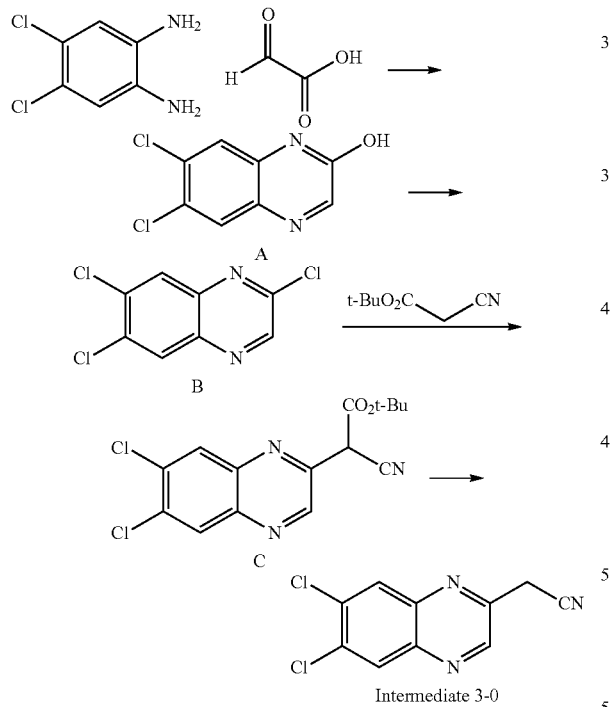

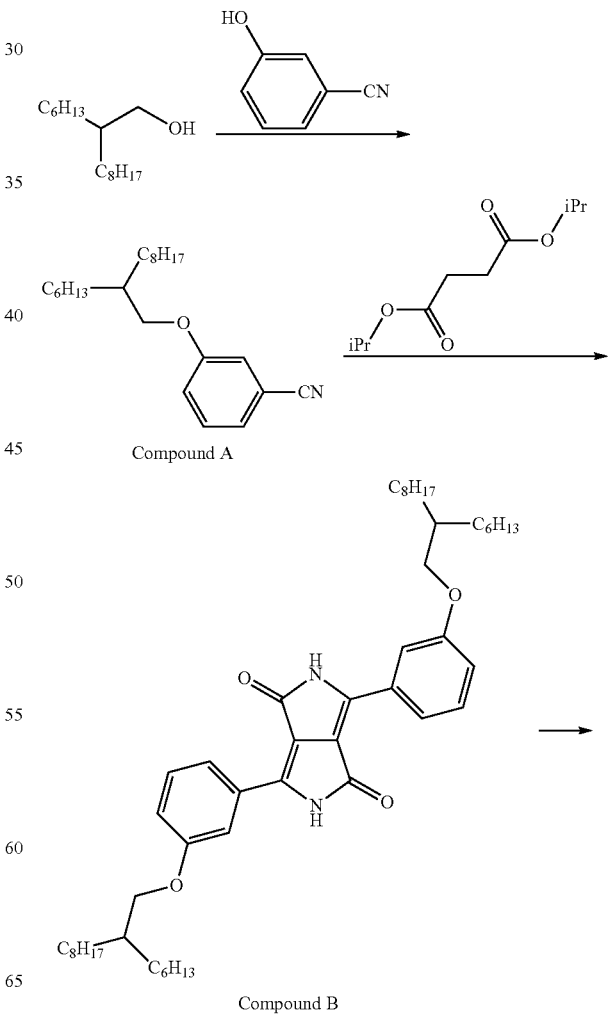

5.0 parts by mass of 4,5-dichloro-1,2-phenylenediamine, 2.9 parts by mass of glyoxylic acid monohydrate, and 120 parts by mass of ethanol were put into a flask and stirred for 12 hours in a heating reflux condition. After reaction, deposits were filtrated. Blast drying was performed on this crystal at 50° C., so as to obtain 5.5 parts by mass of an intermediate A.

5.0 parts by mass of the intermediate A and 30 parts by mass of phosphorus oxychloride were put into a flask and were stirred for two hours in a heating reflux condition. After reaction, the reaction solution was poured into 300 parts by -continued

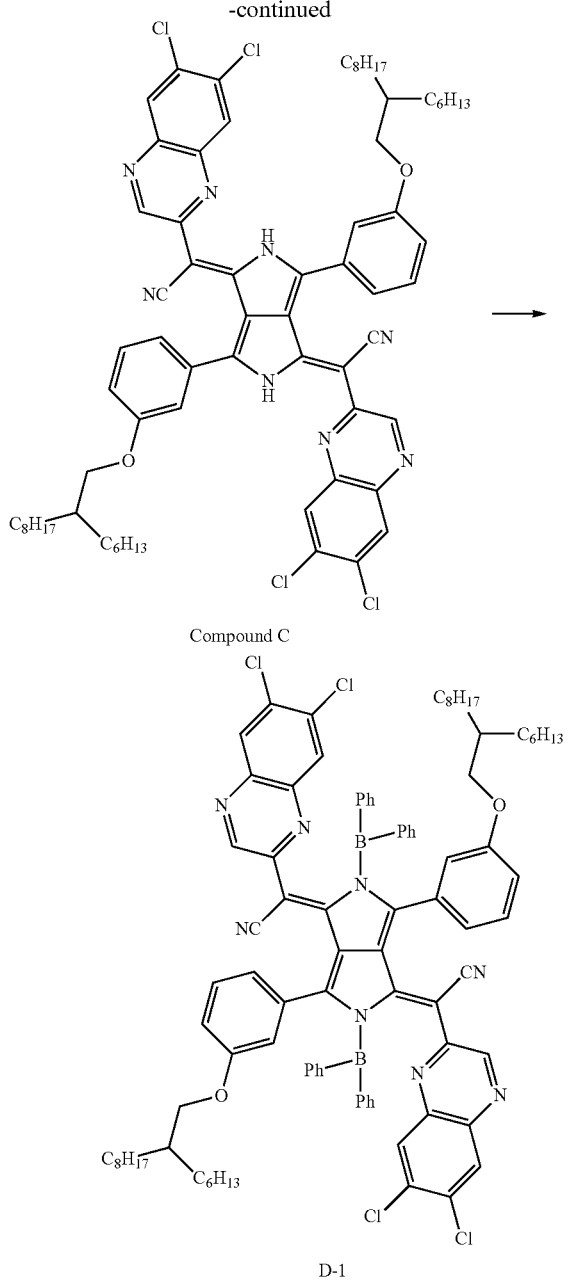

Compound C

D-1

46.3 parts by mass of 2-hexyldecan-1-ol (FINEOXOCOL 1600, manufactured by Nissan Chemical Industries, Ltd.), and 23.2 parts by mass of triethylamine were stirred in 190 parts by mass of toluene, and 24.1 parts by mass of methanesulfonyl chloride was added dropwise at −10° C. After dropwise addition was completed, reaction was performed for two hours at 30° C. An organic layer was extracted by a liquid separation operation, and a solvent was distilled under reduced pressure.

After the solvent was distilled, 25 parts by mass of 3-cyanophenol, 32 parts by mass of potassium carbonate, and 100 parts by mass of dimethylacetamide were added thereto, and reaction was performed at 100° C. for 24 hours. An organic layer was extracted by a liquid separation operation, the organic layer was washed with a sodium hydroxide aqueous solution, and the solvent was distilled under reduced pressure, so as to obtain 64 parts by mass of a compound A which is a pale yellow liquid.

20 parts by mass of the compound A, 7 parts by mass of diisopropyl succinate, 20 parts by mass of t-amyl alcohol, and 13 parts by mass of potassium t-butoxide were input to a flask and stirred at 120° C. for three hours. After the reaction, 50 parts by mass of methanol and 50 parts by mass of water were added and deposits were filtrated. Blast drying was performed on this crystal at 50° C., so as to obtain 12.2 parts by mass of a compound B.

5 parts by mass of the compound B and 3.7 parts by mass of an intermediate 3-0 were stirred in 300 parts by mass of toluene, 6 parts by mass of phosphorus oxychloride was subsequently added, and stirring was performed at 140° C. for three hours. After the reaction, cooling was performed to room temperature, 600 parts by mass of methanol was added, and stirring was further performed for 30 minutes. The deposited crystal was filtrated, so as to obtain 5.7 parts by mass of a compound C.

8 parts by mass of titanium chloride was added to 50 parts by mass of toluene containing 6 parts by mass of 2-aminoethyl diphenylborinate, and stirring was performed at 35° C. for 30 minutes. Subsequently, 3 parts by mass of the compound C was added, and further stirring was performed for two hours in a heating reflux condition. Cooling was performed to room temperature, 130 parts by mass of methanol was added, and stirring was further performed for 30 minutes. The deposited crystal was filtrated and purified with silica column chromatography (hexane/chloroform solvent), so as obtain 3.4 parts by mass of the compound D-1 at a yield of 89%.

Details of $^1$H-NMR (CDCl$_3$) were 60.82-1.70 (m, 78H), 3.30-3.53 (m, 4H), 5.88-5.90 (m, 4H), 6.90-6.92 (m, 4H), 7.18-7.38 (m, 10H), 7.79 (s, 2H), 8.21 (s, 2H), and 8.98 (s, 2H).

(Synthesis of Compound D-2)

A compound D-2 was synthesized in the same method as the compound D-1, except for changing 2-hexyldecan-1-ol used when the compound A was synthesized in the synthesis of the compound D-1 to FINEOXOCOL 2000 (manufactured by Nissan Chemical Industries, Ltd.).

Details of $^1$H-NMR (CDCl$_3$) were 80.87-0.92 (m, 12H), 1.26-1.55 (m, 48H), 1.70-1.73 (m, 2H), 3.34-3.53 (m, 4H), 5.88-5.90 (m, 4H), 6.90-6.92 (m, 4H), 7.15-7.39 (m, 10H), 7.78 (s, 2H), 8.21 (s, 2H), and 8.98 (s, 2H).

(Synthesis of Compounds D-3 to D-8, D-10, D-11, D-19, D-28, D-29, D-31 to D-33, D-35 to D-37, D-43, D-45, and D-48)

Compounds D-3 to D-8, D-10, D-11, D-19, D-28, D-29, D-31 to D-33, D-35 to D-37, D-43, D-45, and D-48 were synthesized in the method in conformity with the compound D-1.

(Comparative Compound E-1)

A comparative compound E-1 was synthesized in the same manner as the compound D-1, except for changing 3-cyanophenol used when the compound A was synthesized in the compound D-1, to 4-cyanophenol.

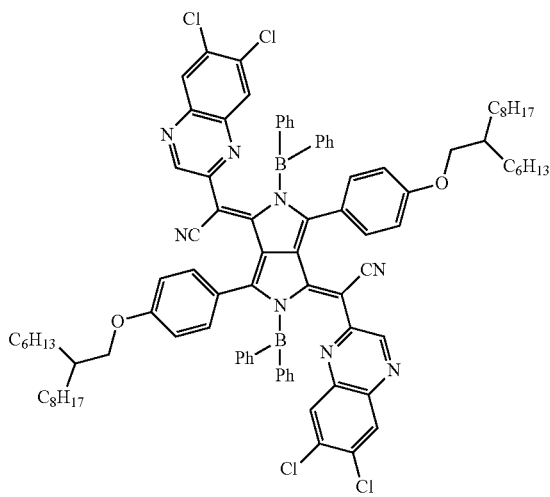

E-1

—Evaluation of Maximum Absorption Wavelength, Half-Width, and Absorbance Ratio—Respective compounds were dissolved in measuring solvents (concentration: $2.5 \times 10^{-6}$ mol/L) described in the table below so as to measure an absorption spectrum (Optical path length: 10 mm).

Figure 3:
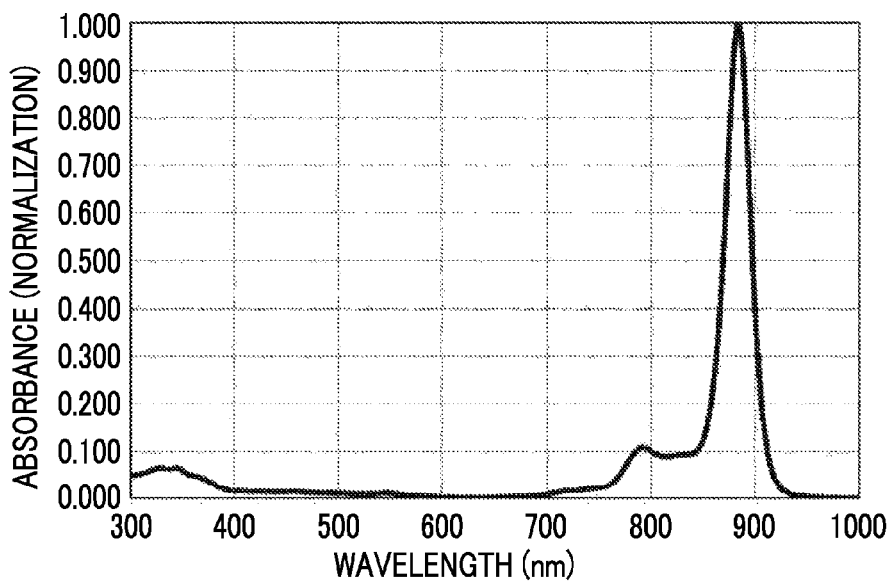
FIG. 3 is a diagram illustrating a liquid absorption spectrum of a compound D-1.

Maximum absorption wavelengths (λmax) of absorption spectrums, half-widths of the maximum absorption wavelengths, and absorbance ratios (550 nm/λmax) which are values obtained by dividing absorbance at a wavelength of 500 nm by absorbance at the maximum absorption wavelength with respect to respective compounds are presented in Table 1 below. FIG. 3 illustrates an absorption spectrum of the compound D-1 in chloroform.

From the results above, compounds of the examples had absorbance ratios of 0.015 or less and had excellent transparency in a visible region. In contrast, the compounds of the comparative examples had absorbance ratios of greater than 0.015 and had deteriorated transparency in a visible region compared with that of the compounds of the examples.

FIG. 3 illustrates an absorption spectrum of the compound D-1 in chloroform.

(Preparation of Composition)

Compositions below were mixed so as to prepare the composition. A solid content of the composition is 31 mass % and a content of the near infrared ray absorption substance with respect to the total solid content of the composition was 7.5 mass %.

<Composition>

Near infrared ray absorption substance (Compound shown in Table 2): 2.3 parts

Resin 1 (structure below): 12.9 parts

Polymerizable compound: Dipentaerythritol hexaacrylate (manufactured by Nippon Kayaku Co., Ltd., Product name: KAYARAD DPHA): 12.9 parts Photopolymerization initiator: IRGACURE OXE 01 [2-(o-benzoyloxime)-1-[4-(phenylthio)phenyl]-1,2-octanedione] (manufactured by BASF SE Corp.): 2.5 parts Ultraviolet absorbing agent: UV503 (Daito Chemical Co., Ltd.): 0.5 parts Surfactant: Megaface F-781F (manufactured by DIC Corporation, fluorine-containing polymer-type surfactant): 0.04 parts Polymerization inhibitor: p-methoxyphenol: 0.006 parts Cyclohexanone: 49.6 parts Propylene glycol monomethyl ether acetate: 19.3 parts Resin 1: Structure below (A ratio in a repeating unit is a molar ratio), Mw=11,500

Synthesis was performed by a method disclosed in paragraphs 0247 to 0249 of JP2012-198408A.

TABLE 1

|  | Compound | Measuring solvent | Maximum absorption wavelength [nm] | Half-width [nm] | Absorbance ratio (550 nm/λmax) |
|---|---|---|---|---|---|
| Example A1 | D-1 | Chloroform | 884 | 29 | 0.011 |
| Example A2 | D-1 | Ethyl acetate | 880 | 30 | 0.011 |
| Example A3 | D-1 | Tetrahydrofuran | 884 | 29 | 0.01 |
| Example A4 | D-2 | Chloroform | 884 | 29 | 0.01 |
| Example A5 | D-2 | Tetrahydrofuran | 884 | 29 | 0.01 |
| Example A6 | D-3 | Chloroform | 877 | 29 | 0.013 |
| Example A7 | D-4 | Chloroform | 883 | 29 | 0.012 |
| Example A8 | D-5 | Chloroform | 884 | 29 | 0.01 |
| Example A9 | D-6 | Chloroform | 872 | 32 | 0.01 |
| Example A10 | D-7 | Chloroform | 863 | 29 | 0.013 |
| Example A11 | D-8 | Chloroform | 866 | 31 | 0.01 |
| Example A12 | D-10 | Chloroform | 814 | 30 | 0.01 |
| Example A13 | D-11 | Chloroform | 779 | 30 | 0.009 |
| Example A14 | D-19 | Chloroform | 719 | 23 | 0.011 |
| Example A15 | D-28 | Chloroform | 863 | 29 | 0.006 |
| Example A16 | D-29 | Chloroform | 862 | 28 | 0.006 |
| Example A17 | D-31 | Chloroform | 884 | 28 | 0.01 |
| Example A18 | D-32 | Chloroform | 884 | 28 | 0.01 |
| Example A19 | D-33 | Chloroform | 884 | 28 | 0.007 |
| Example A20 | D-35 | Chloroform | 743 | 28 | 0.003 |
| Example A21 | D-36 | Chloroform | 748 | 30 | 0.003 |
| Example A22 | D-37 | Chloroform | 753 | 31 | 0.003 |
| Example A23 | D-43 | Chloroform | 748 | 30 | 0.003 |
| Example A24 | D-45 | Chloroform | 783 | 28 | 0.002 |
| Example A25 | D-48 | Chloroform | 769 | 34 | 0.003 |
| Comparative Example A1 | E-1 | Chloroform | 884 | 31 | 0.019 |

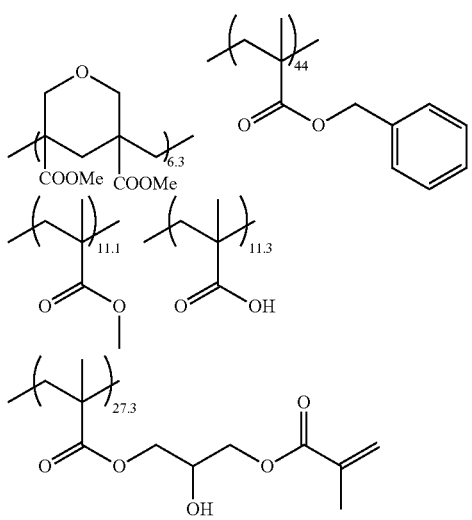

<Manufacturing of Near Infrared Ray Absorption Filter>

Glass substrates (1737 manufactured by Corning Incorporated) were coated with respective compositions by using a spin coater such that film thicknesses after drying become 1.0 μm, and a heating treatment (prebaking) was performed for 120 seconds by using a hot plate of 100° C.

Subsequently, beta exposure was performed by 500 mJ/cm$^2$ by using an i-ray stepper exposure device FPA-3000i5+ (manufactured by Canon Inc.). Subsequently, puddle development was performed at 23° C. for 60 seconds by using CD-2060 (manufactured by Fujifilm Electronic Materials), a rinse treatment was performed with pure water on a glass substrate on which a beta coloration layer was formed, and spray drying was performed.

The heating treatment (post baking) was performed for 300 seconds by using a hot plate of 200° C., so as to obtain a near infrared ray absorption filter.

<<Light Fastness>>

After the near infrared ray absorption filter was irradiated with a xenon lamp was applied by 50,000 lux for 20 hours (corresponding to 1,000,000 lux·h), an ΔEab value of a color difference before and after a light-fast test was measured. A smaller ΔEab value indicates more satisfactory light fastness.

The ΔEab value is a value obtained from a color difference equation below according to a CIE 1976 (L*, a*, b*) space color system (Handbook of Color Science, New Edition, edited by the Color Science Association of Japan, (1985), p. 266).

$$\Delta Eab = \{(\Delta L^*)^2 \pm (\Delta a^*)^2 + (\Delta b^*)^2\}^{1/2}$$

5: ΔEab value<3
4: 3≤ΔEab value<5
3: 5≤ΔEab value<10
2: 10≤ΔEab value<20
1: 20≤ΔEab value <<Heat Resistance>>

After the near infrared ray absorption filter was heated to 260° C. for 30 minutes by a hot plate, the ΔEab value of a color difference before and after heat resistance test was measured using a color meter MCPD-1000 (manufactured by Otsuka Electronics Co., Ltd.), so as to evaluate a criterion below. A smaller ΔEab value indicates more satisfactory heat resistance.

5: ΔEab value<3
4: 3≤ΔEab value<5
3: 5≤ΔEab value<10
2: 10≤ΔEab value<20
1: 20≤ΔEab value <<Solubility>>

Solubility of the compound to propylene glycol monomethyl ether acetate was visually observed.

A: Solubility 2% or greater
B: Solubility 0.5% or greater and less than 2%
C: Solubility less than 0.5%

<<Near Infrared Shielding Property Evaluation>>

Transmittance of the respective near infrared ray absorption filters at maximum absorption wavelengths was measured by a spectrophotometer U-4100 (manufactured by Hitachi High-Technologies Corporation). Near infrared shielding properties were evaluated with criteria below. Results thereof are presented in the table below.

A: transmittance of maximum absorption wavelength≤5%
B: 5%<transmittance of maximum absorption wavelength≤7%
C: 7%<transmittance of maximum absorption wavelength≤10%
D: 10%<transmittance of maximum absorption wavelength <<Evaluation of Transparency in a Visible Region>>

Transmittance of the respective near infrared ray absorption filters at a wavelength of 500 to 600 nm was measured by a spectrophotometer U-4100 (manufactured by Hitachi High-Technologies Corporation). Transparency in a visible region was evaluated with criteria below. Results thereof are presented in the table below.

A: 95%≤minimum value of transmittance at a wavelength of 500 to 600 nm
B: 90%≤minimum value of transmittance at a wavelength of 500 to 600 nm<95%
C: 80%≤minimum value of transmittance at a wavelength of 500 to 600 nm<90%
D: Minimum value of transmittance at a wavelength of 500 to 600 nm<80%

TABLE 2

| | Compound | Heat resistance | Light fastness | Solubility | Near infrared shielding properties | Transparency in visible region |
|---|---|---|---|---|---|---|
| Example B1 | D-1 | 5 | 5 | A | A | A |
| Example B2 | D-2 | 5 | 5 | A | A | A |
| Example B3 | D-3 | 5 | 5 | A | A | A |
| Example B4 | D-4 | 4 | 5 | B | A | B |
| Example B5 | D-5 | 5 | 5 | B | A | B |
| Example B6 | D-6 | 5 | 5 | A | A | A |
| Example B7 | D-7 | 5 | 5 | A | A | B |
| Example B8 | D-8 | 5 | 5 | A | A | A |
| Example B9 | D-10 | 5 | 5 | A | A | A |
| Example B10 | D-11 | 5 | 5 | B | A | B |

TABLE 2-continued

| | Compound | Heat resistance | Light fastness | Solubility | Near infrared shielding properties | Transparency in visible region |
|---|---|---|---|---|---|---|
| Example B11 | D-28 | 5 | 5 | A | A | A |
| Example B12 | D-29 | 5 | 5 | A | A | A |
| Example B13 | D-31 | 5 | 5 | A | A | A |
| Example B14 | D-32 | 5 | 5 | A | A | A |
| Example B15 | D-33 | 5 | 5 | A | A | A |
| Example B16 | D-35 | 5 | 5 | A | A | A |
| Example B17 | D-36 | 5 | 5 | A | A | A |
| Example B18 | D-37 | 4 | 5 | A | A | A |
| Example B19 | D-43 | 5 | 5 | A | A | A |
| Example B20 | D-45 | 5 | 5 | A | A | A |
| Example B21 | D-48 | 5 | 4 | A | A | A |
| Comparative Example B1 | E-1 | 5 | 5 | C | A | C |

According to the results above, the near infrared ray absorption filters of the examples had excellent near infrared shielding properties and excellent transparency in a visible region. Heat resistance and light fastness were also excellent. The compounds of the examples also had excellent solubility.

In contrast, the compounds of the comparative examples had deteriorated transparency in a visible region. Solubility of the compounds were also deteriorated.

The same effects were also able to be obtained in a case where the same amounts of compounds D-9, D-12 to D-27, D-30, D-34, D-38 to D-42, D-44, D-46, D-47, and D-49 to 90 were used instead of the compound D-1 in Example B1.

The same excellent effects were also able to be obtained in a case where the content of the near infrared ray absorption substance was changed to 1 mass %, 5 mass %, 10 mass %, and 15 mass % with respect to the total solid content of the composition in Examples B1 to B21.

The same effect was able to be obtained also in a case where propylene glycol monomethyl ether was changed to cyclopentanone in the same amount in Example B 1.

The same effect was able to be obtained also in a case where filtration was performed by using DFA4201NXEY (0.45 μm nyon filter) manufactured by Nihon Pall Ltd. after the preparation of the respective compositions.

EXPLANATION OF REFERENCES

1: lens optical system
10: solid-state imaging device
20: signal processing unit
30: signal switching unit
40: controller
50: signal accumulating unit
60: light emitting controller
70: infrared LED
80, 81: image output units
100: infrared sensor
110: solid-state imaging device
111: near infrared ray absorption filter
112: color filter
113: infrared ray transmission filter
114: area
115: microlens
116: planarizing layer
hυ: incidence ray

What is claimed is:

1. A composition comprising:
a compound represented by Formula (1) below:

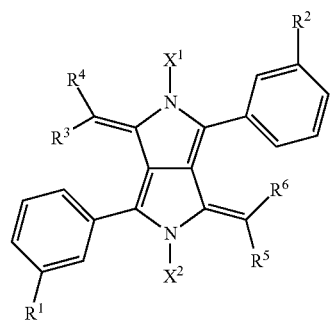

(1)

wherein $X^1$ and $X^2$ each independently represents an alkyl group, an alkoxy group, an aryl group, a heteroaryl group, a metal atom, a group represented by $-BR^{21}R^{22}$, or a group represented by Formula (2-4) described below;
$R^{21}$ and $R^{22}$ each independently represents a halogen atom, an alkyl group, an alkoxy group, an aryl group, a heteroaryl group, or a group represented by Formula (2-4) described below;

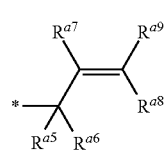

(2-4)

wherein $R^{a5}$ to $R^{a9}$ each independently represents a hydrogen atom, an alkyl group, an alkoxy group, an aryl group, or a heteroaryl group; * represents a coupler hand with Formula (1);
$R^1$ and $R^2$ each independently represents a halogen atom; and
one of $R^3$ and $R^4$ and one of $R^5$ and $R^6$ each independently represents an electron-withdrawing group, and the other of $R^5$ and $R^4$ and the other of $R^5$ and $R^6$ each independently represents a heteroaryl group.

2. The composition of claim 1, wherein the electron-withdrawing group has a Hammett σp value of 0.2 or greater.

3. The composition of claim 1, wherein the electron-withdrawing group has a Hammett σp value of 0.35 or greater.

4. The composition of claim 1, wherein the electron-withdrawing group has a Hammett σp value of 0.8 or greater.

5. A compound represented by Formula (1) below:

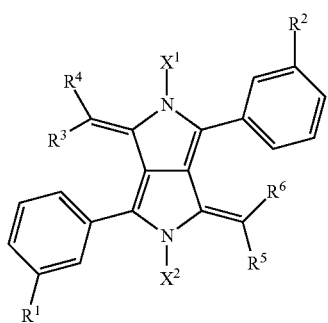

(1)

wherein $X^1$ and $X^2$ each independently represents an alkyl group, an alkoxy group, an aryl group, a heteroaryl group, a metal atom, a group represented by —$BR^{21}R^{22}$, or a group represented by Formula (2-4) described below;

$R^{21}$ and $R^{22}$ each independently represents a halogen atom, an alkyl group, an alkoxy group, an aryl group, a heteroaryl group, or a group represented by Formula (2-4) described below;

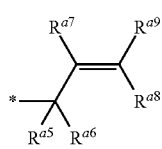

(2-4)

wherein $R^{a5}$ to $R^{a9}$ each independently represents a hydrogen atom, an alkyl group, an alkoxy group, an aryl group, and a heteroaryl group; *represents a coupler hand with Formula (1);

$R^1$ and $R^2$ each independently represents a halogen atom; and one of $R^3$ and $R^4$ and one of $R^5$ and $R^6$ each independently represents an electron-withdrawing group, and the other of $R^3$ and $R^4$ and the other of $R^5$ and $R^6$ each independently represents a heteroaryl group.

6. A composition comprising:
a compound represented by Formula (1) below:

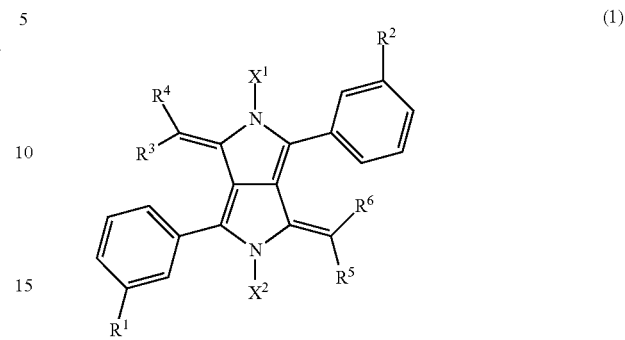

(1)

wherein $X^1$ and $X^2$ each independently represents an alkyl group, an alkoxy group, an aryl group, a heteroaryl group, a metal atom, a group represented by —$BR^{21}R^{22}$, or a group represented by Formula (2-4) described below; at least one of $X^1$ and $X^2$ is a group represented by -$BR^{21}R^{22}$;

wherein the compound represented by Formula (1) is a pyrrolopyrrole boron compound;

$R^{21}$ and $R^{22}$ each independently represents a halogen atom, an alkyl group, an alkoxy group, an aryl group, a heteroaryl group, or a group represented by Formula (2-4) described below;

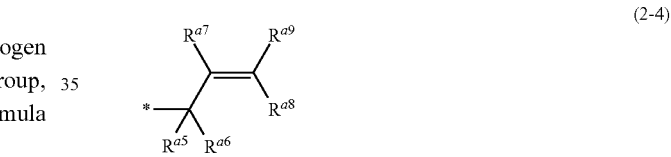

(2-4)

$R^3$ to $R^6$ each independently represents an alkyl group, an alkenyl group, an alkenyl group, an aryl group, a heteroaryl group, an amino group, an alkoxy group, an aryloxy group, a heteroaryloxy group, an acyl group, an arylcarbonyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heteroarylthio group, an alkylsulfonyl group, an arylsulfonyl group, a sulfinyl group, an ureido group, a phosphoric acid amide group, a hydroxyl group, a mercapto group, a halogen atom, a cyano group, a sulfo group, a carboxyl group, a nitro group, a hydroxamic acid group, a sulfino group, a hydrazino group, an imino group, or a silyl group; $R^3$ and $R^4$, and $R^5$ and $R^6$ may be respectively bonded to each other to form a ring; and wherein, in Formula (1), $R^1$ and $R^2$ each independently represent a branched alkoxy group.

* * * * *